United States Patent [19]

Bodor

[11] Patent Number: 4,996,335

[45] Date of Patent: Feb. 26, 1991

[54] SOFT STEROIDS HAVING ANTI-INFLAMMATORY ACTIVITY

[75] Inventor: Nicholas S. Bodor, 7211 SW. 97th La., Gainesville, Fla. 32608

[73] Assignee: Nicholas S. Bodor, Gainesville, Fla.

[21] Appl. No.: 807,034

[22] Filed: Dec. 9, 1985

Related U.S. Application Data

[63] Continuation of Ser. No. 626,535, Jun. 29, 1984, abandoned, which is a continuation of Ser. No. 418,458, Sep. 15, 1982, abandoned, which is a continuation-in-part of Ser. No. 265,785, May 21, 1981, abandoned, which is a continuation-in-part of Ser. No. 168,453, Jul. 10, 1980, abandoned.

[51] Int. Cl.[5] ......................... C07J 3/00; A01N 43/50

[52] U.S. Cl. .................................... 552/610; 552/611; 552/612

[58] Field of Search ..................... 260/397.1; 514/169; 552/610

[56] References Cited

U.S. PATENT DOCUMENTS

| | | | |
|---|---|---|---|
| 3,558,675 | 1/1971 | Sarett et al. | 260/397.4 |
| 3,856,828 | 12/1974 | Phillipps et al. | 260/397.1 |
| 4,093,721 | 6/1978 | Phillipps et al. | 260/397.1 |
| 4,242,334 | 12/1980 | Stache et al. | 260/397.45 |
| 4,263,289 | 4/1981 | Edwards | 260/397.1 |
| 4,377,575 | 3/1983 | Stache et al. | 260/397.45 |

*Primary Examiner*—Stanley J. Friedman
*Assistant Examiner*—Theodore J. Criares
*Attorney, Agent, or Firm*—Burns, Doane, Swecker & Mathis

[57] ABSTRACT

The invention provides novel soft steroidal anti-inflammatory agents, pharmaceutical compositions containing said agents, and methods of administering same to mammals in the treatment of inflammation. Preferred compounds of the invention include haloalkyl 17α-alkoxycarbonyloxy-11β-hydroxyandrost-4-en-3-one-17β-carboxylates and the corresponding $\Delta^{1,4}$ compounds, optionally bearing 6α- and/or 9α-fluorine and 16α- or 16β-methyl substituents. Especially preferred compounds include haloalkyl 17α-alkoxycarbonyloxy-9α-fluoro-11β-hydroxy-16-methylandrosta-1,4-dien-3-one-17β-carboxylates.

113 Claims, No Drawings

SOFT STEROIDS HAVING ANTI-INFLAMMATORY ACTIVITY

CROSS-REFERENCE TO RELATED APPLICATIONS

This application is a continuation of application Ser. No. 626,535, filed June 29, 1984, now abandoned, which is a continuation of Ser. No. 418,458, filed Sept. 18, 1982, now abandoned, which is a continuation-in-part of Ser. No. 265,785, filed May 21, 1981, now abandoned, which was a continuation-in-part of Ser. No. 168,453, filed July 10, 1980, now abandoned. The said earlier applications are expressly incorporated by reference herein in their entireties and relied upon.

TECHNICAL FIELD OF THE INVENTION

The invention relates to novel soft steroids having anti-inflammatory activity, pharmaceutical compositions containing said soft steroids, novel chemical intermediates useful in the preparation of the steroids, and methods of administering said steroids to mammals in the treatment of inflammation.

BACKGROUND ART

Successful predictions on a rational basis of the biological activity of compounds leading to new drugs are the main objective of drug designers. This has usually been achieved by considering a known bioactive molecule as the basis for structural modifications, either by the group or biofunctional moieties approach or by altering the overall physical-chemical properties of the molecule. Thus, the main aim has been to design, synthesize, and test new compounds structurally analogous to the basic bioactive molecule which have, however, improved therapeutic and/or pharmacokinetic properties. Although "vulnerable" moieties have been identified as the ones whose role is the bioinactivation or metabolic elimination of the drug after it has performed its role, little or no attention has been paid in the drug-design process to the rational design of the metabolic disposition of the drugs. This has been the case despite the fact that the toxicity of a number of bioactive molecules is due to their increased elimination half-life, stability, or other factors introduced during the design of increasing their activity. Drugs and particularly their metabolic processes contribute to the various toxic processes by formation of active metabolites. The phenomenon of metabolic activation to reactive intermediates which covalently bind to tissue macromolecules is the initial step in cell damage. It is also clear that the most toxic metabolites will not survive long enough to be excreted and identified; thus, studies of the stable metabolites may provide misleading information.

It is clear that, in order to prevent and/or reduce toxicity problems related to drugs, the metabolic disposition of the drugs should be considered at an early stage of the drug-design process. This is true particularly when one considers that the body can attack and alter chemically quite stable structures and that, even if a drug is 95% excreted unchanged, the unaccounted small portion can, and most likely will, cause toxicity.

"Soft drugs" can be defined as biologically active chemical compounds (drugs) which might structurally resemble known active drugs (soft analogues) or could be entirely new types of structures, but which are all characterized by a predictable in vivo destruction (metabolism) to nontoxic moieties, after they achieve their therapeutic role. The metabolic disposition of the soft drugs takes place with a controllable rate in a predictable manner.

The present inventor has found five major classes of soft drugs. One of the most useful classes was termed the "inactive metabolite" approach which can be advantageously employed to design especially valuable "soft drugs". This approach starts with a known inactive metabolite of a drug or a drug class; followed by modifying the metabolite to resemble structurally (isosteric and/or isoelectronic) the active drug (i.e., activation); and designing the metabolism of the activated species to lead to the starting inactive metabolite after achieving the desired therapeutic role, without the formation of toxic intermediates (i.e., predictable metabolism). The "inactive metabolite" approach further allows controlling the rate of metabolism and pharmacokinetic properties by molecular manipulation in the activation stage. Also, if no useful inactive metabolite is known, one can be designed by the introduction of transporting groups in noncritical structural parts.

SUMMARY OF THE INVENTION

The present inventor has now applied his inactive metabolite approach to the case of the natural and synthetic glucocorticosteroids and has designed the soft steroidal anti-inflammatory agents of the present invention, beginning with the known inactive natural metabolites of the glucocorticosteroids. Thus, for example, in the case of hydrocortisone, one of its major, inactive metabolites, cortienic acid, i.e., 11$\beta$,17$\alpha$-dihydroxyandrost-4-en-3-one-17$\beta$-carboxylic acid, has been used as a starting point and activated by the introduction of suitable non-toxic 17$\alpha$- and 17$\beta$-substituents, which activated derivatives will cleave in vivo, after accomplishment of their therapeutic role, to the starting inactive metabolite and other nontoxic moieties.

In accord with the foregoing, the present invention provides novel soft steroids having anti-inflammatory activity, said steriods having the structural formula

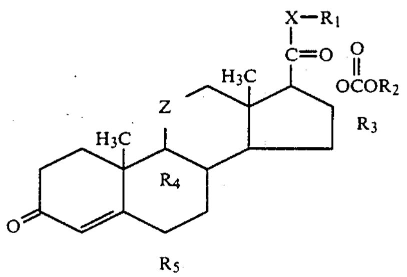

(I)

wherein:

$R_1$ is $C_1$–$C_{10}$ alkyl; $C_2$–$C_{10}$ (monohydroxy or polyhydroxy)alkyl; $C_1$–$C_{10}$ (monohalo or polyhalo)alkyl; or $-CH_2COOR_6$ wherein $R_6$ is unsubstituted or substituted $C_1$–$C_{10}$ alkyl, $C_3$–$C_8$ cycloalkyl, $C_3$–$C_8$ cycloalkenyl or $C_2$–$C_{10}$ alkenyl, the substituents being selected from the group consisting of halo, lower alkoxy, lower alkylthio, lower alkylsulfinyl, lower alkylsulfonyl, $$-NH\overset{O}{\overset{\|}{C}}-(C_1-C_{10}\text{ alkyl}) \text{ and } -O\overset{O}{\overset{\|}{C}}-(C_1-C_{10}\text{ alkyl}),$$

or $R_6$ is unsubstituted or substituted phenyl or benzyl, the substituents being selected from the group consisting of lower alkyl, lower alkoxy, halo, carbamoyl, lower alkoxycarbonyl, lower alkanoyloxy, lower haloalkyl, mono(lower alkyl)amino, di(lower alkyl)amino, mono(lower alkyl)carbamoyl, di(lower alkyl)carbamoyl, lower alkylthio, lower alkylsulfinyl and lower alkylsulfonyl; or $R_1$ is $-CH_2CONR_7R_8$ wherein $R_7$ and $R_8$, which can be the same or different, are each hydrogen, lower alkyl, $C_3$-$C_8$ cycloalkyl, phenyl or benzyl, or $R_7$ and $R_8$ are combined such that $-NR_7R_8$ represents the residue of a saturated monocyclic secondary amine; or $R_1$ is unsubstituted or substituted phenyl or benzyl, the substituents being selected from the group of phenyl and benzyl substituents defined hereinabove with respect to $R_6$; or $R_1$ is $$-\underset{R_9}{\underset{|}{C}H}-Y\text{-(lower alkyl)}$$

wherein Y is —S—, —SO—, —$SO_2$— or —O— and $R_9$ is hydrogen, lower alkyl or phenyl, or $R_9$ and the lower alkyl group adjacent to Y are combined so that $R_1$ is a cyclic system of the type $$\begin{array}{c}-CH-Y\\ \quad|\qquad|\\ \text{alkylene}\end{array}$$

wherein Y is defined as above and the alkylene group contains 3 to 10 carbon atoms, of which at least 3 and no more than 6 are ring atoms; or $R_1$ is $$-\underset{R_{10}}{\underset{|}{C}H}-O\overset{O}{\overset{\|}{C}}R_6$$

wherein $R_6$ is defined as hereinabove and $R_{10}$ is hydrogen, lower alkyl, phenyl or haloalkyl;

$R_2$ is unsubstituted or substituted $C_1$-$C_{10}$ alkyl, $C_3$-$C_8$ cycloalkyl, $C_3$-$C_8$ cycloalkenyl or $C_2$-$C_{10}$ alkenyl, the substituents being selected from the group consisting of halo, lower alkoxy, lower alkylthio, lower alkylsulfinyl, lower alkylsulfonyl, $$-NH\overset{O}{\overset{\|}{C}}-(C_1-C_{10}\text{ alkyl}) \text{ and } -O\overset{O}{\overset{\|}{C}}-(C_1-C_{10}\text{ alkyl}),$$

or $R_2$ is unsubstituted or substituted phenyl or benzyl, the substituents being selected from the group consisting of lower alkyl, lower alkoxy, halo, carbamoyl, lower alkoxycarbonyl, lower alkanoyloxy, lower haloalkyl, mono(lower alkyl)amino, di(lower alkyl)amino, mono(lower alkyl)carbamoyl, di(lower alkyl)carbamoyl, lower alkylthio, lower alkylsulfinyl and lower alkylsulfonyl;

$R_3$ is hydrogen, $\alpha$-hydroxy, $\beta$-hydroxy, $\alpha$-methyl, $\beta$-methyl, $=CH_2$, or $\alpha$- or $$\beta\text{-}O\overset{O}{\overset{\|}{C}}OR_2$$

wherein $R_2$ is identical to $R_2$ as defined hereinabove;

$R_4$ is hydrogen, fluoro or chloro;

$R_5$ is hydrogen, fluoro, chloro or methyl;

X is —O— or —S—;

Z is carbonyl or $\beta$-hydroxymethylene;

and the dotted line in ring A indicates that the 1,2-linkage is saturated or unsaturated.

A group of preferred compounds of formula (I) consists of those wherein:

$R_1$ is $C_1$-$C_6$ alkyl; $C_1$-$C_6$ (monohalo or polyhalo)alkyl; $-CH_2COOR_6$ wherein $R_6$ is $C_1$-$C_6$ alkyl; $-CH_2-Y-(C_1$-$C_6$ alkyl) wherein Y is —S—, —SO—, —$SO_2$— or —O—; or $$-CH_2-O\overset{O}{\overset{\|}{C}}R_6'$$

wherein $R_6'$ is $C_1$-$C_6$ alkyl or phenyl;

$R_2$ is $C_1$-$C_6$ alkyl, $C_3$-$C_8$ cycloalkyl, phenyl, benzyl or $C_1$-$C_6$ (monohalo or polyhalo)alkyl;

$R_3$ is hydrogen, $\alpha$-hydroxy, $\alpha$-methyl, $\beta$-methyl or $$\alpha\text{-}O\overset{O}{\overset{\|}{C}}OR_2$$

wherein $R_2$ is identical to $R_2$ as defined hereinabove;

$R_4$ is hydrogen or fluoro;

$R_5$ is hydrogen or fluoro;

Z is $\beta$-hydroxymethylene;

and X and the dotted line in ring A are defined as hereinabove.

The invention further provides anti-inflammatory quaternary ammonium salts of selected compounds of formula (I), as discussed in further detail below. Novel intermediates to the compounds of formula (I), e.g., the corresponding compounds wherein $R_1$ is hydrogen, are provided also.

The soft steroids of formula (I) and quaternary ammonium salts thereof are extremely potent local anti-inflammatory agents; however, by virtue of the fact that their facile in vivo destruction leads only to the inactive steroidal metabolite, the present compounds have far less systemic activity than the known glucocorticosteroids from whose inactive metabolites they are derived. Indeed, many of the compounds of the present invention are entirely devoid of systemic activity. Such minimal— or non-existent— systemic activity means that the compounds of the present invention can be used in the local (e.g., topical) treatment of inflammatory conditions without the serious systemic side effects which attend use of the known glucocorticosteroids.

DETAILED DESCRIPTION OF THE INVENTION AND THE PREFERRED EMBODIMENTS

With respect to the various groups encompassed by the generic terms used here and throughout this specification, the following definitions and explanations are applicable:

The alkyl, alkenyl and alkylene groupings can be straight or branched-chain groups containing the aforementioned number of carbon atoms. Likewise, the alkyl portions of the alkoxy, alkylthio, alkylsulfinyl, alkylsulfonyl, alkoxycarbonyl, alkanoyloxy, haloalkyl, monoalkylamino, dialkylamino, monoalkylcarbamoyl and dialkylcarbamoyl groupings each can be straight or branched-chain. The term "lower" used in conjunction with any of those groupings or in conjunction with "alkyl" is intended to indicate that each alkyl portion therein can contain 1 to 8 carbon atoms.

Specific examples of alkyl radicals encompassed by formula (I), whether as specific values for $R_1$ or $R_2$, or as a portion of a $R_1$, $R_2$, or $R_3$ group, include methyl, ethyl, propyl, butyl, pentyl, hexyl, heptyl and octyl and their branched-chain isomers, as well as their straight and branched-chain higher homologues in the instances where "alkyl" can contain more than 8 carbon atoms. The alkenyl radicals can be exemplified by vinyl, propenyl and butenyl. Illustrative of the cycloalkyl and cycloalkenyl radicals are cyclopentyl, cyclohexyl, cyclopentenyl and cyclohexenyl. The alkylene moieties are typified by timethylene, tetramethylene and the like.

The alkoxy, alkylthio, alkylsulfinyl, alkylsulfonyl, alkoxycarbonyl, alkanoyloxy, monoalkylamino, dialkylamino, monoalkylcarbamoyl and dialkylcarbamoyl

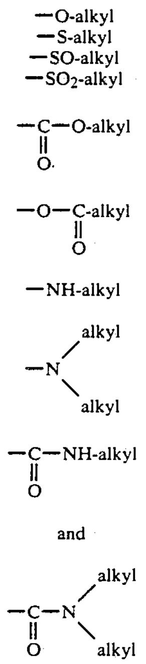

respectively, wherein alkyl is as hereinbefore defined and exemplified.

With respect to the structural variables encompassed by the group of preferred compounds of formula (I) identified hereinabove, the term "$C_1$–$C_6$ alkyl" is used to refer to a straight or branched-chain alkyl group having 1 to 6 carbon atoms, such as methyl, ethyl, n-propyl, isopropyl, n-butyl, isobutyl, sec-butyl, tert-butyl, n-pentyl, n-hexyl and the like. In addition, the term "$C_1$–$C_6$ (monohalo or polyhalo)alkyl" is used to refer to a straight or branched-chain alkyl group having 1 to 6 carbon atoms substituted with from 1 to 3 halogen atoms, the term "halogen" as used herein including a chlorine atom, a bromine atom, an iodine atom or a fluorine atom. Specific examples of the contemplated monohaloalkyl and polyhaloalkyl groups include chloromethyl, dichloromethyl, trichloromethyl, bromomethyl, fluoromethyl, difluoromethyl, trifluoromethyl, 1-fluoroethyl, 1-chloroethyl, 2-chloroethyl, 2,2,2-trichloroethyl, 2,2,2-trifluoroethyl, 1,2-dichloroethyl, 1-chloropropyl, 3-chloropropyl, 1-chlorobutyl, 1-chloropentyl, 1-chlorohexyl, 4-chlorobutyl and the like. Also, the term "$C_3$–$C_8$ cycloalkyl" is used to refer to a cycloalkyl radical having 3 to 8 carbon atoms, such as cyclopropyl, cyclobutyl, cyclopentyl, cyclohexyl, cycloheptyl and cyclooctyl.

When $R_1$ in formula (I) is $—CH_2CONR_7R_8$ wherein $—NR_7R_8$ represents the residue of a saturated monocyclic secondary amine, such monocycles preferably have 5 to 7 ring atoms optionally containing another hetero atom (—O—, —S— or —N—) in addition to the indicated nitrogen atom, and optionally bear one or more substituents such as phenyl, benzyl and methyl. Illustrative of residues of saturated monocyclic secondary amines which are encompassed by the $—NR_7R_8$ term are morpholino, 1-pyrrolidinyl, 4-benzyl-1-piperazinyl, perhydro-1,2,4-oxathiazin-4-yl, 1- or 4-piperazinyl, 4-methyl-1-piperazinyl, piperidino, hexamethyleneimino, 4-phenylpiperidino, 2-methyl-1-pyrazolidinyl, 1- or 2-pyrazolidinyl, 3-methyl-1-imidazolidinyl, 1-or 3-imidazolidinyl, 4-benzylpiperidino and 4-phenyl-1-piperazinyl.

Selected compounds of formula (I), i.e. compounds wherein $R_1$ is α-haloalkyl, readily form the corresponding soft quaternary ammonium salts which are likewise useful as soft anti-inflammatory agents. Thus, for example, the selected haloalkyl derivative of formula (I) can simply be reacted with a tertiary amine

or an unsaturated amine

to afford the corresponding quaternary ammonium salt. The reactants are generally used in approximately equimolecular proportions and the reaction is conducted in the presence of an inert solvent (e.g., ether, acetonitrile, $CH_2Cl_2$ or the like), at a temperature of from room temperature to the reflux temperature of the solvent, for approximately 2 to 24 hours. Alternatively, the reaction can be conducted in the absence of a solvent by mixing the two reactants together and maintaining them at room temperature or between 20° to 70° C. for 2 to 24 hours. In either case, the crystalline salt formed can be purified by crystallization from an ether-ethanol mixture, or the like.

The expression "unsaturated amine" used above denotes N-heterocyclic unsaturated systems having 3 to 10 members in the ring, and substituted derivatives thereof, where the unsaturation corresponds to the maximum number of non-cumulative double bonds, provided that the nitrogen atom contains no hydrogen atom as a substituent. The following examples will sufficiently illustrate the scope of the defined term:

1-Methylazirine 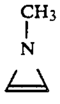

1-Methylpyrrole 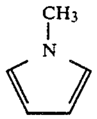

1-Methylimidazole 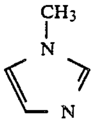

1-Methylpyrazole 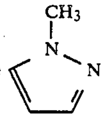

Pyridine 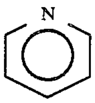

Pyrazine 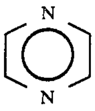

Pyrimidine 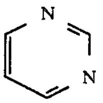

Pyridazine 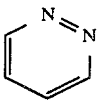

2-Methylisoindole 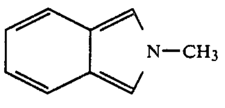

3<u>H</u>-indole 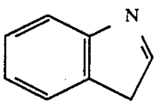

Quinoline 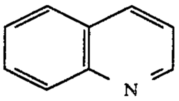

Isoquinoline 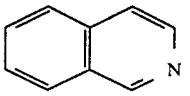

Phthalazine 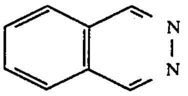

-continued

Quinoxaline 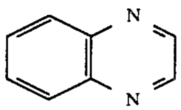

Quinazoline 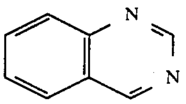

Phenazine 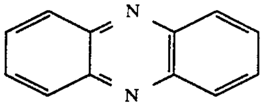

Isothiazole 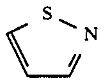

10-Methylphenothiazine 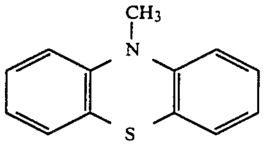

Isoxazole 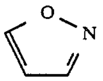

Furazan 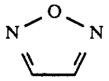

Substituted derivatives of the unsaturated amines include groups as shown above containing one or more alkyl, —COO(alkyl) or —OCO(alkyl) substituents.

With respect to the expression "tertiary amine", this expression denotes amines wherein the nitrogen atom has no hydrogen atoms attached thereto and which are not among the N-heterocyclic unsaturated systems encompassed by the expression "unsaturated amine" as defined above. Typically, the term "tertiary amine" includes trialkylamines, wherein the alkyl groups, which can be the same or different, each preferably contain 1 to 8 carbon atoms; trialkoxyamines wherein the alkoxy portions each contain 1 to 8 carbon atoms; tertiary saturated cyclic amines such as quinuclidine or substituted quinuclidine (e.g., 3-acetoxyquinuclidine); and N-substituted derivatives of secondary saturated cyclic amines [e.g., an N-substituted derivative or morpholine, pyrrolidine, imidazolidine, pyrazolidine, piperidine or piperazine, wherein the N-substituent can be a group such as ($C_1$–$C_8$) alkyl], optionally containing additional substituents such as methyl.

Preferred quaternary ammonium salts include those derived from 1,2-dimethylpyrrolidine, 3-acetoxyquinuclidine, 1-methylpyrrolidine, triethylamine and N-methylimidazole. Especially preferred are the quaternary ammonium salts derived from the reaction of the aforesaid amines with compounds of formula (I) wherein Z is $\beta$-hydroxymethylene and $R_1$ is chloromethyl, most especially when $R_2$ is lower alkyl.

While all of the compounds encompassed by formula (I) above essentially satisfy the objectives of the present invention, nevertheless certain groups of compounds remain preferred. A "first" group of preferred compounds of formula (I) has been set forth in the Summary of the Invention hereinabove.

Another preferred group of compounds consists of the compounds of formula (I) wherein Z, X, $R_1$ and $R_2$ are defined as hereinabove, and the remainder of the structural variations are identical to those of hydrocortisone (i.e. $R_3$, $R_4$ and $R_5$ are each a hydrogen atom and the 1,2-linkage is saturated) or of prednisolone (i.e., $R_3$, $R_4$ and $R_5$ are each a hydrogne atom and the 1,2-linkage is unsaturated), most especially when $R_1$ and $R_2$ are as defined with respect to the "first" group of preferred compounds set forth hereinabove.

Another preferred group of compounds consists of the 6α- and/or 9α-fluoro and 16α- or 16β-methyl congeners of the compounds indicated in the preceding paragraph. Within this group, the compounds wherein Z, X, $R_1$ and $R_2$ are defined as hereinabove and the remaining structural variables are identical to those of fludrocortisone, betamethasone and dexamethasone are particularly preferred, most especially when $R_1$ and $R_2$ are as defined with respect to the "first" group of preferred compounds set forth hereinabove. Other compounds of particular interest within this group are those wherein Z, X, $R_1$ and $R_2$ are defined as hereinabove and the remaining structural variables are identical to those of triamcinolone, flumethasone, fluprednisolone or paramethasone, particularly when $R_1$ and $R_2$ are as defined with respect to the "first" group of preferred compounds set forth hereinabove. Yet other interesting compounds are those wherein Z, X, $R_1$ and $R_2$ are defined as hereinabove, $R_3$ is

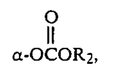

and the remaining structural variables are identical to those of triamcinolone, particularly when $R_1$ and $R_2$ are as defined with respect to the "first" group of preferred compounds set forth hereinabove.

In each of the groups of compounds indicated in the three preceding paragraphs, the compounds wherein X is oxygen are particularly preferred. Most especially preferred are the compounds encompassed by the groups indicated above wherein Z is β-hydroxymethylene, wherein X is oxygen, wherein $R_2$ is $C_1$-$C_6$ alkyl (particularly methyl, ethyl, propyl or isopropyl), and wherein $R_1$ is $C_1$-$C_6$ alkyl, $C_1$-$C_6$ (monohalo)alkyl (particularly chloromethyl) or $-CH_2-Y-(C_1-C_6$ alkyl) wherein Y is defined as hereinabove (particularly when the $C_1$-$C_6$ alkyl group is methyl).

The compounds of formula (I) can generally be prepared by known methods, the method of choice being dependent on the identity of the various substituents in the desired final product.

One generally useful method for the preparation of the compounds of formula (I) wherein Z is β-hydroxymethylene and X is oxygen utilizes steroidal starting materials of the formula

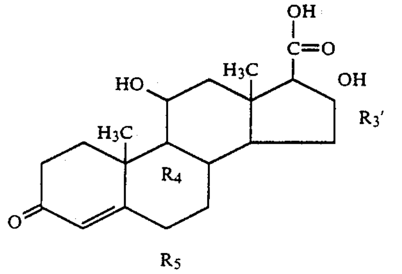

(II)

wherein $R_4$, $R_5$ and the dotted line in ring A are defined as before and $R_3'$ is hydrogen, α-methyl, β-methyl, α-OH, β-OH or $=CH_2$ (and which can be conveniently prepared by treatment of the corresponding 21-hydroxypregnenolones of the formula

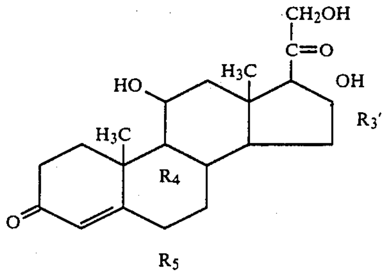

wherein $R_4$, $R_5$, $R_3'$ and the dotted line in ring A are defined as above with $NaIO_4$ in a suitable organic solvent at room or elevated temperature.) According to this process of the invention, a starting material of formula (II) is reacted with $R_2OCOCl$ or $R_2OCOBr$ (formed by reacting $R_2OH$ with $COCl_2$ or $COBr_2$, wherein $R_2$ is defined as above), under anhydrous conditions, in an appropriate inert organic solvent such as dichloromethane, chloroform or tetrahydrofuran, preferably in the presence of a suitable acid acceptor (e.g., triethylamine, pyridine, calcium carbonate or other appropriate base). Time and temperature are not critical factors; however, the reaction is conveniently carried out at a temperature between 0° C. and room temperature, for about 1 to 6 hours. The resultant novel 17β-carboxylic acid 17α-carbonate has the formula

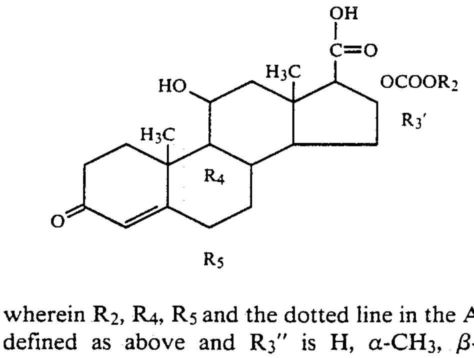

(III)

wherein $R_2$, $R_4$, $R_5$ and the dotted line in the A ring are defined as above and $R_3''$ is H, α-$CH_3$, β-$CH_3$, α-$OCOOR_2$, β-$OCOOR_2$ or $=CH_2$. When $R_3'$ in the starting material of formula (II) is α-OH or β-OH, sufficient $R_2OCOCl$ or $R_2OCOBr$ is generally employed to ensure formation of the carbonate grouping at the 16-position as well as at the 17-position [i.e., when $R_3'$ in formula (II) is OH, $R_3''$ in the resultant intermediate of formula (III) is α- or β-$OCOOR_2$].

Sometimes, when a compound of formula (I) wherein $R_2$ contains a sulfinyl or sulfonyl grouping is desired, such a grouping is not introduced via the $R_2OCOCl$/$R_2OCOBr$ reaction, but is prepared from the corresponding thio-containing $R_2$ derivative at a later stage in the synthetic scheme, as will be discussed in more detail below.

After the above-described introduction of the 17α-substituent, the resultant novel intermediate of formula (III) is converted to its corresponding metal salt of the formula

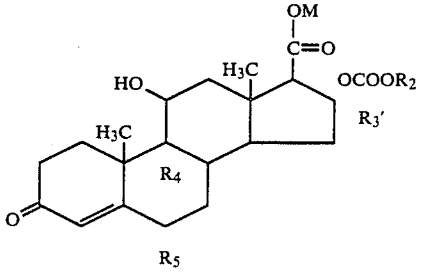

(IV)

wherein $R_2$, $R_3''$, $R_4$, $R_5$ and the dotted line in the ring A are defined as above, and M is a suitable metal, e.g. alkali metal (such as sodium or potassium), alkaline earth metal/2, or thallium or $NH_4^+$. The novel salt of formula (IV) is typically formed by reacting the steroid of formula (III) with a hydroxide (MOH) or alkoxide (MOR) in a appropriate organic solvent, such as ethyl ether or tetrahydrofuran, at a temperature of 0° C. to room temperature, for 0.5 to 4 hours. Then, the salt of formula (IV) is reacted with a compound of the formula $R_1$-W wherein $R_1$ is defined as hereinabove and W is halogen, to afford the desired final product of formula (I). This step of the reaction sequence can be conveniently conducted at room temperature for about 1 to 24 hours, or at the boiling of the solvent (i.e. acetonitrile, THF, etc.) When it is desired to introduce a halo-substituted $R_1$ grouping into the steroid, e.g., when a compound of formula (I) wherein $R_1$ is chloromethyl is desired, it has been found that the reaction proceeds well using hexamethylphosphoramide as the solvent at lower temperatures (0°-10° C.) and employing a $R_1$-W reactant wherein W is iodine (e.g., iodochloromethane). When a non-halogen containing $R_1$ grouping is desired (e.g., $R_1$=alkyl or $—CH_2COOR_6$ where $R_6$ is alkyl, etc.), no such restrictions need by placed on the $R_1$-W reactant or on the solvent; thus, W can be any halogen, preferably chloro or bromo, and the usual organic solvents such as dimethylformamide, dichlormethane, acetonitrile, tetrahydrofuran or chloroform can, if desired, be used instead of hexamethylphosphoramide. When a compound of formula (I) wherein $R_1$ contains a sulfinyl or sulfonyl grouping is desired, such a grouping is not generally introduced via the $R_1$-W reaction, but is subsequently prepared from the corresponding thio steroid, as described below.

The compounds of formula (I) wherein $R_1$ (or $R_2$) is a sulfinyl- or sulfonyl-containing grouping can be prepared by oxidation of the corresponding thio steroids. Thus, for example, a compound of formula (I) wherein $R_1$ is

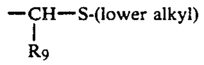

[wherein $R_9$ is H, lower alkyl, or combined with the lower alkyl group adjacent to S to form a cyclic system, as described hereinabove] can be reacted wtih 1 equivalent of m-chloroperoxybenzoic acid at 0°-25° C. for 1 to 24 hours, in a suitable solvent such as chloroform, to afford the corresponding compound of formula (I) wherein $R_1$ is

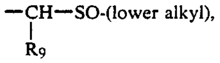

or with 2 equivalents of m-chloroperoxybenzoic acid to afford the corresponding compound of formula (I) wherein $R_1$ is

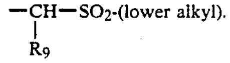

This type of reaction can also be utililzed to prepare compounds of formula (I) wherein $R_1$ is $—CH_2COOR_6$ wherein $R_6$ is substituted alkyl, cycloalkyl, cycloalkenyl, alkenyl, phenyl, or benzyl, wherein the substituent is lower alkylsulfinyl or lower alkylsulfonyl, from the corresponding lower alkylthio-substituted formula (I) steroids; to prepare compounds of formula (I) wherein $R_1$ is lower alkylsulfinyl- or alkylsulfonyl-substituted phenyl or benzyl from the corresponding lower alkylthio-substituted formula (I) steroids; and to prepare compounds of formula (I) wherein $R_2$ is substituted alkyl, cycloalkyl, cycloalkenyl, alkenyl, phenyl or benzyl wherein the substituent is lower alkylsulfinyl or lower alkylsulfonyl, from the corresponding lower alkylthio-substituted formula (I) steroids.

When the compounds of formula (I) wherein $R_3$ is α- or β-hydroxy are desired, same can be prepared by partial acid hydrolysis of the corresponding compounds of formula (I) wherein $R_3$ is α- or β-$OCOOR_2$, in a suitable solvent medium. Use of a mild reagent, e.g., oxalic acid in methanol, is desirable. Alternatively, hydrolysis of the 16-carbonate to the 16-hydroxy compound could be carried out at an earlier stage in any synthetic scheme described herein after the introduction of the 16,17-carbonate groupings, e.g., selective hydrolysis of an intermediate of formula (III) having 16 and 17 carbonate groupings to the corresponding 16-hydroxy 17-carbonate, followed by conversion to the corresponding compound of formula (I) as described supra.

Another process for the preparation of the compounds of formula (I) wherein Z is β-hydroxymethylene and X is oxygen utilizes the same 17α-hydroxy-17β-carboxylic acid starting materials of formula (II) as are employed in the synthetic scheme described supra, but involves formation of the 17β-$COOR_1$ grouping prior to, rather than after, introduction of the 17α-$OCOOR_2$ substituent. Essentially, the same non-steroidal reactants, reaction conditions, etc., as described above are used for the introduction of each group. Thus, the starting material of formula (II) is first reacted with MOH or MOR to form the corresponding intermediate of the formula

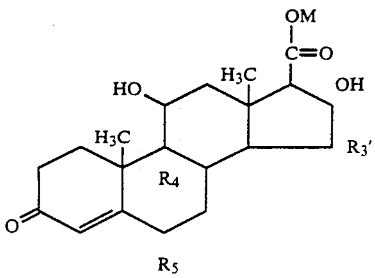

(V)

wherein $R_3'$, $R_4$, $R_5$ and M and the dotted line in ring A are defined as above, which is then reacted with $R_1W$ wherein $R_1$ and W are defined as above, to afford the corresponding 17β-carboxylate of the formula

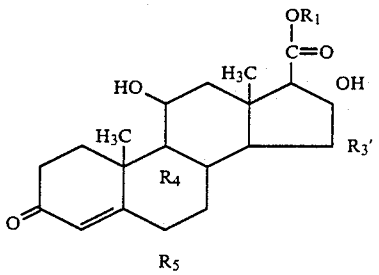

(VI)

wherein $R_1$, $R_3'$, $R_4$, $R_5$ and the dotted line in ring A are defined as above, which is in turn reacted with $R_2OCOCl$ or $R_2OCOBr$ wherein $R_2$ is defined as above, to afford the corresponding 17α-carbonate of formula (I). The various parameters of the process of converting (II) to (V) are the same as those discussed in detail above with respect to the conversion of (III) to (IV). Likewise, the process parameters for converting (V) to (VI) parallel those detailed above with respect to converting (IV) to (I). Similarly, the process parameters for converting (VI) to (I) are basically the same as those given above for the conversion of (II) to (III). Thus, again, when the starting material contains a 16-hydroxy group, the 16,17-dicarbonate of formula (I) will be formed which can then be selectively hydrolyzed, if desired, to the corresponding 16-hydroxy-17-carbonate of formula (I). And, again, the compounds of formula (I) in which $R_1$ or $R_2$ is a sulfinyl- or sulfonyl-containing grouping can be conveniently prepared by oxidation of the corresponding thio-containing compounds of formula (I) as detailed hereinabove. Alternatively, the compounds of formula (I) wherein $R_1$ is $$-\underset{R_9}{\underset{|}{CH}}-SO\text{-(lower alkyl) or }-\underset{R_9}{\underset{|}{CH}}-SO_2\text{-(lower alkyl)]}$$

can be prepared by oxidation, preferably with m-chloroperoxybenzoic acid, of the corresponding compounds of formula (VI) in which $R_1$ is a thio-containing group, followed by introduction of the 17α-$OCOOR_2$ substituent to the resultant sulfinyl or sulfonyl compound.

Another possible process for the preparation of the compounds of the present invention, which can be used to prepare compounds of formula (I) wherein Z is β-hydroxymethylene and X is oxygen or sulfur, utilizes the 17β-carboxylic acid 17α-carbonate intermediates of formula (III) above. According to this process, an intermediate of formula (III) is successively treated, first with a mild acyl chloride forming agent, e.g. such as diethylchlorophosphate or oxalyl chloride, to form the corresponding novel acid chloride of the formula

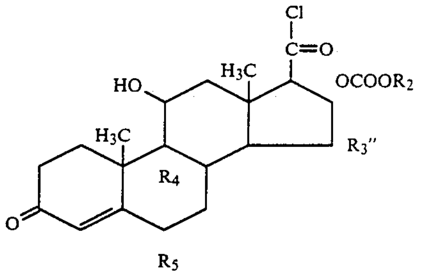

(VIII)

wherein $R_2$, $R_3''$, $R_4$, $R_5$ and the dotted line in ring A are defined as above, and then with $R_1XM'$ wherein $R_1$ and X are defined as before, and M' is hydrogen or M (M is defined as above), in an inert solvent (e.g., $CHCl_3$, THF, acetonitrile or DMF), at a temperature between about 0° C. and the boiling point of the solvent, for 1 to 6 hours, to afford the corresponding compound of formula (I). When using a compound of the formula $R_1XM'$ wherein M' is hydrogen, an acid scavenger such as triethylamine is preferably present in the reaction system. The two steps of this process can be very conveniently run in the same solvent, without isolating the acid chloride of formula (VIII) formed in the first step. This process is of particular value when a compound of formula (I) wherein X is S is desired.

Yet another desirable process for the preparation of the compounds of formula (I) wherein Z is β-hydroxymethylene and X is oxygen utilizes the 17α-hydroxy-17β-carboxylates of formula (VI) above. According to this process, an intermediate of formula (VI) is reacted with phosgene, in a suitable organic solvent (e.g., toluene, benzene, $CH_2Cl_2$ or acetonitrile) at a low temperature (−20° C. to room temperature, e.g., 0° C.), for about 2 hours (or until the reaction is complete). Evaporation to remove solvent and excess phuosgene affords the desired novel 17α-chlorocarbonyloxy-17β-carboxylate intermediate of the formula

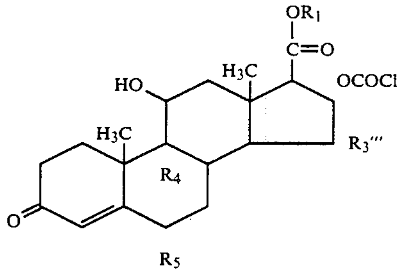

(VII)

wherein $R_1$, $R_4$, $R_5$ and the dotted line in ring A are defined as above, $R_3'''$ is hdyrogen, α-methyl, β-methyl, α-OCOCl, β-OCOCl or $=CH_2$. When $R_3'$ in the starting material of formula (VI) is hydroxy, sufficient phosgene is generally employed to ensure formation of the chlorocarbonyloxy grouping at the 16-position as well as the 17-position [i.e., when $R_3'$ in formula (VI) is α-OH or β-OH, $R_3'''$ in the resultant intermediate of formula (VII) is α- or β-OCOCl]. The intermediate of formula (VII) is then reacted with a compound of the formula $R_2OM'$ wherein $R_2$ and M' are defined as above, in an inert solvent, preferably in the presence of an acid scavenger (e.g. triethylamine), to afford the corresponding compound of formula (I). When $R_2OM'$ is an alcohol of the formula $R_2OH$, the reaction is conducted under the same conditions as in the reaction for conversion of compound (II) to compound (III). On the other hand, if a compound of the formula $R_2OM$ is employed as $R_2OM'$, the reaction conditions are described as above for conversion of compound (VIII) to compound (I). When $R_3'''$ in th formula (VII) is OCOCl, sufficient $R_2OM'$ is generally utilized to ensure conversion of both the 16- and 17α-substituents to $OCOOR_2$ groupings in the final product. And, again, the 16-hydroxy and the sulfinyl- and sulfonyl- containing compounds of formula (I) are most conveniently formed as a final step in the synthetic scheme.

As a variation of the process described immediately above, a steroidal 17α-hydroxy-17β-carboxylic acid starting material of formula (II) can be reacted with phosgene as described above, to afford the 17α-chlorocarbonyloxy-17β-carboxylic acid intermediate of the formula

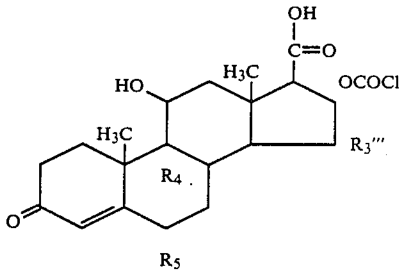
(X)

wherein $R_3'''$, $R_4$, $R_5$ and the dotted line in ring A are defined as above, which can then be reacted with $R_2OM'$ as described supra, to afford the corresponding compound of formula, (III) above. The novel intermediate can then be converted to a corresponding compound of formula (I) as described supra. Once again, the 16-hydroxy and the sulfinyl and sulfonyl derivatives are best prepared as a final step.

Still another process for the preparation of the compounds of formula (I) wherein Z is β-hydroxymethylene and X is oxygen utilizes the 17α-hydroxy-17β-carboxylates of formula (VI) above. In accord with this method, an intermediate of formula (VI) is reacted with an excess amount of a carbonate of the formula

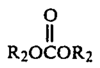

(which can be conveniently prepared by reacting phosgene with 2 equivalents of $R_2OH$) in the presence of an acid catalyst, to afford the corresponding compound of formula (I). Depending on the nature of the $R_2$ grouping, the

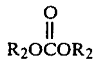

reactant can also act as the solvent at the boiling point of the carbonate reactant, or at the boiling point of the corresponding $R_2OH$ (which can conveniently be removed in this way from the reaction mixture, driving the reaction to completion), or the reactants can be combined in an appropriate inert organic solvent (e.g., an aromatic such as benzene or toluene, or a halogenated hydrocarbon such as dichloromethane or chloroform). And, again, the 16-hydroxy and the sulfinyl and sulfonyl compounds of formula (I) can conveniently be prepared as a final step in the process, although the intermediate of formula (VI) in which $R_1$ contains a sulfur atom could be first oxidized, and the resultant sulfinyl or sulfonyl compound of formula (VI) then reacted with

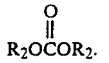

Other procedures for the preparation of selected compounds of formula (I) will be apparent to those skilled in the art. By way of example, a compound of formula (I) wherein $R_1$or $R_2$ is halo-substituted can be subjected to a halogen exchange reaction in order to replace the halogen with a different halogen according to the order of reactivity Cl<Br<I. For example, reacting a chloroalkyl 17β-carboxylate of formula (I) with an alkali metal iodide, e.g., sodium iodide, will afford the corresponding iodoalkyl 17β-carboxylate. Similarly, a bromide salt (e.g., lithium bromide) can be reacted with a chloroalkyl 17β-carboxylate to give the corresponding bromoalkyl 17β-carboxylate. A suitable solvent for either reaction may be selected from the group consisting of hexamethylphosphoramide, acetone, ethanol, methyl ethyl ketone, dimethylacetamide, dimethylformamide and acetonitrile.

In like manner, a halogen exchange reaction based on relative solubilities can be used to convert a chloroalkyl 17β-carboxylate or an iodoalkyl 17β-carboxylate of formula (I) to the corresponding fluoroalkyl derivative. Silver fluoride can be employed in this reaction, which is conducted in a suitable organic solvent (e.g., aceytonitrile), and which is especially useful in the preparation of the compounds in which $R_1$ is fluoromethyl or fluoroethyl.

The 21-hydroxypregnenolones from which the steroidal starting materials of formula (II) are prepared can be obtained commercially or prepared by known methods. Likewise, the non-steroidal starting materials used in the various processes discussed above are commercially available or can be prepared by known chemical procedures.

Also, a starting material of formula (II) above can be reacted with a compound of the formula $R_2OCOCl$ or $R_2OCOBr$ wherein $R_2$ is as defined above, to afford an intermediate of the formula

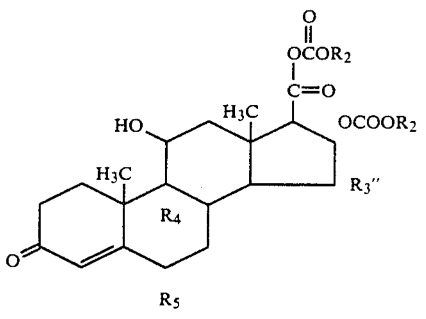
(XI)

wherein $R_2$, $R_3''$, $R_4$, $R_5$ and the dotted line in ring A are defined as above, which can be converted to the corresponding intermediate of formula (III) above by partial hydrolysis, with or without isolation of the compound of formula (XI). This reaction of a starting material of formula (II) with $R_2OCOCl$ or $R_2OCOBr$ can be carried out under the same conditions as the reaction of a compound of formula (II) with $R_2OCOCl$ or $R_2OCOBr$ as described hereinabove, except that $R_2OCOCl$ or $R_2OCOBr$ is used in an amount of 2 moles or more to one mole of the compound of the formula (II). The partial hydrolysis of the resultant compound of the formula (XI) can be carried out in an inert solvent in the presence of a catalyst. Examples of suitable catalysts include tertiary alkyl amines such as triethylamine, trimethylamine or the like; aromatic amines such as pyridine, 4,4-dimethylaminopyridine, quinoline or the like; secondary alkyl amines such as diethylamine, dimethylamine or the like; and inorganic bases such as sodium hydroxide, potassium hydroxide, potassium bicarbonate, or the like. Preferably, pyridine and potassium bicarbonate are employed. Examples of suitable inert solvents for use in the hydrolysis include water; lower alcohols such as ethanol, methanol or the like; ethers suchy as dimethyl ether, diethyl ether, dimethoxyethane, dioxane, tetrahydrofuran, or the like; halogenated hydrocarbons such as dichloromethane, chloroform or the like; tertiary amines such as pyridine, triethylamine or the like; or a mixture of two or more of the solvents mentioned above. The reaction is usually carried out a temperature of from about 0° to 100° C., preferably at room temperature to 50° C., for 1 to 48 hours, preferably for 2 to 5 hours.

In yet another aspect, the present invention provides novel compounds of the formula

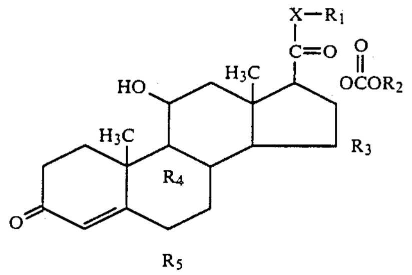

(IX)

wherein $R_1$, $R_2$, $R_3$, $R_4$, $R_5$, X and the dotted line in ring A are as defined with respect to formula (I) above. The 11-keto compounds of formula (IX) can be prepared by the procedures described hereinabove for the preparation of the corresponding 11β-hydroxy compounds of formula (I). Thus, a starting material corresponding to formula (II) but having an 11-keto group is reacted with $R_2OCOCl$ or $R_2OCOBr$, to afford the corresponding novel intermediate corresponding to formula (III) but having an 11-keto group; that intermediate is then converted to its metal salt, which corresponds to formula (IV) except for the presence of an 11-keto instead of an 11β-hydroxy group; and the metal salt is then reacted with $R_1W$ to afford the corresponding compound of formula (IX). All reaction conditions are as previously described with respect to the corresponding processes for preparing the corresponding compounds of formula (I). Also, the preparation of the compounds of formula (IX) wherein $R_1$ is a sulfinyl- or sulfonyl- containing grouping or wherein $R_3$ is hydroxy generally proceeds as a final step in the synthetic scheme in a manner analogous to that used for the corresponding compounds of formula (I). Further, all of the above-described alternative processes for the preparation of the compounds of formula (I) are equally applicable to the preparation of the compounds of formula (IX) by simply substituting the 11-oxo starting material for the corresponding 11β-hydroxy steroids used therein, e.g., replacing the 11-hydroxy group in formulas (V), (VI), (VII), (VIII), (X) and (XI) with an 11-oxo group and otherewise proceeding as described hereinabove for the reactions (II)→(V)→(VI)→(I); (III)→(VIII)→(I); (VI)→(VII)→(I); (II)→(X)→(I); (VI)→(I), etc.

Also, the compounds of formula (IX) can be prepared by reacting the corresponding compounds of formula (I) with an oxidizing agent. The oxidation of a compound of formula (I) in order to convert it into the corresponding compound of formula (IX) is usually carried out by using an oxidizing agent in an appropriate solvent. The solvent may be any conventional solvent, for example, water, and organic acid (e.g. formic acid, acetic acid, trifluoroacetic acid), an alcohol (e.g. methanol, ethanol), a halogenated hydrocarbon (e.g. chloroform, dichloromethane), or the like. This oxidizing agent may also be any conventional agent which is effective for oxidizing a hydroxy group to a carbonyl group, for example, pyridinium chlorochromate, chromium trioxide in pyridine, hydrogen peroxide, dichromic acid, dichromates (e.g. sodium dichromate, potassium dichromate), permanganic acid, permanganates (e.g. sodium permanganate, potassium permanganate), or the like. The oxidizing agent is usually used in an amount of 1 mole or more, preferably 1 to 3 mole, per mole of the compound of formula (I). The reaction is usually carried out at a temperature of 0° to 40° C., preferably at around room temperature, for about 6 to 30 hours.

The novel compounds of formula (IX) are useful as soft steroidal anti-inflammatory agents and also in vivo or in vitro precursors of the corresponding 11β-hydroxy compounds. Thus, the compounds of formula (IX) can be reduced in vitro to afford the corresponding compounds of formula (I), using a reducing agent known to be capable of reducing the 11-oxo group to an a 11β-hydroxy group without modifying the remainder of the steroidal starting material. Typically, microbiological reduction is advantageous for carrying out the desired conversion, although chemical reduction also is possible. Further, the compounds of formula (IX) may be formulated into appropriate dosage forms (e.g., retention enemas) for the treatment of conditions such as ulcerative colitis. In such dosage forms, it is thought that the compounds of formula (IX) are microbiologically reduced by bacteria in the body (e.g. in the colon) to the highly active 11β-hydroxy steroids, which elicit the desired anti-inflammatory response.

The preferred compounds of formula (IX) are those which are precursors of the preferred compounds of formula (I) wherein Z is β-hydroxymethylene, namely corresponding 11-keto compounds of formula (IX). As especially preferred group of compounds of formula (IX) consists of those wherein X, $R_1$ and $R_2$ are defined as above with respect to formula (I) and the remaining structural variations are identical to those of cortisone (i.e. $R_3$, $R_4$ and $R_5$ are each a hydrogen atom and the 1,2-linkage is saturated), of prednisone (i.e. $R_3$, $R_4$ and $R_5$ are each hydrogen and the 1,2-linkage is unsaturated), or of the 6α- and/or 9α-fluoro and the 16α- or 16β-methyl congeners thereof, particularly when $R_1$ and $R_2$ are as defined with respect to the "first" group of preferred compounds set forth hereinabove. Most especially preferred of these derivatives are those wherein X is oxygen, $R_2$ is $C_1$-$C_6$ alkyl and $R_1$ is $C_1$-$C_6$ alkyl, $C_1$-$C_6$ (monohalo)alkyl [particularly chloromethyl] or $-CH_2-Y-(C_1-C_6$ alkyl) [particularly $-CH_2-Y-CH_3$].

The results of various activity studies of representative species of the invention, discussed in detail below, clearly indicate the potent anti-inflammatory activity and the minimal systemic activity/toxicity of the soft steroids of formula (I). In view of this desirable separation of local and systemic activities, the compounds of the invention can be used in the treatment of topical or other localized inflammatory conditions without causing the serious systemic side effects typically exhibited by the known natural and synthetic glucocorticosteroids such as cortisone, hydrocortisone, hydrocortisone 17α-butyrate, betamethasone 17-valerate, triamcinolone, betamethasone dipropionate and the like.

THYMUS INVOLUTION TEST

The test animals were female Sprague/Dawley rats weighing approximately 40–45 grams each. One side of each ear of each rat was treated with a total of 25 microliters of a solution (ethanol/isopropyl myristate or acetone/isopropyl myristate, 90/10) containing the amount of test compound indicated below. Animals which were treated identically, save for omission of the test compound, served as controls. After 24 hours, all rats were sacrificed and weighed, and their thymi were removed and weighed. The results are tabulated in Table I below, the weights of the thymi being expressed as mg/100 g of rat.

TABLE I

Effect of topically administered soft steroids and reference steroids on thymus weight in rats.

| Test Compound | Amount of Test Compound Applied (μmol) | Number of Rats | $\frac{\text{mg Thymus}}{\text{100 g Rat}}$ ± SD | Total Weight per Rat (g) Starting | Final | % Gain ± SD |
|---|---|---|---|---|---|---|
| None (Control) | — | 8 | 364 ± 29 | 48.44 | 61.42 | 27 ± 6 |
| Hydrocortisone | 0.75 | 8 | 274 ± 45 | 49.44 | 61.15 | 24 ± 7 |
| Chloromethyl 11β-hydroxy-17α-methoxycarbonyl-oxyandrost-4-en-3-one-17β-carboxy-late | 0.75 | 8 | 347 ± 31 | 48.06 | 62.10 | 29 ± 5 |
| Chloromethyl 17α-ethoxycar-bonyloxy-11β-hydroxyandrost-4-en-3-one-17β-carboxylate | 0.75 | 7 | 309 ± 24 | 45.57 | 60.60 | 33 ± 6 |

The change in weight in the thymi is a measure of systemic activity and hence of toxicity. The lower the weight of the thymi, the greater the systemic activity. As can be seen from the above data, even hydrocortisone, the natural glucocorticoid, causes a significant decrease in thymus weight compared to the control. The decreases caused by equal doses of representative species of the invention are much less significant, indicating those compounds have much less systemic activity than hydrocortisone.

BLANCHING STUDIES

MeKenzie-type human blanching studies were undertaken to study the blanching effects of a representative test compound of the invention, chloromethyl 17α-ethoxycarbonyloxy-11β-hydroxyandrost-4-en-3-one-17β-carboxylate. The ability of a compound to cause blanching in humans has been found to correlate closely with its anti-inflammatory activity.

The test compound was dissolved in ethanol/isopropyl myristate (90/10 or 70/30) at 0.03, 0.01, 0.003, 0.001 and 0.0003M concentrations. 50 Microliter aliquots of each solution were applied to separate gauze portions of a bandage of the type commonly used for allergy testing and the bandage was applied to the forearm. After 6 hours of occlusion, the bandage was removed. After 1 to 5 hours after removal of the bandage, blanching was observed even at the lowest concentrations of test compound.

When hydrocortisone was tested according to the above procedure comparing it directly to the test compound, blanching was not observed at concentrations of hydrocortisone below 0.03M. Further, it was noted that 0.03M hydrocortisone caused approximately the same degree of blanching as that resulting from use of 0.001M chloromethyl 17α-ethoxycarbonyloxy-11β-hydroxyandrost-4-en-3-one-17β-carboxylate.

EAR EDEMA TEST

The test animals were Sprague/Dawley rats weighing approximately 150 grams each. In treatment groups, selected amounts of the test compound were dissolved in acetone containing 5% croton oil and 50 microliters of the solution were applied to the inner surface of the right ear of the rats. A control group was identically treated with vehicle only, i.e. 5% croton oil in acetone. Six hours after croton oil challenge, a constant region of each ear was removed by dissection under anesthesia. Then, 48 hours after steroid treatment, the animals were sacrificed and the thymi and adrenals were removed and weighed. The test results showing the inhibitory effect of topically applied steroids on the ear swelling induced by croton oil are summarized in Table II below.

TABLE II

Effect of topically applied soft steroid and reference steroids on ear swelling induced by croton oil.

| Test Compound | Dose[a] mg/kg | Number of Test Animals | Ear Weight (mg)[b] Inflamed Ear | Untreated Ear | % Increase | % Inhibition | Relative Organ Weight (mg/100 g body wt.) Thymus | Adrenals |
|---|---|---|---|---|---|---|---|---|
| None (Control) | | 5 | 75.2 ± 4.5 | 46.6 ± 1.4 | 61.4 ± 8.9 | | 333 ± 15 | 23.3 ± 1.7 |
| Chloromethyl 17α-ethoxycarbonyloxy- | 0.3 | 5 | 62.2 ± 3.0* | 50.8 ± 2.4 | 23.3 ± 7.2* | 62.1 | 290 ± 25 | 26.0 ± 2.5 |
| 11β-hydroxyandrost-4-en-3-one-17β- | 1 | 5 | 55.0 ± 2.6** | 48.4 ± 1.0 | 14.0 ± 6.5** | 77.2 | 293 ± 21 | 18.7 ± 1.4 |
| carboxylate | 3 | 5 | 52.6 ± 1.8** | 51.6 ± 3.2 | 3.7 ± 8.1** | 94.0 | 288 ± 21 | 20.3 ± 0.8 |
| Hydrocortisone 17-butyrate | 1 | 5 | 50.0 ± 2.3** | 52.0 ± 2.5 | −3.6 ± 3.5** | 106.0 | 303 ± 21 | 20.2 ± 0.7 |
| Betamethasone 17-valerate | 1 | 5 | 55.4 ± 1.2* | 50.4 ± 2.0 | 10.9 ± 6.3** | 82.2 | 267 ± 19* | 18.9 ± 1.9 |

[a]calculated values based on application of 50 μl of steroid solution.
[b]50 μl of 5% croton oil/acetone and drugs in 5% croton oil/acetone were applied to the right ear. Ear weight was measured 6 hr after topical application.
*$p < 0.05$; **$p < 0.01$: Significant difference from control.

As can be seen from Table II above, the representative species of the present invention, namely chloromethyl 17α-ethoxycarbonyloxy-11β-hydroxyandrost-4-en-3-one-17β-carboxylate, substantially inhibited the swelling (and consequent increased weight) of the ear caused by the croton oil, i.e., the compound exhibited substantial anti-inflammatory activity. On the other hand, in contrast to the effect caused by betametasone 17-valerate, the representative compound of the invention did not significantly decrease the thymus weight as compared to the control, i.e., it did not show a significant degree of systemic activity.

GRANULOMA FORMATION TEST

The test compound was dissolved in acetone and aliquots of varying concentrations were injected into cotton pellets. The pellets were dried and then one pellet was implanted beneath the skin of each test rat. Six days later, the animals were sacrificed and the granulation tissue (granuloma) which formed in and around the implanted pellet was removed, dried and weighed. In addition, the thymi and adrenals were removed and weighed. The ability of a compound to inhibit granuloma formulation in this test is a direct indication of local anti-inflammatory activity; thus, the lower the weight of granulation tissue, the better the anti-inflammatory activity. On the other hand, a significant decrease in thymus weight is indicative of significant systemic activity; conversely, when a test compound does not significantly decrease thymus weight as compared to the control, such is indicative of a lack of (or very minimal) systemic side effects.

The results are tabulated in Tables III, IV and V-a and V-b below.

TABLE III

Effect of locally administered soft steroids and reference steroids on body weight, thymus weight and granulation tissue formation caused by implantation of cotton pellets in rats.

| Test Compound | Dose (mg/pellet) | Number of Test Animals | Body wt. gain (g) | Granulation tissue Dry wt. (mg/100 g body wt.) | Inhibition (%) | Relative organ weight mg/100 g body wt. (Decrease %) Thymus | Adrenals |
|---|---|---|---|---|---|---|---|
| None (Control) | | 10 | 40.5 ± 0.8 | 43.7 ± 4.2 | | 326 ± 22 | 23.7 ± 1.1 |
| Chloromethyl 17α-ethoxycarbonyloxy- | 0.1 | 8 | 36.0 ± 2.8 | 34.7 ± 4.3 | 20.6 | 282 ± 13 (13.5) | 22.9 ± 2.6 (3.4) |
| 11β-hydroxyandrost-4-en-3-one-17β-carboxylate | 0.3 | 8 | 33.0 ± 1.3*** | 25.3 ± 2.3** | 42.1 | 298 ± 16 (8.6) | 22.8 ± 1.0 (3.8) |
| | 1 | 8 | 32.8 ± 0.9*** | 14.0 ± 1.8*** | 68.0 | 304 ± 10 (6.7) | 21.8 ± 1.3 (8.0) |
| | 3 | 7 | 30.7 ± 1.5*** | 18.7 ± 2.3*** | 57.2 | 278 ± 21 (14.7) | 19.6 ± 1.1* (17.3) |
| Chloromethyl 11β-hydroxy-17α-methoxycarbonyloxyandrost-4-en-3-one-17β-carboxylate | 1 | 7 | 33.4 ± 1.3*** | 24.6 ± 2.6** | 43.7 | 218 ± 15** (33.1) | 19.1 ± 1.1** (19.4) |
| Hydrocortisone 17-butyrate | 1 | 8 | 33.4 ± 1.4*** | 32.2 ± 5.0 | 26.3 | 73 ± 5*** (77.6) | 27.1 ± 1.4 (−14.3) |
| | 3 | 8 | 15.9 ± 1.4*** | 21.6 ± 2.2** | 50.6 | 47 ± 3*** (85.6) | 16.5 ± 1.2*** (30.4) |
| | 10 | 8 | 4.9 ± 1.0*** | 29.2 ± 3.1* | 33.2 | 32 ± 3*** (90.2) | 16.8 ± 1.2*** (29.1) |
| Betamethasone 17-valerate | 1 | 8 | 16.6 ± 1.9*** | 35.4 ± 7.3 | 19.0 | 47 ± 2*** (85.6) | 15.5 ± 1.3*** (34.6) |
| | 3 | 8 | 14.9 ± 1.7*** | 31.6 ± 2.1* | 27.7 | 38 ± 3*** (88.3) | 13.6 ± 0.9*** (42.6) |
| | 10 | 8 | 17.0 ± 2.1*** | 40.7 ± 2.6 | 6.9 | 43 ± 4*** (86.8) | 12.6 ± 0.9*** (46.8) |

*$p < 0.05$, $p < 0.01$, *$p < 0.001$. (mean ± S.E.)

TABLE IV

Effect of locally administered soft steroids and reference steroids on body weight, thymus weight and granulation tissue formation caused by implantation of cotton pellets in rats.

| Test Compound | Dose (μg pellet) | Number of Test Animals | Body wt. gain (g) | Granulation tissue Wet wt. (mg) | Granulation tissue Inhibition (%) |
|---|---|---|---|---|---|
| None (Control) | | 10 | 32.4 ± 1.4 | 566 ± 28 | |
| Chloromethyl 11β-hydroxy- | 100 | 8 | 34.9 ± 2.7 | 485 ± 36 | 14.3 |
| 17α-isopropoxycarbonyloxy- | 300 | 8 | 33.9 ± 1.6 | 431 ± 20** | 23.9 |
| androst-4-en-3-one-17β- | 1000 | 8 | 34.0 ± 2.6 | 305 ± 16*** | 46.1 |
| carboxylate | 3000 | 8 | 32.4 ± 2.3 | 292 ± 7*** | 48.4 |
| Chloromethyl 11β-hydroxy- | 30 | 8 | 32.4 ± 1.2 | 432 ± 15** | 23.7 |
| 17α-isopropoxycarbonyloxy- | 100 | 7 | 35.0 ± 1.5 | 417 ± 27** | 26.3 |
| androsta-1,4-dien-3-one- | 300 | 8 | 34.4 ± 1.1 | 369 ± 18*** | 34.8 |
| 17β-carboxylate | 1000 | 8 | 29.4 ± 1.5 | 289 ± 12*** | 48.9 |
| Chloromethyl 17α-ethoxy- | 0.3 | 8 | 32.4 ± 1.1 | 472 ± 23* | 16.6 |
| carbonyloxy-9α-fluoro-11β- | 1 | 8 | 37.3 ± 1.5* | 388 ± 31*** | 31.4 |
| hydroxy-16α-methylandrosta- | 3 | 8 | 34.3 ± 1.1 | 331 ± 11*** | 41.5 |
| 1,4-dien-3-one-17β-carboxylate | 10 | 8 | 36.1 ± 1.1 | 313 ± 13*** | 44.7 |
| | 30 | 8 | 31.3 ± 1.4 | 290 ± 10 | 48.8 |
| Chloromethyl 9α-fluoro-11β- | 1 | 7 | 33.0 ± 1.7 | 423 ± 19** | 25.3 |
| hydroxy-17α-isopropoxy- | 3 | 8 | 30.4 ± 1.1 | 351 ± 19*** | 38.0 |
| carbonyloxy-16β-methylandrosta- | 10 | 8 | 33.0 ± 1.5 | 362 ± 8*** | 36.0 |
| 1,4-dien-3-one-17β-carboxylate | 30 | 8 | 31.8 ± 1.7 | 315 ± 12*** | 44.3 |
| Hydrocortisone | 300 | 6 | 26.2 ± 1.7* | 333 ± 21*** | 41.2 |
| 17-butyrate | 1000 | 6 | 26.2 ± 1.2** | 366 ± 24*** | 35.3 |
| | 3000 | 6 | 6.7 ± 2.2*** | 329 ± 14*** | 41.9 |
| | 10000 | 6 | −2.0 ± 2.4*** | 311 ± 7*** | 45.1 |
| Betamethasone | 100 | 7 | 24.9 ± 1.9** | 400 ± 19*** | 29.3 |
| 17-valerate | 300 | 8 | 22.3 ± 1.2*** | 347 ± 15*** | 38.7 |
| | 1000 | 7 | 5.3 ± 1.0*** | 363 ± 28*** | 35.9 |
| | 3000 | 8 | 6.6 ± 1.4*** | 374 ± 15*** | 33.9 |

| Test Compound | Granulation tissue Dry wt. (mg) | Granulation tissue Inhibition (%) | Thymus wt. mg | Thymus wt. (Decrease %) |
|---|---|---|---|---|
| None (Control) | 81.2 ± 6.3 | | 445 ± 20 | |
| Chloromethyl 11β-hydroxy- | 70.0 ± 6.0 | 13.8 | 452 ± 29 | |
| 17α-isopropoxycarbonyloxy- | 50.9 ± 2.8** | 37.3 | 469 ± 25 | |
| androst-4-en-3-one-17β- | 24.1 ± 2.7*** | 70.3 | 464 ± 30 | |
| carboxylate | 20.3 ± 1.3*** | 75.0 | 459 ± 24 | |
| Chloromethyl 11β-hydroxy- | 51.0 ± 2.8** | 37.2 | 523 ± 26* | |
| 17α-isopropoxycarbonyloxy- | 41.1 ± 5.8*** | 49.4 | 537 ± 31* | |
| androsta-1,4-dien-3-one- | 38.1 ± 5.9*** | 53.1 | 525 ± 28* | |
| 17β-carboxylate | 18.5 ± 2.4*** | 77.2 | 423 ± 26 | |
| Chloromethyl 17α-ethoxy- | 57.3 ± 5.0* | 29.4 | 492 ± 26 | |
| carbonyloxy-9α-fluoro-11β- | 36.4 ± 2.4*** | 55.2 | 519 ± 22* | |
| hydroxy-16α-methylandrosta- | 27.4 ± 2.9*** | 66.3 | 472 ± 16 | |
| 1,4-dien-3-one-17β- | 22.1 ± 3.6*** | 72.8 | 521 ± 35 | |
| carboxylate | 20.4 ± 2.4*** | 74.9 | 505 ± 26 | |
| Chloromethyl 9α-fluoro-11β- | 44.4 ± 5.4*** | 45.3 | 526 ± 30* | |
| hydroxy-17α-isopropoxy- | 26.9 ± 4.4*** | 66.9 | 471 ± 20 | |
| carbonyloxy-16β-methyl- | 29.9 ± 3.3*** | 63.2 | 474 ± 25 | |
| androsta-1,4-dien-3-one- | 19.9 ± 2.3*** | 75.5 | 489 ± 26 | |
| 17β-carboxylate | | | | |
| Hydrocortisone | 34.0 ± 5.3*** | 58.1 | 353 ± 37* | (20.7) |
| 17-butyrate | 35.3 ± 4.2*** | 56.5 | 99 ± 7*** | (77.8) |
| | 28.0 ± 2.7*** | 65.5 | 58 ± 5*** | (87.0) |
| | 27.2 ± 2.4*** | 66.5 | 46 ± 7*** | (89.7) |
| Betamethasone | 41.1 ± 2.7*** | 49.4 | 364 ± 24* | (18.2) |
| 17-valerate | 33.3 ± 3.6*** | 59.0 | 264 ± 29*** | (40.7) |
| | 38.1 ± 4.8*** | 53.1 | 77 ± 5*** | (82.7) |
| | 43.0 ± 4.1*** | 47.0 | 63 ± 3*** | (85.8) |

*p < 0.05, p < 0.01, *p < 0.001. (Mean ± S.E.)

TABLE V-a

Effect of locally administered soft steroids and reference steroids on body weight, thymus weight and granulation tissue formation caused by implantation of cotton pellets in rats.

| Test Compound | Dose (μg/pellet) | Number of Test Animals | Body wt. gain (g) | Granulation Tissue Wet wt. (mg) | Granulation Tissue Inhibition (%) |
|---|---|---|---|---|---|
| None (Control) | | 10 | 33.5 ± 1.0 | 525 ± 19 | |
| Chloromethyl 17α-ethoxy- | 0.3 | 8 | 32.5 ± 1.1 | 499 ± 36 | 5.0 |
| carbonyloxy-9α-fluoro- | 1 | 8 | 36.3 ± 0.9 | 437 ± 24* | 16.8 |
| 11β-hydroxy-16β-methyl- | 3 | 8 | 33.8 ± 1.3 | 422 ± 32* | 19.6 |
| androsta-1,4-dien-3-one- | 10 | 8 | 31.1 ± 1.7 | 370 ± 21*** | 29.5 |
| 17β-carboxylate | | | | | |
| Chloromethyl 9α-fluoro-11β- | 0.3 | 8 | 35.6 ± 1.0 | 454 ± 27* | 13.5 |

TABLE V-a-continued

Effect of locally administered soft steroids and reference steroids on body weight, thymus weight and granulation tissue formation caused by implantation of cotton pellets in rats.

| | | | | | |
|---|---|---|---|---|---|
| hydroxy-16α-methyl-17α- | 1 | 8 | 31.9 ± 0.8 | 415 ± 30** | 21.0 |
| propoxycarbonyloxyandrosta- | 3 | 7 | 34.1 ± 1.9 | 360 ± 18*** | 31.4 |
| 1,4-dien-3-one-17β- | 10 | 8 | 33.1 ± 1.6 | 350 ± 13*** | 33.3 |
| carboxylate | | | | | |
| Betamethasone | 10 | 6 | 31.8 ± 1.6 | 375 ± 19*** | 28.6 |
| 17-valerate | 30 | 6 | 30.8 ± 3.0 | 412 ± 42* | 21.5 |
| | 100 | 6 | 25.7 ± 1.2*** | 419 ± 20** | 20.2 |
| Clobetasol | 1 | 8 | 33.0 ± 1.2 | 401 ± 29** | 23.6 |
| 17-propionate | 3 | 7 | 24.9 ± 1.8*** | 402 ± 40** | 23.4 |
| | 10 | 8 | 25.0 ± 2.1** | 364 ± 25*** | 30.7 |
| | 30 | 8 | 24.8 ± 1.1*** | 320 ± 10*** | 39.0 |
| | 100 | 8 | 15.9 ± 1.0*** | 325 ± 12*** | 38.1 |

| | Granulation Tissue | | | |
|---|---|---|---|---|
| | Dry wt. | Inhibition | Thymus wt. | |
| Test Compound | (mg) | (%) | mg | (Decrease %) |
| None (Control) | 80.1 ± 5.1 | | 495 ± 36 | |
| Chloromethyl 17α-ethoxy- | 61.8 ± 5.7* | 22.8 | 501 ± 29 | |
| carbonyloxy-9α-fluoro- | 57.0 ± 6.2* | 28.8 | 566 ± 31 | |
| 11β-hydroxy-16β-methyl- | 47.5 ± 5.0*** | 40.7 | 500 ± 27 | |
| androsta-1,4-dien-3-one- | 34.8 ± 5.5*** | 56.6 | 421 ± 30 | |
| 17β-carboxylate | | | | |
| Chloromethyl 9α-fluoro-11β- | 55.1 ± 6.2** | 31.2 | 523 ± 28 | |
| hydroxy-16α-methyl-17α- | 42.9 ± 5.1*** | 46.4 | 453 ± 21 | |
| propoxycarbonyloxyandrosta- | 29.7 ± 3.2*** | 62.9 | 504 ± 42 | |
| 1,4-dien-3-one-17β- | 28.5 ± 2.8*** | 64.4 | 547 ± 26 | |
| carboxylate | | | | |
| Betamethasone | 38.5 ± 6.2*** | 51.9 | 479 ± 25 | (3.2) |
| 17-valerate | 46.2 ± 7.4** | 42.3 | 484 ± 23 | (2.2) |
| | 41.0 ± 4.2*** | 48.8 | 378 ± 30* | (23.6) |
| Clobetasol | 42.0 ± 5.8*** | 47.6 | 478 ± 22 | (3.4) |
| 17-propionate | 43.1 ± 8.9** | 46.2 | 449 ± 21 | (9.3) |
| | 37.9 ± 6.8*** | 52.7 | 322 ± 22** | (34.9) |
| | 25.5 ± 2.1*** | 68.2 | 174 ± 26*** | (64.8) |
| | 23.9 ± 3.3*** | 70.2 | 84 ± 3*** | (83.0) |

*$p < 0.05$, $p < 0.01$, *$p < 0.001$. (Mean ± S.E.)

TABLE V-b

Effect of locally administered soft steroids on body weight, thymus weight and granulation tissue formation caused by implantation of cotton pellets in rats.

| Test Compound | Dose (μg/pellet) | Number of Test animals | Body wt. gain (g) | Dry granulation Tissue mg | Inhibition % | Thymus wt. mg |
|---|---|---|---|---|---|---|
| None (Control) | — | 10 | 28.0 ± 1.5 | 67.2 ± 3.4 | | 505 ± 22 |
| Chloromethyl 9α-fluoro-17α- | 1 | 8 | 28.9 ± 1.1 | 59.1 ± 5.8 | 12.1 | 441 ± 24 |
| isopropoxycarbonyloxy-16β- | 3 | 8 | 25.8 ± 0.9 | 49.4 ± 37** | 26.5 | 519 ± 31 |
| methylandrosta-1,4-dien- | 10 | 7 | 28.4 ± 0.8 | 51.1 ± 5.8* | 24.0 | 547 ± 35 |
| 3,11-dione-17β-carboxylate | 30 | 8 | 27.4 ± 0.9 | 40.6 ± 3.6*** | 39.6 | 536 ± 24 |
| Chloromethyl 17α-ethoxy- | 1 | 7 | 23.7 ± 1.5 | 55.3 ± 2.6* | 17.7 | 459 ± 41 |
| carbonyloxy-9α-fluoro-16α- | 3 | 8 | 25.6 ± 1.2 | 51.6 ± 5.9* | 23.2 | 467 ± 21 |
| methylandrosta-1,4-dien- | 10 | 8 | 26.5 ± 2.5 | 41.5 ± 4.7*** | 38.2 | 544 ± 31 |
| 3,11-dione-17β-carboxylate | 30 | 8 | 20.3 ± 0.9** | 39.9 ± 3.6*** | 40.6 | 463 ± 24 |

*p 0.05, p 0.01, *p 0.001. (Mean ± S.E.)
Male Sprague-Dawley rats, weighing 152–189 g (mean body weight 171 g), were used. Cotton pellet weight was 30.1 + 0.3 mg (number of test animals were 30).

The test data in Tables III, IV and V-a and V-b above clearly show that the representative compounds of the present invention exhibited a significant anti-inflammatory response at lower dosages than did the prior art steroids, hydrocortisone 17-butyrate and betamethasone 17-valerate. On the other hand, all of the prior art steroids dramatically decreased the weight of the thymi and thus showed very potent systemic activity, while the representative compounds of the invention either did not significantly decrease the thymi weights or only minimally decreased the thymi weight. Thus, the present compounds have a much greater therapeutic index, i.e., separation of local anti-inflammatory from systemic activity, than do the prior art steroidal anti-inflammatory agents.

Also the test data in Table V-b above shows that the representative compounds of the present invention exhibited a significant local anti-inflammatory activity.

From the results tabulated in Tables IV and V-b, the $ED_{40}$'s, $ED_{50}$'s and $ED_{60}$'s and the relative potencies of representative compounds of the invention were calculated and are shown in Table VI below. One of the compounds of the invention, namely chloromethyl 11-hydroxy-17-isopropoxycarbonyloxyandrost-4-en-3-one-17-carboxylate, has been asigned a potency value of 1 at each ED level, and the potencies of the other compounds are expressed relative thereto. The $ED_{40}$'s, $ED_{50}$'s and $ED_{60}$'s are the dosages required to achieve, respectively, 40%, 50% and 60% reduction in the weight of the granulation tissue.

TABLE VI

Relative potencies of soft steroids in the local cotton pellet granuloma assay.

| Test Compound | $ED_{40}$[1] (μg/pellet) | Relative potency | $ED_{50}$[2] (μg/pellet) | Relative potency | $ED_{60}$[3] (μg/pellet) | Relative potency |
|---|---|---|---|---|---|---|
| Chloromethyl 11β-hydroxy-17α-isopropoxycarbonyloxyandrost-4-en-one-17β-carboxylate | 307 (238–394) | 1 | 460 (360–623) | 1 | 690 (523–1023) | 1 |
| Chloromethyl 11β-hydroxy-17α-isopropoxycarbonyloxyandrosta-1,4-dien-3-one-17β-carboxylate | 47 (15–85) | 6.5 | 119 (60–202) | 3.9 | 301 (178–627) | 2.3 |
| Chloromethyl 17α-ethoxy-carbonyloxy-9α-fluoro-11β-hydroxy-16α-methylandrosta-1,4-dien-3-one-17β-carboxylate | 0.47 (0.23–0.75) | 653 | 1.07 (0.66–1.59) | 430 | 2.44 (1.65–3.86) | 283 |
| Chloromethyl 9α-fluoro-11β-hydroxy-17α-isopropoxycarbonyloxy-16β-methylandrosta-1,4-dien-3-one-17β-carboxylate | 0.25 (0.004–0.886) | 1228 | 0.97 (0.08–2.31) | 474 | 3.75 (1.25–7.68) | 184 |
| Chloromethyl 17α-ethoxycarbonyloxy-9α-fluoro-11β-hydroxy-16β-methylandrosta-1,4-dien-3-one-17β-carboxylate | 2.31 (1.07–6.38) | 133 | 6.45 (2.96–44.58) | 71 | 18.01 (6.47–393.8) | 38 |
| Chloromethyl 9α-fluoro-11β-hydroxy-16α-methyl-17α-propoxycarbonyloxyandrosta-1,4-dien-3-one-17β-carboxylate | 0.58 (0.20–1.01) | 529 | 1.20 (0.67–2.88) | 383 | 2.49 (1.37–13.32) | 277 |
| Hydrocortisone 17-butyrate | — | — | — | — | 1015 (724–26866) | 0.7 |
| Clobetasol 17-propionate | — | — | >3 | — | >10 | — |

[1]dose causing 40% inhibition of granulation tissue weight.
[2]dose causing 50% inhibition of granulation tissue weight.
[3]dose causing 60% inhibition of granulation tissue weight.
( ) = 95% confidence limits

THYMUS INHIBITION TESTING

Several further studies were undertaken to determine the effects of selected compounds of the invention on thymi weights in rats when the drugs were systemically administered. In each of these studies, male Sprague-Dawley rats were used. (For average weight of rats for each study, see the tables which follow.) The test compounds were suspended in 0.5% CMC (carboxymethylcellulose) and injected subcutaneously once daily for three days. On the fifth day (48 hours following the last treatment), the animals were sacrificed and the thymi weights were recorded. Body weight gains were measured 24 hours after the last treatment. The test results are set forth in Tables VII, VIII and IX below. The $TED_{40}$'s, $TED_{50}$'s (thymolytic effective doses or doses required to achieve 40% and 50% inhibition of thymi weight, respectively) and relative potency of representative compounds of the invention and reference steroids are shown in Table X below. In Table X, the $TED_{40}$ and $TED_{50}$ for the reference steroid betamethasone 17-valerate has each been assigned a value of 1, and the potencies of the other compounds are expressed relative thereto. It is evident that the higher the inhibition of thymus activity at a given dose, the more toxic the compound is.

TABLE VII

Effects of systemically administereed (s.c.) soft steroids and reference steroids on body weight and thymus weight in rats.

| Test Compound | Dose (mg/kg/day) | Number of Test Animals | Body weight gain (g) | Thymus (mg) | Inhibition (%) |
|---|---|---|---|---|---|
| None (Control) | | 9 | 18.3 ± 0.7 | 471 ± 21 | |
| Chloromethyl 11β-hydroxy-17α-isopropoxycarbonyloxy-androst-4-en-3-one-17β-carboxylate | 3 | 9 | 14.7 ± 0.6** | 439 ± 18 | 6.8 |
| | 10 | 10 | 10.2 ± 0.7*** | 386 ± 17** | 18.0 |
| | 30 | 10 | 6.8 ± 2.1*** | 291 ± 22*** | 38.2 |
| | 100 | 10 | 2.8 ± 1.8*** | 185 ± 17*** | 60.7 |
| Chloromethyl 11β-hydroxy-17α-isopropoxycarbonyl-oxyandrosta-1,4-dien-3-one-17β-carboxylate | 3 | 9 | 9.0 ± 0.9*** | 377 ± 16** | 20.0 |
| | 10 | 9 | 6.2 ± 0.7*** | 312 ± 23*** | 33.8 |
| | 30 | 10 | 4.8 ± 1.4*** | 257 ± 24*** | 45.4 |
| | 100 | 10 | 0.3 ± 1.6*** | 161 ± 19*** | 65.8 |
| Chloromethyl 17α-ethoxy-carbonyloxy-9α-fluoro-11β-hydroxy-16α-methyl-androsta-1,4-dien-3-one-17β-carboxylate | 1 | 10 | 13.1 ± 1.0*** | 428 ± 20 | 9.1 |
| | 3 | 9 | 12.7 ± 1.4** | 412 ± 20 | 12.5 |
| | 10 | 10 | 9.7 ± 1.3*** | 405 ± 21* | 14.0 |
| | 30 | 10 | 4.4 ± 0.7*** | 292 ± 15*** | 38.0 |
| Hydrocortisone 17-butyrate | 0.3 | 10 | 17.0 ± 0.8 | 441 ± 27 | 6.4 |
| | 1 | 10 | 11.8 ± 0.8*** | 323 ± 16*** | 31.4 |
| | 3 | 10 | 7.3 ± 0.5*** | 166 ± 5*** | 64.8 |
| | 10 | 10 | −5.0 ± 1.1*** | 65 ± 5*** | 86.2 |
| Betamethasone 17-valerate | 0.1 | 10 | 15.5 ± 0.9* | 362 ± 16*** | 23.1 |
| | 0.3 | 10 | 12.4 ± 0.9*** | 276 ± 11*** | 41.4 |
| | 1 | 10 | 13.0 ± 1.1*** | 200 ± 14*** | 57.5 |

TABLE VII-continued

| Effects of systemically administereed (s.c.) soft steroids and reference steroids on body weight and thymus weight in rats. | | | | | |
|---|---|---|---|---|---|
| Test Compound | Dose (mg/kg/day) | Number of Test Animals | Body weight gain (g) | Thymus (mg) | Inhibition (%) |
| | 3 | 10 | 9.9 ± 1.3*** | 119 ± 7*** | 74.7 |

*p < 0.05, p < 0.01, *p < 0.001 (Mean ± S.E.)
Male Sprague-Dawley rats, weighing 149-168 g, were used.

TABLE VIII

| Effects of systemically administered (s.c.) soft steroids and reference steroids on body weight and thymus weight in rats. | | | | | |
|---|---|---|---|---|---|
| Test Compound | Dose (mg/kg/day) | Number of Test Animals | Body weight gain (g) | Thymus wt. (mg) | Inhibition (%) |
| None (Control) | | 10 | 18.9 ± 0.6 | 550 ± 24 | |
| Chloromethyl 17α-ethoxycarbonyloxy-9α-fluoro-11β-hydroxy-16α-methyl-androsta-1,4-dien-3-one-17β-carboxylate | 10 | 7 | 14.2 ± 1.9 | 533 ± 31 | 3.1 |
| Chloromethyl 9α-fluoro-11β-hydroxy-17α-isopropoxycarbonyloxy-16α-methylandrosta-1,4-dien-3-one-17β-carboxylate | 10 | 7 | 2.7 ± 1.9*** | 234 ± 31*** | 57.5 |
| Chloromethyl 9α-fluoro-11β-hydroxy-17α-isopropoxycarbonyloxy-16β-methylandrosta-1,4-dien-3-one-17β-carboxylate | 10 | 7 | 5.3 ± 1.4*** | 260 ± 26*** | 52.7 |
| Chloromethyl 17α-ethoxycarbonyloxy-9α-fluoro-11β-hydroxy-16β-methylandrosta-1,4-dien-3-one-17β-carboxylate | 10 | 7 | 2.4 ± 1.8*** | 266 ± 20*** | 51.6 |
| Chloromethyl 9α-fluoro-11β-hydroxy-16α-methyl-17α-propoxycarbonyloxy-androsta-1,4-dien-3-one-17β-carboxylate | 10 | 7 | 2.7 ± 1.7*** | 277 ± 25*** | 49.6 |
| Clobetasol | 0.003 | 8 | 18.2 ± 0.6 | 537 ± 28 | 2.4 |
| 17-propionate | 0.01 | 8 | 15.5 ± 1.1* | 498 ± 15 | 9.5 |
| | 0.03 | 8 | 12.3 ± 1.3** | 363 ± 22*** | 34.0 |
| | 0.1 | 8 | −0.4 ± 1.3*** | 149 ± 9*** | 72.9 |
| | 0.3 | 8 | −14.3 ± 1.3*** | 63 ± 3*** | 88.5 |

*p < 0.05, p < 0.01, *p < 0.001. (mean ± S.E.)
Male Sprague-Dawley rats, weighing about 185 g (162-209 g), were used.

TABLE IX

| Effects of systemically administered (s.c.) soft steroids on body weight and thymus weight in rats. | | | | | |
|---|---|---|---|---|---|
| Test Compound | Dose (mg/kg/day) | Number of Test Animals | Body weight gain (g) | Thymus wt. (mg) | Decrease (%) |
| None (Control) | | 10 | 21.2 ± 0.9 | 426 ± 17 | |
| Chloromethyl 9α-fluoro-11β- | 3 | 7 | 18.8 ± 1.4 | 426 ± 19 | 0.0 |
| hydroxy-17α-methoxycarbonyloxy- | 10 | 7 | 13.8 ± 1.6*** | 354 ± 8** | 16.9 |
| 16α-methylandrosta-1,4-dien-3- | 30 | 7 | 12.0 ± 0.8*** | 282 ± 11*** | 33.8 |
| one-17β-carboxylate | 100 | 7 | 9.8 ± 1.3*** | 206 ± 15*** | 51.6 |
| Chloromethyl 9α-fluoro-11β- | 1 | 7 | 18.0 ± 1.5 | 387 ± 23 | 9.2 |
| hydroxy-16α-methyl-17α- | 3 | 7 | 15.6 ± 1.3** | 347 ± 15** | 18.5 |
| pentyloxycarbonyloxyandrosta- | 10 | 7 | 17.4 ± 1.5* | 357 ± 22* | 16.2 |
| 1,4-dien-3-one-17β-carboxylate | 30 | 7 | 13.5 ± 1.0*** | 335 ± 17** | 21.4 |

*p < 0.05, p < 0.01, *p < 0.001 (Mean ± S.E.)
Male Sprague-Dawley rats, weighing 91-112 g, were used.

TABLE X

| Thymolytic activities of soft steroids administered subcutaneously to rats. | | | | |
|---|---|---|---|---|
| Compound | $TED_{40}$ (mg) | Relative Potency | $TED_{50}$ (mg) | Relative Potency |
| Chloromethyl 11β-hydroxy-17α-isopropoxycarbonyloxyandrost-4-en-3-one-17β-carboxylate | 31.0 (23.9-41.9) | 0.01 | 58.5 (43.1-87.1) | 0.01 |
| Chloromethyl 11β-hydroxy-17α-isopropoxycarbonyloxyandrosta-1,4-dien-3-one-17β-carboxylate | 16.2 (11.2-23.2) | 0.02 | 35.3 (24.6-57.5) | 0.02 |
| Chloromethyl 17α-ethoxycarbonyloxy-9α-fluoro-11β-hydroxy-16α-methylandrosta-1,4-dien-3-one-17β-carboxylate | 51.5 (26.5-290.0) | 0.0058 | >51.5[a] | <0.011 |
| Hydrocortisone 17-butyrate | 1.3 (1.1-1.5) | 0.23 | 2.0 (1.7-2.3) | 0.29 |
| Betamethasone | 0.30 | 1 | 0.58 | 1 |

TABLE X-continued

| Thymolytic activities of soft steroids administered subcutaneously to rats. | | | | |
|---|---|---|---|---|
| Compound | $TED_{40}$ (mg) | Relative Potency | $TED_{50}$ (mg) | Relative Potency |
| 17-valerate | (0.24–0.36) | | (0.49–0.69) | |
| Clobetasol | 0.035 | 8.6 | 0.052 | 11.2 |
| 17-propionate | (0.030–0.039) | | (0.046–0.059) | |

[a]Even at a dosage level of 100 mg/kg/day, 50% reduction in thymus weight could not be achieved.

BLANK COTTON PELLET GRANULOMA ASSAY

A further test was undertaken to determine the thymolytic activity of a representative species of the invention as compared to betamethasone 17-valerate. In this test, the drugs were administered intravenously to rats, while using a blank cotton pellet granuloma assay. Male Sprague-Dawley rats, each weighing about 185 grams (166–196 grams), were used. Two cotton pellets, each weighing 30 mg and containing no test compounds, were sterilized and implanted subcutaneously into the back of each test animal. This day was considered day 0 of implantation. Test compounds suspended in 0.8% polysorbate 80 were administered intravenously once daily for 3 consecutive days beginning with day 1. On day 5, the animals were sacrificed and the two pellets, with their respective granulomas, were removed, dried overnight in an oven at 50° C. and weighed (dry granuloma weight). The thymi and final body weights were also recorded. The results are given in Table XI below.

In the foregoing tests, there was determined the deactivation of the representative species of the present soft steroids administered intravenously to rats. The ratio between the potencies of the test steroids and betamethasone 17-valerate against local anti-inflammation was 283:0.7 as seen from Table VI. This means that the test compounds exhibit a local anti-inflammatory activity which is approximately 400 times as high as the activity of the betamethasone 17-valerate. The test compounds were administered intravenously to rats to check the test compounds also for systemic anti-inflammatory activity as compared to betamethasone 17-valerate. The test compounds were found lower in the inhibition of granulation tissue formation and also in the thymus involution activity than betamethasone 17-valerate. From the results of the tests, it is presumed that the compounds which will not be readily subjected to metabolism (deactivation) have a systemic anti-inflammatory activity, as is the case with betamethasone 17-valerate.

TABLE XI

| Thymolytic activities of test steroids administered intravenously to rats in the blank cotton pellet granuloma assay. | | | | | | | |
|---|---|---|---|---|---|---|---|
| Test Compound | Dose (mg/kg/day) | Number of Test Animals | Body wt. gain (g) | Dry granuloma wt. (mg) | Inhibition (%) | Thymus wt. (mg) | Decrease (%) |
| None (Control) | | 7 | 21.4 ± 1.3 | 62.7 ± 6.1 | | 422 ± 27 | |
| Chloromethyl 17α- | 1 | 7 | 14.1 ± 1.4** | 50.1 ± 6.9 | 20.1 | 373 ± 25 | 11.6 |
| ethoxycarbonyloxy-9α- | 3 | 6 | 14.2 ± 1.3** | 49.3 ± 5.1 | 21.4 | 338 ± 20* | 19.9 |
| fluoro-11β-hydroxy- | 10 | 6 | 0.3 ± 1.7*** | 45.7 ± 4.6 | 27.1 | 209 ± 31*** | 50.5 |
| 16α-methylandrosta- | 30 | 6 | −18.5 ± 2.3*** | 32.7 ± 3.0** | 47.8 | 71 ± 4*** | 83.2 |
| 1,4-dien-3-one-17β- | | | | | | | |
| carboxylate | | | | | | | |
| Betamethasone | 0.1 | 7 | 14.4 ± 1.6** | 49.3 ± 3.9 | 21.4 | 305 ± 14** | 27.7 |
| 17-valerate | 0.3 | 5 | 12.2 ± 1.1*** | 44.4 ± 2.8* | 29.2 | 288 ± 27** | 31.8 |
| | 1 | 7 | 12.9 ± 1.1*** | 46.1 ± 4.3* | 26.5 | 233 ± 15*** | 44.8 |
| | 3 | 7 | 13.0 ± 2.5* | 47.3 ± 2.7 | 24.6 | 167 ± 22*** | 60.4 |

*$p < 0.05$, $p < 0.01$, *$p < 0.001$. (Mean ± S.E.)

The $ED_{50}$'s calculated for the local cotton pellet granuloma assay (as shown, for example, in Table VI above) and the $TED_{40}$'s calculated on the basis of thymus inhibition testing (as shown, for example, in Table X above) were used to arrive at relative potency and a therapeutic index for representative species of the invention as compared to prior art steroids. See Table XII below, which clearly shows the potent anti-inflammatory activity and minimal systemic toxicity of the compounds of the present invention.

TABLE XII

| Therapeutic Indices of representative species of the invention as compared to prior art steroids. | | | | | |
|---|---|---|---|---|---|
| Compound | $ED_{50}$[a] | Relative Potency | $TED_{40}$[b] | Relative Potency | Therapeutic Index[c] |
| Chloromethyl 11β-hydroxy-17α-isopropoxycarbonyloxyandrost-4-en-3-one-17β-carboxylate | 460 (360–623) | 1 | 31.0 (23.9–41.9) | 1/24 | 24 |
| Chloromethyl 11β-hydroxy-17α-isopropoxycarbonyloxyandrosta-1,4-dien-3-one-17β-carboxylate | 119 (60–202) | 4 | 16.2 (11.2–23.2) | 1/12 | 48 |
| Chloromethyl 17α-ethoxycarbonyloxy-9α-fluoro-11β-hydroxy-16α-methylandrosta-1,4-dien-3-one-17β-carboxylate | 1.07 (0.66–1.59) | 450 | 51.5 (26.5–290.0) | 1/40 | 18000 |
| Chloromethyl 9α-fluoro-11β-hydroxy-17α-methoxycarbonyloxy-16α-methylandrosta-1,4-dien-3-one-17β-carboxylate | 2.38 (1.60–3.78) | 202 | 46.0 (36.0–62.1) | 1/36 | 7270 |
| Hydrocortisone | 480 | 1 | 1.3 | 1 | 1 |

TABLE XII-continued

Therapeutic Indices of representative species of the invention as compared to prior art steroids.

| Compound | $ED_{50}$[a] | Relative Potency | $TED_{40}$[b] | Relative Potency | Therapeutic Index[c] |
|---|---|---|---|---|---|
| 17-butyrate | (313-892) | | (1.1-1.5) | | |
| Betamethasone | 100 | 5 | 0.3 | 4 | 1 |
| 17-valerate | | | (0.24-0.36) | | |

[a]for the anti-inflammatory effect in cotton pellet granuloma (μg/pellet)
[b]for the thymus inhibition effect required subcutaneously (mg/kg)
[c]the ratio of the relative potency for the $ED_{50}$ to the relative potency for the $TED_{40}$; hydrocortisone 17-butyrate has been assigned a value of one The compounds of formula (I) can be combined with suitable non-toxic pharmaceutically acceptable carriers to provide pharmaceutical compositions for use in the treatment of topical or other localized inflammation. Obviously, in view of their lack of systemic activity, the compounds of the present invention are not intended for treatment of conditions where systemic adrenocortical thereapy is indicated, e.g., adrenocortical insufficiency. As examples of inflammatory conditions which can be treated with pharmaceutical compositions containing at least one compound of the invention and one or more pharmaceutical carriers, the following can be mentioned. dermatological disorders such as atopic dermatitis, acne, psoriasis or contact dermatitis; allergic states such as bronchial asthma; ophthalmic and otic diseases involving acute and chronic allergic and inflammatory reactions; respiratory diseases; ulcerative colitis; and anorectal inflammation, pruritus and pain associated with hemorrhoids, proctitis, cryptitis, fissures, postoperative pain and pruritus ani. Such compositions may also be applied locally as a propylactic measure against the inflammation and tissue rejection which arise in connection with transplants.

Obviously, the choice of carrier(s) and dosage forms will vary with the particular condition for which the composition is to be administered.

Examples of various types of preparations for topical/local administration include ointments, lotions, creams, powders, drops, (e.g. eye or ear drops), sprays, (e.g. for the nose or throat), suppositories, retention enemas, chewable or suckable tablets or pellets (e.g. for the treatment of aphthous ulcers) and aerosols. Ointments and creams may, for example, be formulated with an aqueous or oily base with the addition of suitable thickening and/or gelling agents and/or glycols. Such base may thus, for example, include water and/or an oil such as liquid paraffin or a vegetable oil such as arachis oil or castor oil, or a glycolic solvent such as propylene glycol or 1,3-butanediol. Thickening agents which may be used according to the nature of the base include soft paraffin, aluminum stearate, cetostearyl alcohol, polyethylene glycols, woolfat, hydrogenated lanolin and beeswax and/or glyceryl monostearate and/or nonionic emulsifying agents.

The solubility of the steroid in the ointment or cream may be enhanced by incorporation of an aromatic alcohol such as benzyl alcohol, phenylethyl alcohol or phenoxyethyl alcohol.

Lotions may be formulated with an aqueous or oily base and will in general also include one or more of the following, namely, emulsifying agents, dispersing agents, suspending agents, thickening agents, solvents, coloring agents and perfumes. Powders may be formed with the aid of any suitable powder base e.g. talc, lactose or starch. Drops may be formulated with an aqueous base also comprising one or more dispersing agents, suspending agents or solubilizing agents, etc. Spray compositions may, for example, be formulated as aerosols with the use of a suitable propellane, e.g., dichlorodifluoromethane or trichlorofluoromethane.

The proportion of active ingredient in the compositions according to the invention will vary with the precise compound used, the type of formulation prepared and the particular condition for which the composition is to be administered. The formulation will generally contain from about 0.0001 to about 5% by weight of the compound of formula (I). Topical preparations will generally contain 0.0001 to 2.5%, preferably 0.01 to 0.5%, and will be administered once daily, or as needed. Also, generally speaking, the compounds of the invention can be incorporated into topical and other local compositions formulated substantially as are such presently available types of compositions containing known glucocorticosteroids, at approximately the same (or in the case of the most potent compounds of the invention, at proportionately lower) dosage levels as compared to known highly active agents such as methyl prednisolone acetate and beclomethasone dipropionate or at considerably lower dosage levels as compared to less active known agents such as hydrocortisone.

Thus, for example, an inhalation formulation suitable for use in the treatment of asthma can be prepared as a metered-dose aerosol unit containing a representative species of the invention such as chloromethyl 17α-ethoxycarbonyloxy-11β-hydroxyandrost-4-en-3-one-17β-carboxylate, according to procedures well-known to those skilled in the art of pharmaceutical formulations. Such an aerosol unit may contain a microcrystalline suspension of the aforementioned compound in suitable propellants (e.g., trichlorofluoromethane and dichlorodifluoromethane), with oleic acid or other suitable dispersing agent. Each unit typically contains 10 milligrams of the aforesaid active ingredient, approximately 50 micrograms of which are released at each actuation. When one of the more potent species of the invention, e.g. chloromethyl 17α-ethoxycarbonyloxy-9α-fluoro-11β-hydroxy-16α-methylandrosta-1,4-dien-3-one-17β-carboxylate, is employed, each unit typically contains 1 milligram of the active ingredient and releases approximately 5 micrograms at each actuation.

Another example of a pharmaceutical composition according to the invention is a foam suitable for treatment of a wide variety of inflammatory anorectal disorders, to be applied anally or perianally, comprising 0.1% of a compound of formula (I) such as chloromethyl 17α-ethoxycarbonyloxy-11β-hydroxyandrosta-4-en-3-one-17β-carboxylate, and 1% of a local anaesthetic such as pramoxine hydrochloride, in a mucoadhesive foam base of propylene glycol, ethoxylated stearyl alcohol, polyoxyethylene-10-stearyl ether, cetyl alcohol, methyl paraben, propyl paraben, triethanolamine, and water, with inert propellents. When a more potent compound of the invention is employed, less active ingredient generally is used, e.g. 0.05% of chloromethyl 9α-fluoro-11β-hydroxy-17α-methoxycarbonyloxy-16α-methylandrosta-1,4-dien-3-one-17β-carboxylate.

Yet another pharmaceutical formulation according to the invention is a solution or suspension suitable for use as a retention enema, a single dose of which typically contains 40 milligrams of a compound of the invention such as chloromethyl 17α-ethoxycarbonyloxy-11β-hydroxyandrost-4-en-3-one-17β-carboxylate (or 20 milligrams of a more potent compound of the invention such as chloromethyl 9α-fluoro-11β-hydroxy-17α-isopropoxycarbonyloxy-16β-methylandrosta-1,4-dien-3-one-17β-carboxylate or chloromethyl 9α-fluoro-11β-hydroxy-16α-methyl-17α-propoxycarbonyloxyandrosta-1,4-dien-3-one-17β-carboxylate) together with sodium chloride, polysorbate 80 and from 1 to 6 ounces of water (the water being added shortly before use). The suspension can be administered as a retention enema or by continuous drip several times weekly in the treatment of ulcerative colitis.

Other pharmaceutical formulations according to the invention are illustrated in the examples which follow.

Without further elaboration, it is believed that one of ordinary skill in the art can, using the preceding description, utilize the present invention to its fullest extent. Therefore, the following examples are to be construed as merely illustrative and not limitative of the remainder of the specification and claims in any way whatsoever.

EXAMPLE 1

To a solution of hydrocortisone (15 grams, 0.04 mol) in 120 milliliters of tetrahydrofuran and 30 milliliters of methanol at room temperature is added a warm (approximately 50° C.) solution of sodium metaperiodate (25.7 grams, 0.12 mol) in 100 milliliters of water). The reaction mixture is stirred at room temperature for 2 hours, then is concentrated under reduced pressure to remove the tetrahydrofuran and methanol. The solid is triturated with 50 milliliters of water, separated by filtration, washed with water and dried in vacuo at 50° C. for 3 hours. The product, 11β,17α-dihydroxyandrost-4-en-3-one-17β-carboxylic acid (i.e., cortienic acid), melts at 231°-234° C., is obtained in approximately 96% yield (13.76 grams), and can be represented by the structural formula

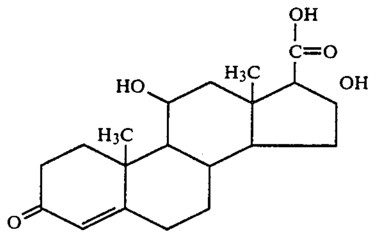

EXAMPLE 2

To a cold solution of 11β,17α-dihydroxyandrost-4-en-3-one-17β-carboxylic acid (5% weight/volume; 1 mol) and triethylamine (4 mol) in dichloromethane is added a 50% (weight/volume) solution of methyl chloroformate (3.9 mol) in dichloromethane. The reaction mixture is allowed to warm to room temperature over a 2 hour period. The triethylamine hydrochloride precipitate which forms is removed by filtration and the filtration is washed successively with 3% sodium bicarbonate, dilute (~1%) hydrochloric acid and water. The organic layer is separated, dried with magnesium sulfate, and filtered. The filtrate is concentrated in vacuo to a foam. The foam is used in the next step (e.g., Example 3 below) or chromatographed and crystallized for analysis. The product, 11β-hydroxy-17α-methoxycarbonyloxyandrost-4-en-3-one-17β-carboxylic acid, melts at 198°-204° C. after chromatography and crystallization; ir (KBr) 3000-2800 (C—H), 1750, 1735, 1720 (C═O), 1650, 1640 (C═C—C═O) $cm^{-1}$. The product can be represented by the structural formula

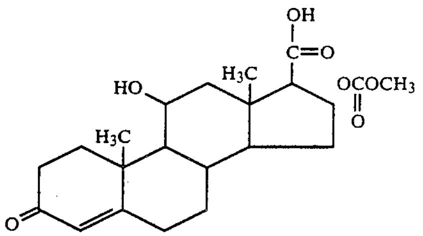

Substitution of an equivalent quantity of ethyl chloroformate for the methyl chloroformate employed above and substantial repetition of the foregoing procedure affords 17α-ethoxycarbonyloxy-11β-hydroxyandrost-4-en-3-one-17β-carboxylic acid, melting at 192°-195° C. after chromatography and crystalization; ir (KBr) 3500 (11β-O—H), 3000-2800 (C—H), 1740 (C═O), 1630 (C═C—C═O) $cm^{-1}$, nmr($CDCl_3$) δ6.4(1, b, COOH), 5.67(1, s, C—CH), 4.43 (1, b, CHOE), 4.13 (2, q, J=7.5 Hz, $OCH_2CH_3$); Anal. calcd. for $C_{23}H_{32}O_7$: C, 65.69; H, 7.67. Found: C, 65.76; H, 7.74.

In a similar manner, substitution of an equivalent quantity of butyl chloroformate for the methyl chloroformate employed in the frist paragraph of this example and substantial repetition of the procedure there detailed affords 17α-butoxycarbonyloxy-11β-hydroxyandrost-4-en-3-one-17β-carboxylic acid. The final product, after crystallization from tetrahydrofuran-hexane, melts at 164°-166° C.

Similarly, substituting an equivalent amount of isopropyl chloroformate for the methyl chloroformate used in the first paragraph of this example and repeating the procedure there detailed affords 11β-hydroxy-17α-isopropoxycarbonyloxyandrost-4-en-3-one-17β-carboxylic acid. The final product, after crystallization from tetrahydrofuran-hexane, melts at 144.5°-146.5° C.

EXAMPLE 3

11β-Hydroxy-17α-methoxycarbonyloxyandrost-4-en-3-one-17β-carboxylic acid is combined with an equivalent amount of 1N sodium hydroxide in methanol and that solution is diluted to 100 times the original volume with ethyl ether. The suspension which results is refrigerated for 1 hour. Then, the crystals which form are removed by filtration, dried in an evacuated desiccator, and dissolved in hexamethylphosphoramide (10% weight/volume). A portion of the resultant solution containing 1 mole of the acid salt, i.e. of sodium 11β-hydroxy-17α-methoxycarbonyloxyandrost-4-en-3-one-17β-carboxylate, is combined with 4 moles of chloromethyl iodide. The reaction mixture is maintained at room temperature for 3 hours, then is diluted to 10 times the original volume with ethyl acetate. The diluted reaction mixture is washed successively with 5% sodium thiosulfate, 3% sodium bicarbonate, and water.

The organic layer is separated, dried with magnesium sulfate and filtered. The filtrate is concentrated in vacuo to a foam. The foam is purified by crystallization from a suitable solvent (ethyl ether or tetrahydrofuran/hexane). There is thus obtained chloromethyl 11β-hydroxy-17α-methoxycarbonyloxyandrost-4-en-3-one-17β-carboxylate, melting at 171°-173° C. after crystallization; ir(KBr) 3000-2800 (C—H), 1760, 1748 (C═O), 1650 (C═C—C═O) $cm^{-1}$; nmr ($CDCl_3$) δ5.67(s, 1, C═CH), 5.82, 5.62 (ABq, J=5.5 Hz, 2, $OCH_2Cl$), 4.47(b, 1, CHOH); Anal. calcd. for $C_{23}H_{31}ClO$: C, 60.72; H, 6.87; Cl, 7.79. Found: C, 60.50; H, 7.06; Cl, 7.50. The product is characterized by the structural formula

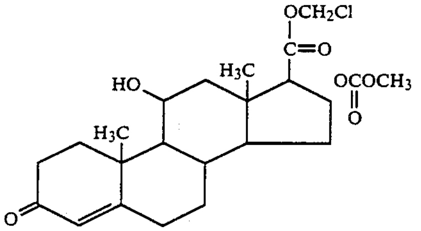

Substitution of an equivalent quantity of 17α-ethoxycarbonyloxy-11β-hydroxyandrost-4-en-3-one-17β-carboxylic acid for the steroidal acid employed above and substantial repetition of the foregoing procedure affords, as the intermediate salt, sodium 17α-ethoxycarbonyloxy-11β-hydroxyandrost-4-en-3-one-17β-carboxylate, and, as the final product, chloromethyl 17α-ethoxycarbonyloxy-11β-hydroxyandrost-4-en-3-one-17β-carboxylate, melting at 197°-200° C. after crystallization; ir (KBr) 3600-3200 (O—H), 3000-2800 (C—H), 1763, 1740 (C═O), 1650 (C═C—C═O) $cm^{-1}$; nmr ($CDCl_3$) δ5.7(s, 1, C═CH), 5.81, 5.62 (ABq, J=5 Hz, 2, —$OCH_2Cl$); Anal calcd. for $C_{24}H_{33}ClO_7$: C, 61.46; H, 7.09. Found: C, 61.58; H, 7.08.

In a similar manner, substitution of an equivalent quantity of 17α-butoxycarbonyloxy-11β-hydroxyandrost-4-en-3-one-17β-carboxylic acid for the steroidal acid employed in the first paragraph of this example and substantial repetition of the procedure there detailed affords, as the intermediate salt, sodium 17α-butoxycarbonyloxy-11β-hydroxyandrost-4-en-3-one-17β-carboxylate, and, as the final product, chloromethyl 17α-butoxycarbonyloxy-11β-hydroxyandrost-4-en-3-one-17β-carboxylate, melting at 98°-100° C. after crystallization; ir(KBr) 3600-3300 (O—H), 3000-2800 (C—H), 1765 ($O_2C$═O), 1735 (OC═O), 1650 (C═C—C═O) $cm^{-1}$; nmr($CDCl_3$) δ5.60 (2, ABq, J=4.5 Hz, —$OCH_2Cl$), 5.67 (1, s, C═CH), 4.45 (1, b, CHOH), 4.08 (2, t, J=6 Hz, $O_2COCH_2$—$CH_2$); Anal calcd. for $C_{26}H_{37}ClO_7$: C, 62.77; H, 7.44; Cl, 7.14. Found: C, 62.88; H, 7.23; Cl, 7.30.

Similarly, substituting an equivalent amount of 11β-hydroxy-17α-isopropoxycarbonyloxyandrost-4-en-3-one-17β-carboxylic acid for the steroidal acid employed in the first paragraph of this example and substantial repetition of the procedure there detailed affords, as the intermediate salt, sodium 11β-hydroxy-17α-isopropoxycarbonyloxyandrost-4-en-3-one-17β-carboxylate, and, as the final product, chloromethyl 11β-hydroxy-17α-isopropoxycarbonyloxyandrost-4-en-3-one-17β-carboxylate, melting at 183.5°-184.5° C. after recrystallization from tetrahydrofuran-hexane.

In a similar manner, an equivalent quantity of 17α-ethoxycarbonyloxy-11β-hydroxyandrost-4-en-3-one-17β-carboxylic acid is substituted for the steroidal acid and an equivalent quantity of butyl chloride is substituted for the chloromethyl iodide employed in the first paragraph of this example; and the procedure there detailed is substantially repeated, except that the step of washing with 5% sodium thiosulfate is eliminated. Obtained in this manner are the intermediate salt, sodium 17α-ethoxycarbonyloxy-11β-hydroxyandrost-4-en-3-one-17β-carboxylate, and the final product, butyl 17α-ethoxycarbonyloxy-11β-hydroxyandrost-4-en-3-one-17β-carboxylate. The final product after crystallization from acetone melts at 148°-149° C.; after chromatography and crystallization, ir(KBr) 3600-3200 (O—H), 3000-2800 (C—H), 1750 (2 C═O), 1670 (C═C—C═O) $cm^{-1}$; nmr ($CDCl_3$) δ5.64(s, 1, —C═CH), 4.46 (b, 1, CHOH), 4.32-4.95 (m, 4, $COOCH_2CH_3$+, $COOCH_2CH_2$—); Anal. calcd. for $C_{27}H_{40}O_7$: C, 67.99; H, 8.39. Found: C, 67.76; H, 7.74.

EXAMPLE 4

17α-Ethoxycarbonyloxy-11β-hydroxyandrost-4-en-3-one-17β-carboxylic acid (3 grams, 7.13 mmol6) is treated with 7.13 milliliters of 1M methanolic sodium hydroxide solution, and 500 milliliters of ethyl ether are then added to effect precipitation. The precipitate is separated by filtration and dried in an evacuated dessicator overnight to afford 2.71 grams (6.12 mmol) of the desired salt, i.e. sodium 17α-ethoxycarbonyloxy-11β-hydroxyandrost-4-en-3-one-17β-carboxylate, as a yellow powder. The salt is dissolved in 40 milliliters of hexamethylphosphoramide and chloromethyl methyl sulfide (2.36 grams, 24.5 mmol) is added slowly. A precipitate of sodium chloride forms in the reaction mixture within 1 minute. The reaction mixture is stirred at room temperature for 1 hour, then is diluted with ethyl acetate to a total volume of 200 milliliters and washed successively with 3% sodium bicarbonate and water. The organic layer is separated, dried with magnesium sulfate and filtered. The filtrate is concentrated in vacuo to an oil, and the oil is chromatographed from silica gel, using ethyl acetate, chloroform and acetic acid as eluants. The chromatographed product is crystallized from a mixture of ethyl ether and hexane to give white powdery crystals of methylthiomethyl 17α-ethoxycarbonyloxy-11β-hydroxyandrost-4-en-3-one-17β-carboxylate, melting at 133°-136° C. That product is characterized by the structural formula

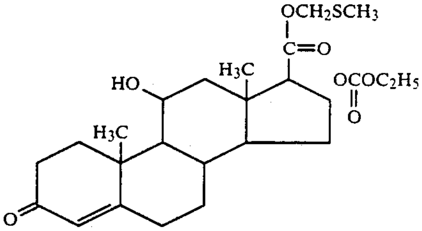

To a solution of methylthiomethyl 17α-ethoxycarbonyloxy-11β-hydroxyandrost-4-en-3-one-17β-carboxylate (0.48 gram, 1 mmol) in 2 milliliters of dichloromethane is added m-chloroperoxybenzoic acid (0.4 gram=0.34 gram of peracid, 2 mmol). An exothermic reaction ensues, which subsides quickly. The reaction mixture is stirred at room temperature for 1 hour. The precipitate which forms is removed by filtration and the filtrate is concentrated in vacuo to afford, as a white foam, methylsulfonylmethyl 17α-ethoxycarbonyloxy-11β-hydroxyandrost-4-en-3-one-17β-carboxylate. That product has the structural formula

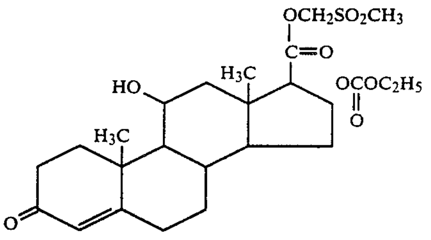

NMR ($CDCl_3$): δ5.07 (s, 2, $OC\underline{H}_2SO_2$), 2.97 (s, 3, $SO_2C\underline{H}_3$).

Repetition of the procedure described in the preceding paragraph, but using only 1 mmol of m-chloroperoxybenzoic acid, affords methylsulfinylmethyl 17β-ethoxycarbonyloxy-11β-hydroxyandrost-4-en-3-one-17β-carboxylate.

EXAMPLE 5A

Substitution of an equivalent quantity of one of the starting materials listed below for the hydrocortisone used in Example 1 and substantial repetition of the procedure there detailed affords the indicated products:

| STARTING MATERIAL | PRODUCT |
|---|---|
| fludrocortisone | 9α-fluoro-11β,17α-dihydroxy-androst-4-en-3-one-17β-carboxylic acid, m.p. 250-253° C. |
| betamethasone | 9α-fluoro-11β,17α-dihydroxy-16β-methylandrosta-1,4-dien-3-one-17β-carboxylic acid, m.p. 248-249° C. |
| dexamethasone | 9α-fluoro-11β,17α-dihydroxy-16α-methylandrosta-1,4-dien-3-one-17β-carboxylic acid, m.p. 275-278.5° C. |

EXAMPLE 5B

Substitution of an equivalent quantity of one of the starting materials listed below for the hydrocortisone used in Example 1 and substantial repetition of the procedure there detailed affords the indicated products:

| STARTING MATERIAL | PRODUCT |
|---|---|
| cortisone | 17α-hydroxyandrost-4-en-3,11-dione-17β-carboxylic acid |
| chloroprednisone | 6α-chloro-17α-hydroxyandrosta-1,4-dien-3,11-dione-17β-carboxylic acid |
| flumethasone | 6α,9α-difluoro-11β, 17α-dihydroxy-16α-methylandrosta-1,4-dien-3-one-17β-carboxylic acid |
| fluprednisolone | 6α-fluoro-11β,17α-dihydroxy-androsta-1,4-dien-3-one-17β-carboxylic acid |
| meprednisone | 17α-hydroxy-16β-methylandrosta-1,4-dien-3,11-dione-17β-carboxylic acid |
| methyl prednisolone | 11α,17β-dihydroxy-6α-methyl-androsta-1,4-dien-3-one-17β-carboxylic acid |
| paramethasone | 6α-fluoro-11β,17α-dihydroxy-16α-methylandrosta-1,4-dien-3-one-17β-carboxylic acid |
| prednisolone | 11β,17α-dihydroxyandrosta-1,4-dien-3-one-17β-carboxylic acid |
| prednisone | 17α-hydroxyandrosta-1,4-dien-3,11-dione-17β-carboxylic acid |
| triamcinolone | 9α-fluoro-11β,16α,17α-trihydroxy-androsta-1,4-dien-3-one-17β-carboxylic acid |

EXAMPLE 6A

Following the general procedure of Example 2 and substituting therein the appropriate reactants affords the following novel intermediates of the present invention:

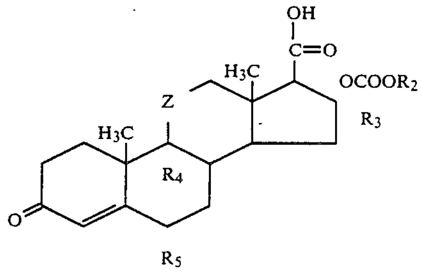

Compounds

| Compound No. | $R_2$ | $R_3$ | $R_4$ | $R_5$ | Z | Δ | m.p. |
|---|---|---|---|---|---|---|---|
| 6A-1 | $CH_2C_6H_5$ | H | H | H | 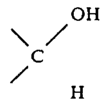 | 4 | 183-184° C. (ethanol) |
| 6A-2 | $C_2H_5$ | H | F | H | 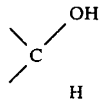 | 4 | 190-191° C. (THF/hexane) |
| 6A-3 | $C_2H_5$ | β-$CH_3$ | F | H | 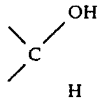 | 1,4 | 128-129° C. (THF/hexane) |

-continued

| Compound No. | $R_2$ | $R_3$ | $R_4$ | $R_5$ | Z | Δ | m.p. |
|---|---|---|---|---|---|---|---|
| 6A-4 | $C_2H_5$ | α-$CH_3$ | F | H | 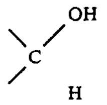 | 1,4 | 143–144.5° C. (THF/hexane) |
| 6A-5 | iso-$C_3H_7$ | α-$CH_3$ | F | H | 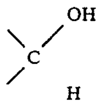 | 1,4 | 154.5–156° C. (THF/hexane) |
| 6A-6 | iso-$C_4H_9$ | H | H | H | 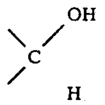 | 4 | 125–126° C. (THF/hexane) |
| 6A-7 | iso-$C_3H_7$ | β-$CH_3$ | F | H | 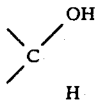 | 1,4 | 171.5–172.5° C. (THF/hexane) |
| 6A-8 | n-$C_3H_7$ | H | H | H | 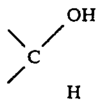 | 4 | 156–157° C. (THF/hexane) |
| 6A-9 | n-$C_3H_7$ | α-$CH_3$ | F | H | 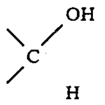 | 1,4 | 157–158° C. (THF/hexane) |
| 6A-10 | 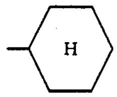 | H | H | H | 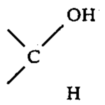 | 4 | 156–157.5° C. (ether/hexane) |
| 6A-11 | $CH_3$ | α-$CH_3$ | F | H | 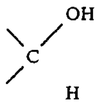 | 1,4 | 180–182° C. (ethyl acetate) |
| 6A-12 | n-$C_5H_{11}$ | α-$CH_3$ | F | H | 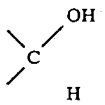 | 1,4 | 138.5–139.5° C. (THF/hexane) |
| 6A-13 | $C_2H_5$ | α-$CH_3$ | F | F | 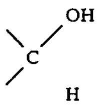 | 1,4 | 157–158° C. (decomp.) (THF/hexane) |
| 6A-14 | $C_6H_5$ | α-$CH_3$ | F | H | 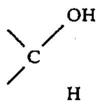 | 1,4 | 246–248° C. (THF/hexane) |
| 6A-15 | $CH_2CH_2Cl$ | α-$CH_3$ | F | H | 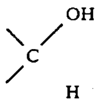 | 4 | 93–94° C. (THF/hexane) |

6A-1 to 6A-15 above can be named as follows:

6A-1: 17α-benzyloxycarbonyloxy-11β-hydroxyandrost-4-en-3-one-17β-carboxylic acid 6A-2: 17α-ethoxycarbonyloxy-9α-fluoro-11β-hydroxyandrost-4-en-3-one-17β-carboxylic acid 6A-3: 17α-ethoxycarbonyloxy-9α-fluoro-11β-hydroxy-16β-methylandrosta-1,4-dien-3-one-17β-carboxylic acid 6A-4: 17α-ethoxycarbonyloxy-9α-fluoro-11β-hydroxy-16α-methylandrosta-1,4-dien-3-one-17β-carboxylic acid 6A-5: 9α-fluoro-11β-hydroxy-17α-isopropoxycarbonyloxy-16α-methylandrosta-1,4-dien-3-one-17β-carboxylic acid 6A-6: 11β-hydroxy-17α-isobutoxycarbonyloxyandrost-4-en-3-one-17β-carboxylic acid 6A-7: 9α-fluoro-11β-hydroxy-17α-isopropoxycarbonyloxy-16β-methylandrosta-1,4-dien-3-one-17β-carboxylic acid 6A-8: 11β-hydroxy-17α-propoxycarbonyloxyandrost-4-en-3-one-17β-carboxylic acid 6A-9: 9α-fluoro-11β-hydroxy-16α-methyl-17α-propoxycarbonyloxyandrosta-1,4-dien-3-one-17β-carboxylic acid 6A-10: 17α-cyclohexyloxycarbonyloxy-11β-hydroxyandrost-4-en-3-one-17β-carboxylic acid 6A-11: 9α-fluoro-11β-hydroxy-17α-methoxycarbonyloxy-16α-methylandrosta-1,4-dien-3-one-17β-carboxylic aicd 6A-12: 9α-fluoro-11β-hydroxy-16α-methyl-17α-n-pentyloxycarbonyloxyandrosta-1,4-dien-3-one-17β-carboxylic acid 6A-13: 17α-ethoxycarbonyloxy-6α,9α-difluoro-11β-hydroxy-16α-methyllandrosta-1,4-dien-3-one-17β-carboxylic acid 6A-14: 9α-fluoro-11β-hydroxy-16α-methyl-17α-phenoxycarbonyloxyandrosta-1,4-dien-3-one-17β-carboxylic acid 6A-15: 17α-(2-chloroethoxycarbonyloxy)-9α-fluoro-11β-hydroxy-16α-methylandrosta-1,4-dien-3-one-17β-carboxylic acid

EXAMPLE 6B

Following the general procedure of Example 2 and substituting therein the appropriate reactants affords the following novel intermediates of the present invention:

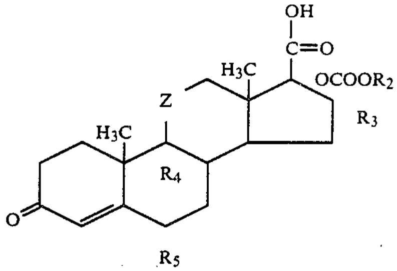

| Compound No. | $R_2$ | $R_3$ | $R_4$ | $R_5$ | Z | Δ |
|---|---|---|---|---|---|---|
| 6B-1 | $C_2H_5$ | H | H | H | 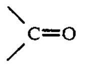 | 4 |
| 6B-2 | $CH_3$ | H | H | H | 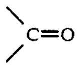 | 4 |
| 6B-3 | $CH_3$ | H | F | H | 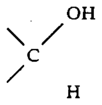 | 4 |
| 6B-4 | $C_2H_5$ | α-$CH_3$ | F | F | 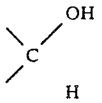 | 1,4 |
| 6B-5 | $C_2H_5$ | H | H | F | 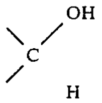 | 1,4 |
| 6B-6 | $C_2H_5$ | β-$CH_3$ | H | H | 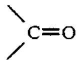 | 1,4 |
| 6B-7 | $CH_2CCl_3$ | H | H | H | 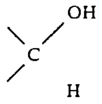 | 4 |
| 6B-8 | $C_2H_5$ | α-$CH_3$ | H | F | 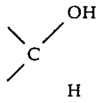 | 1,4 |
| 6B-9 | $C_2H_5$ | H | H | H | 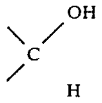 | 1,4 |

-continued
| Compound No. | $R_2$ | $R_3$ | $R_4$ | $R_5$ | Z | Δ |
|---|---|---|---|---|---|---|
| 6B-10 | $C_2H_5$ | H | H | H | 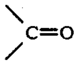 | 1,4 |
| 6B-11 | $C_2H_5$ | α-$OCOOC_2H_5$ | F | H | 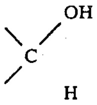 | 1,4 |
| 6B-12 | $CH_2Cl$ | α-$CH_3$ | F | H | 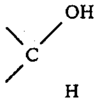 | 1,4 |
| 6B-13 | $CH_2CH_2Cl$ | α-$CH_3$ | F | H | 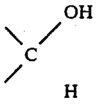 | 1,4 |
| 6B-14 | $C_2H_5$ | H | H | Cl | 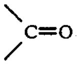 | 1,4 |
| 6B-15 | $C_6H_5$ | H | H | H | 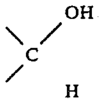 | 4 |
| 6B-16 | 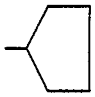 | H | H | H | 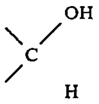 | 4 |
| 6B-17 | 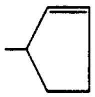 | H | H | H | 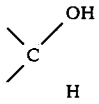 | 4 |
| 6B-18 | $CH{=}CH_2$ | H | H | H | 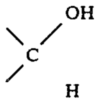 | 4 |
| 6B-19 | $CH_2OCH_3$ | H | H | H | 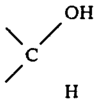 | 4 |
| 6B-20 | $CH_2SCH_3$ | H | H | H | 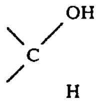 | 4 |
| 6B-21 | $CH_2CH_2NHCOCH_3$ | H | H | H | 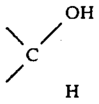 | 4 |
| 6B-22 | $CH_2CH_2OCOCH_3$ | H | H | H | 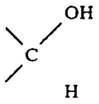 | 4 |
| 6B-23 | $C_2H_5$ | H | H | $CH_3$ | 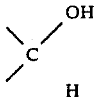 | 1,4 |

-continued

| Compound No. | $R_2$ | $R_3$ | $R_4$ | $R_5$ | Z | Δ |
|---|---|---|---|---|---|---|
| 6B-24 | $CH_2SO_2CH_3$* | H | H | H | 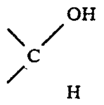 | 4 |
| 6B-25 | $CH_2SOCH_3$* | H | H | H | 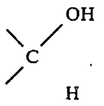 | 4 |

*prepared from 6B-20 by subsequent reaction with m-chloroperbenzoic acid.

EXAMPLE 6C

Following the general procedure of Example 2 and substituting therein the appropriate reactants affords the following novel intermediates of the present invention:

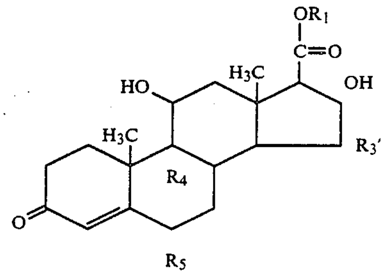

(VI)

| Compound No. | $R_2$ | $R_3$ | $R_4$ | $R_5$ | Z | Δ | m.p. |
|---|---|---|---|---|---|---|---|
| 6C-1 | $-CH_2CH=CH_2$ | α-$CH_3$ | F | H | 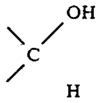 | 1,4 | 227-229° C. (THF/hexane) |
| 6C-2 | $-CH_2CH_2CH_3$ | α-$CH_3$ | F | F | 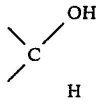 | 1,4 | 148-155° C. (decomp.) (ethanol/water) |
| 6C-3 | 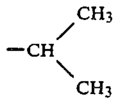 | α-$CH_3$ | F | F | 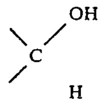 | 1,4 | 157-159° C. (ethanol/water) |
| 6C-4 | $-C_2H_5$ | α-$CH_3$ | H | F | 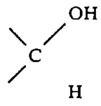 | 1,4 | 105-108° C. (THF/n-hexane) |
| 6C-5 | $-(CH_2)_2CH_3$ | α-$CH_3$ | H | F | 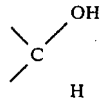 | 1,4 | 150-152° C. (THF/n-hexane) |
| 6C-6 | 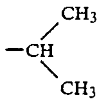 | α-$CH_3$ | H | F | 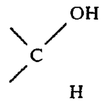 | 1,4 | 124-127° C. (THF/n-hexane) |
| 6C-7 | $-CH_3$ | H | H | H | 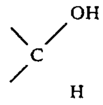 | 1,4 | 178-180° C. (THF/n-hexane) |
| 6C-8 | $-CH_3$ | α-$CH_3$ | H | F | 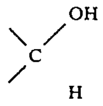 | 1,4 | 182-183° C. (THF/n-hexane) |

-continued

| Compound No. | R2 | R3 | R4 | R5 | Z | Δ | m.p. |
|---|---|---|---|---|---|---|---|
| 6C-9 | $-C_2H_5$ | H | H | H | 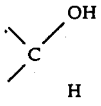 | 1,4 | 153-156° C. (THF/n-hexane) |
| 6C-10 | $-CH_3$ | β-$CH_3$ | F | H | 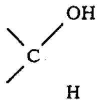 | 1,4 | 186-188 (decomposition) (THF/n-hexane) |
| 6C-11 | $-CH_2CH_2CH_3$ | β-$CH_3$ | F | H | 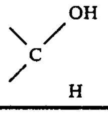 | 1,4 | 143-144.5° C. (THF/n-hexane) |

The foregoing compounds can be named as follows:

6C-1: 17α-allyloxycarbonyloxy-9α-fluoro-11β-hydroxy-16α-methylandrosta-1,4-dien-3-one-17β-carboxylic acid 6C-2: 6α,9α-difluoro-11β-hydroxy-16α-methyl-17α-n-propoxycarbonyloxyandrosta-1,4-dien-3-one-17β-carboxylic acid 6C-3: 6α,9α-difluoro-11β-hydroxy-17α-isopropoxycarbonyloxy-16α-methylandrosta-1,4-dien-3-one-17β-carboxylic acid 6C-4: 17α-ethoxycarbonyloxy-6α-fluoro-11β-hydroxy-16α-methylandrosta-1,4-dien-3-one-17β-carboxylic acid 6C-5: 6α-fluoro-11β-hydroxy-16α-methyl-17α-n-propoxycarbonyloxyandrosta-1,4-dien-3-one-17β-carboxylic acid 6C-6: 6α-fluoro-11β-hydroxy-17α-isopropoxycarbonyloxy-16α-methylandrosta-1,4-dien-3-one-17β-carboxylic acid 6C-7: 11β-hydroxy-17α-methoxycarbonyloxyandrosta-1,4-dien-3-one-17β-carboxylic acid 6C-8: 6α-fluoro-11β-hydroxy-17α-methoxycarbonyloxy-16α-methylandrosta-1,4-dien-3-one-17β-carboxylic acid 6C-9: 17α-ethoxycarbonyloxy-11β-hydroxyandrosta-1,4-dien-3-one-17β-carboxylic acid 6C-10: 9α-fluoro-11β-hydroxy-17α-methoxycarbonyloxy-16β-methylandrosta-1,4-dien-3-one-17β-carboxylic acid 6C-11: 9α-fluoro-11β-hydroxy-16β-methyl-17α-n-propoxycarbonyloxyandrosta-1,4-dien-3-one-17β-carboxylic acid

EXAMPLE 7A

Following the general procedure of Example 3 and substituting therein the appropriate reactants affords the following compounds:

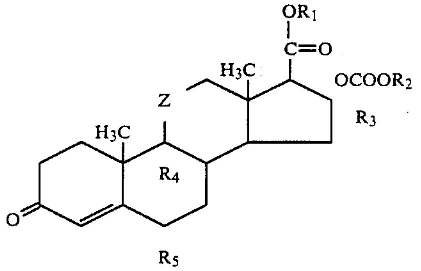

| Compound No. | R1 | R2 | R3 | R4 | R5 | Z | Δ | m.p. |
|---|---|---|---|---|---|---|---|---|
| 7A-1 | $CH_2Cl$ | $C_2H_5$ | H | F | H | 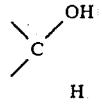 | 4 | 228-229° C. (THF/hexane) |
| 7A-2 | $CH_2Cl$ | $C_2H_5$ | β-$CH_3$ | F | H | 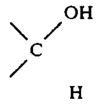 | 1,4 | 220-221° C. (THF/hexane) |
| 7A-3 | $CH_2Cl$ | $C_2H_5$ | α-$CH_3$ | F | H | 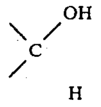 | 1,4 | 230-235° C. (THF/hexane) |
| 7A-4 | $CH_2Cl$ | $C_2H_5$ | H | H | H | 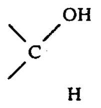 | 1,4 | 220.5-223.5° C. (THF/hexane) |

-continued

| Compound No. | $R_1$ | $R_2$ | $R_3$ | $R_4$ | $R_5$ | Z | Δ | m.p. |
|---|---|---|---|---|---|---|---|---|
| 7A-5 | $CH_2Cl$ | iso-$C_3H_7$ | H | H | H | 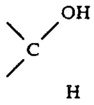 | 1,4 | 197–198° C. (THF/hexane) |
| 7A-6 | $CH_2Cl$ | $C_2H_5$ | H | F | H | 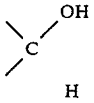 | 1,4 | 245–248° C. (THF/hexane) |
| 7A-7 | $CH_2Cl$ | iso-$C_3H_7$ | α-$CH_3$ | F | H | 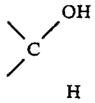 | 1,4 | 184.5–186° C. (THF/hexane) |
| 7A-8 | $CH_2Cl$ | iso-$C_3H_7$ | β-$CH_3$ | F | H | 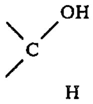 | 1,4 | 174–175.5° C. (THF) |
| 7A-9 | $CH_2Cl$ | iso-$C_4H_9$ | H | H | H | 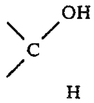 | 4 | 140–141° C. (THF/isopropyl ether) |
| 7A-10 | $CH_2Cl$ | 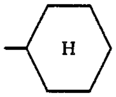 | H | H | H | 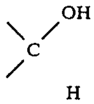 | 4 | 148–150° C. (isopropyl ether hexane) |
| 7A-11 | $CH_2Cl$ | n-$C_3H_7$ | H | H | H | 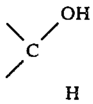 | 4 | 181–182° C. (THF/hexane) |
| 7A-12 | $CH_2Cl$ | n-$C_3H_7$ | α-$CH_3$ | F | H | 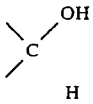 | 1,4 | 176–176.5° C. (THF/hexane) |
| 7A-13 | $CH_3$ | iso-$C_3H_7$ | H | H | H | 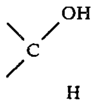 | 4 | 211.5–213.5° C. (THF/hexane) |
| 7A-14 | $CH_2OC_2H_5$ | iso-$C_3H_7$ | H | H | H | 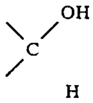 | 4 | 137–138° C. (THF/hexane) |
| 7A-15 | $CH_2Cl$ | $CH_2$— 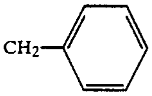 | H | H | H | 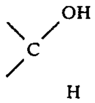 | 4 | 182–183° C. (ethanol) |
| 7A-16* | $CH_3$<br>CHCl | iso-$C_3H_7$ | H | H | H | 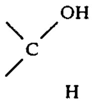 | 4 | 181–182.5° C. (THF/hexane) |
| | $CH_3$<br>CHCl | iso-$C_3H_7$ | H | H | H | 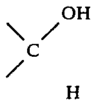 | 4 | 199–200° C. (THF/hexane) |
| 7A-17 | $CH_2CO_2C_2H_5$ | iso-$C_3H_7$ | H | H | H | 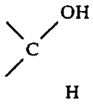 | 4 | 73–74° C. (isopropyl ether) |

-continued

| Compound No. | $R_1$ | $R_2$ | $R_3$ | $R_4$ | $R_5$ | Z | Δ | m.p. |
|---|---|---|---|---|---|---|---|---|
| 7A-18* | 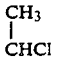 | iso-$C_3H_7$ | β-$CH_3$ | F | H | 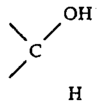 | 1,4 | 167.5–169° C. (THF/hexane) |
| | 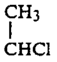 | iso-$C_3H_7$ | β-$CH_3$ | F | H | 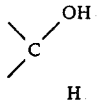 | 1,4 | 163–164° C. (THF/hexane) |
| 7A-19 | $CH_2Cl$ | iso-$C_3H_7$ | β-$CH_3$ | F | H | 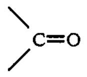 | 1,4 | 200–201° C. (THF/isopropyl ether) |
| 7A-20 | $CH_2Cl$ | $C_2H_5$ | α-$CH_3$ | F | H | 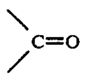 | 1,4 | 138–140° C. (THF/isopropyl ether) |
| 7A-21 | $CH_2Cl$ | $CH_3$ | α-$CH_3$ | F | H | 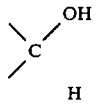 | 1,4 | 260–263° C. (THF/hexane) |
| 7A-22 | $CH_2F$ | iso-$C_3H_7$ | H | H | H | 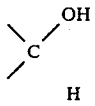 | 4 | 207.5–210° C. (THF/hexane) |
| 7A-23 | $CH_2Cl$ | n-$C_5H_{11}$ | α-$CH_3$ | F | H | 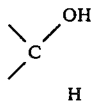 | 1,4 | 176–177° C. (THF/hexane) |
| 7A-24 | $CH_2Cl$ | $C_2H_5$ | 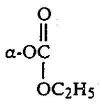 | H | F | 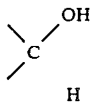 | 1,4 | 153–154° C. (THF/hexane) |
| 7A-25 | $CH_2F$ | $C_2H_5$ | α-$CH_3$ | F | H | 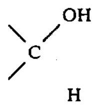 | 1,4 | 239–240.5° C. (THF/hexane) |
| 7A-26 | $CH_2OCOCH_3$ | $C_2H_5$ | H | H | H | 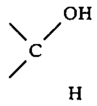 | 4 | NMR ($CDCl_3$) δ5.76(s,2, OC$\underline{H}_2$O), 2.01 (s,3, COC$\underline{H}_3$) |
| 7A-27 | $CH_2Cl$ | $C_2H_5$ | α-$CH_3$ | F | F | 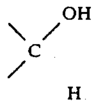 | 1,4 | 195–197° C. (THF/hexane) |
| 7A-28 | $CH_2CH_2Cl$ | $C_2H_5$ | α-$CH_3$ | F | H | 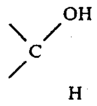 | 1,4 | 243–245° C. (THF/hexane) |
| 7A-29 | $CH_3$ | $C_2H_5$ | α-$CH_3$ | F | H | 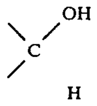 | 1,4 | 258.5–262.5° C. (THF/hexane) |

-continued

| Compound No. | $R_1$ | $R_2$ | $R_3$ | $R_4$ | $R_5$ | Z | Δ | m.p. |
|---|---|---|---|---|---|---|---|---|
| 7A-30 | $CH_2CH_2Cl$ | iso-$C_3H_7$ | H | H | H | 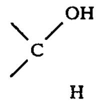 | 4 | 188.5–189.5° C. (THF/hexane) |

*diastereomers

The foregoing compounds can be named as follows:

7A-1: chloromethyl 17α-ethoxycarbonyloxy-9α-fluoro-11β-hydroxyandrost-4-en-3-one-17β-carboxylate 7A-2: chloromethyl 17α-ethoxycarbonyloxy-9α-fluoro-11β-hydroxy-16β-methylandrosta-1,4-dien-3-one-17β-carboxylate 7A-3: chloromethyl 17α-ethoxycarbonyloxy-9α-fluoro-11β-hydroxy-16α-methylandrosta-1,4-dien-3-one-17β-carboxylate 7A-4: chloromethyl 17β-ethoxycarbonyloxy-11β-hydroxyandrosta-1,4-dien-3-one-17β-carboxylate 7A-5: chloromethyl 11β-hydroxy-17α-isopropoxycarbonyloxyandrosta-1,4-dien-3-one-17β-carboxylate 7A-6: chloromethyl 17α-ethoxycarbonyloxy-9α-fluoro-11β-hydroxyandrosta-1,4-dien-3-one-17β-carboxylate 7A-7: chloromethyl 9α-fluoro-11β-hydroxy-17α-isopropoxycarbonyloxy-16α-methylandrosta-1,4-dien-3-one-17β-carboxylate 7A-8: chloromethyl 9α-fluoro-11β-hydroxy-17α-isopropoxycarbonyloxy-16β-methylandrosta-1,4-dien-3-one-17β-carboxylate 7A-9: chloromethyl 11β-hydroxy-17α-isobutoxycarbonyloxyandrost-4-en-3-one-17β-carboxylate 7A-10: chloromethyl 17α-cyclohexyloxycarbonyloxy-11β-hydroxyandrost-4-en-3-one-17β-carboxylate 7A-11: chloromethyl 11β-hydroxy-17α-propoxycarbonyloxyandrost-4-en-3-one-17β-carboxylate 7A-12: chloromethyl 9α-fluoro-11β-hydroxy-16α-methyl-17α-propoxycarbonyloxyandrosta-1,4-dien-3-one-17β-carboxylate 7A-13: methyl 11β-hydroxy-17α-isopropoxycarbonyloxyandrost-4-en-3-one-17β-carboxylate 7A-14: ethoxymethyl 11β-hydroxy-17α-isopropoxycarbonyloxyandrost-4-en-3-one-17β-carboxylate 7A-15: chloromethyl 17α-benzyloxycarbonyloxy-11β-hydroxyandrost-4-en-3-one-17β-carboxylate 7A-16: 1-chloroethyl 11β-hydroxy-17α-isopropoxycarbonyloxyandrost-4-en-3-one-17β-carboxylate 7A-17: ethoxycarbonylmethyl 11β-hydroxy-17α-isopropoxycarbonyloxyandrost-4-en-3-one-17βcarboxylate 7A-18: 1-chloroethyl 9α-fluoro-11β-hydroxy-17α-isopropoxycarbonyloxy-16β-methylandrosta-1,4-dien-3-one-17β-carboxylate 7A-19: chloromethyl 9α-fluoro-17α-isopropoxycarbonyloxy-16β-methylandrosta-1,4-dien-3,11-dione-17-carboxylate 7A-20: chloromethyl 9α-fluoro-17α-isopropoxycarbonyloxy-16α-methylandrosta-1,4-dien-3,11-dione-17-carboxylate 7A-21: chloromethyl 9α-fluoro-11β-hydroxy-17α-methoxycarbonyloxy-16α-methylandrost-1,4-dien-3-one-17β-carboxylate 7A-22: fluoromethyl 11β-hydroxy-17α-isopropoxycarbonyloxyandrost-4-en-3-one-17β-carboxylate 7A-23: chloromethyl 9α-fluoro-11β-hydroxy-16α-methyl-17α-pentyloxycarbonyloxyandrosta-1,4-dien-3-one-17β-carboxylate 7A-24: chloromethyl 16α,17α-di(ethoxycarbonyloxy)-6α-fluoro-11β-hydroxyandrosta-1,4-dien-3-one-17β-carboxylate 7A-25: fluoromethyl 17α-ethoxycarbonyloxy-9α-fluoro-11β-hydroxy-16α-methylandrosta-1,4-dien-3-one-17β-carboxylate 7A-26: acetoxymethyl 17α-ethoxycarbonyloxy-11β-hydroxyandrost-4-en-3-one-17β-carboxylate 7A-27: chloromethyl 17α-ethoxycarbonyloxy-6α,9α-difluoro-11β-hydroxy-16α-methylandrosta-1,4-dien-3-one-17β-carboxylate 7A-28: 2-chloroethyl 17α-ethoxycarbonyloxy-9α-fluoro-11β-hydroxy-16α-methylandrosta-1,4-dien-3-one-17β-carboxylate 7A-29: methyl 17α-ethoxycarbonyloxy-9α-fluoro-11β-hydroxy-16α-methylandrosta-1,4-dien-3-one-17β-carboxylate 7A-30: 2-chloroethyl 11β-hydroxy-17α-isopropoxycarbonyloxyandrost-4-en-3-one-17β-carboxylate

EXAMPLE 7B

Following the general procedure of Examples 3 or 4 and substituting therein the appropriate reactants affords the following comppounds:

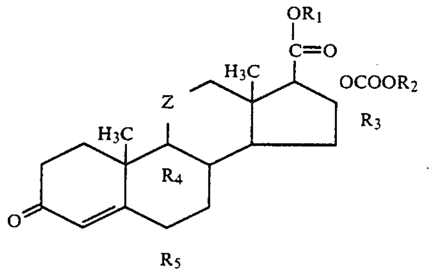

| Compound No. | $R_1$ | $R_2$ | $R_3$ | $R_4$ | $R_5$ | Z | Δ |
|---|---|---|---|---|---|---|---|
| 7B-1 | $C_2H_5$ | $C_2H_5$ | H | H | H | 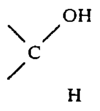 | 4 |

-continued
| Compound No. | $R_1$ | $R_2$ | $R_3$ | $R_4$ | $R_5$ | Z | Δ |
|---|---|---|---|---|---|---|---|
| 7B-2 | $C_4H_9$ | $CH_2C_6H_5$ | H | H | H | 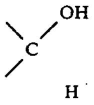 | 4 |
| 7B-3 | $CH_2COOC_2H_5$ | $C_2H_5$ | H | H | H | 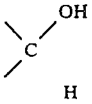 | 4 |
| 7B-4 | $CH_2OCOCH_3$ | $C_2H_5$ | H | H | H | 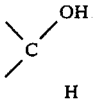 | 4 |
| 7B-5 | $CH_2Cl$ | $C_6H_5$ | H | H | H | 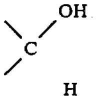 | 4 |
| 7B-6 | $CH_2Cl$ | 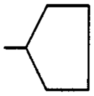 | H | H | H | 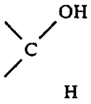 | 4 |
| 7B-7 | $CH_2Cl$ | $CH_2SCH_3$ | H | H | H | 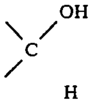 | 4 |
| 7B-8 | $C_4H_9$ | $C_2H_5$ | H | H | H | 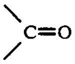 | 4 |
| 7B-9 | $CH_2Cl$ | $CH_3$ | H | H | H | 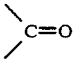 | 4 |
| 7B-10 | $CH_2Cl$ | $C_2H_5$ | H | H | H | 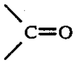 | 4 |
| 7B-11 | $CH_2SCH_3$ | $C_2H_5$ | H | H | H | 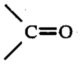 | 4 |
| 7B-12 | $CH_2SO_2CH_3$ | $C_2H_5$ | H | H | H | 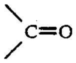 | 4 |
| 7B-13 | $CH_2SOCH_3$ | $C_2H_5$ | H | H | H | 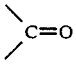 | 4 |
| 7B-14 | $CH_2Cl$ | $CH_3$ | H | F | H | 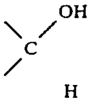 | 4 |
| 7B-15 | $CH_2SCH_3$ | $C_2H_5$ | H | F | H | 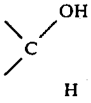 | 4 |

-continued
| Compound No. | $R_1$ | $R_2$ | $R_3$ | $R_4$ | $R_5$ | Z | Δ |
|---|---|---|---|---|---|---|---|
| 7B-16 | $CH_2SO_2CH_3$ | $C_2H_5$ | H | F | H | 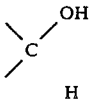 | 4 |
| 7B-17 | $CH_2SCH_3$ | $C_2H_5$ | β-$CH_3$ | F | H | 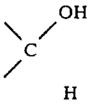 | 1,4 |
| 7B-18 | $CH_2SO_2CH_3$ | $C_2H_5$ | β-$CH_3$ | F | H | 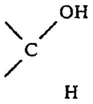 | 1,4 |
| 7B-19 | $CH_2Cl$ | $C_2H_5$ | H | H | Cl | 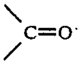 | 1,4 |
| 7B-20 | $CH_2SCH_3$ | $C_2H_5$ | H | H | Cl | 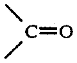 | 1,4 |
| 7B-21 | $CH_2SO_2CH_3$ | $C_2H_5$ | H | H | Cl | 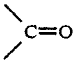 | 1,4 |
| 7B-22 | $CH_2SCH_3$ | $C_2H_5$ | α-$CH_3$ | F | H | 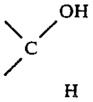 | 1,4 |
| 7B-23 | $CH_2SO_2CH_3$ | $C_2H_5$ | α-$CH_3$ | F | H | 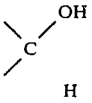 | 1,4 |
| 7B-24 | $CH_2Cl$ | $C_2H_5$ | α-$CH_3$ | F | F | 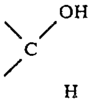 | 1,4 |
| 7B-25 | $CH_2SCH_3$ | $C_2H_5$ | α-$CH_3$ | F | F | 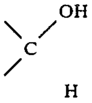 | 1,4 |
| 7B-26 | $CH_2SO_2CH_3$ | $C_2H_5$ | α-$CH_3$ | F | F | 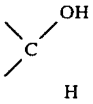 | 1,4 |
| 7B-27 | $CH_2Cl$ | $C_2H_5$ | H | H | F | 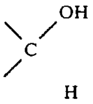 | 1,4 |
| 7B-28 | $CH_2SCH_3$ | $C_2H_5$ | H | H | F | 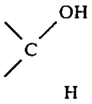 | 1,4 |
| 7B-29 | $CH_2SO_2CH_3$ | $C_2H_5$ | H | H | F | 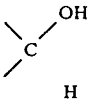 | 1,4 |

-continued
| Compound No. | $R_1$ | $R_2$ | $R_3$ | $R_4$ | $R_5$ | Z | Δ |
|---|---|---|---|---|---|---|---|
| 7B-30 | $CH_2Cl$ | $C_2H_5$ | β-$CH_3$ | H | H | 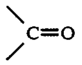 | 1,4 |
| 7B-31 | $CH_2SCH_3$ | $C_2H_5$ | β-$CH_3$ | H | H | 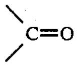 | 1,4 |
| 7B-32 | $CH_2SO_2CH_3$ | $C_2H_5$ | β-$CH_3$ | H | H | 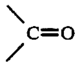 | 1,4 |
| 7B-33 | $CH_2Cl$ | $C_2H_5$ | H | H | $CH_3$ | 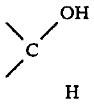 | 1,4 |
| 7B-34 | $CH_2SCH_3$ | $C_2H_5$ | H | H | $CH_3$ | 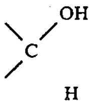 | 1,4 |
| 7B-35 | $CH_2SO_2CH_3$ | $C_2H_5$ | H | H | $CH_3$ | 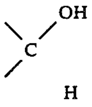 | 1,4 |
| 7B-36 | $CH_2Cl$ | $C_2H_5$ | α-$CH_3$ | H | F | 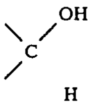 | 1,4 |
| 7B-37 | $CH_2SCH_3$ | $C_2H_5$ | α-$CH_3$ | H | F | 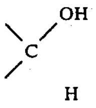 | 1,4 |
| 7B-38 | $CH_2SO_2CH_3$ | $C_2H_5$ | α-$CH_3$ | H | F | 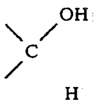 | 1,4 |
| 7B-39 | $CH_2SCH_3$ | $C_2H_5$ | H | H | H | 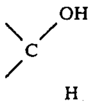 | 1,4 |
| 7B-40 | $CH_2SO_2CH_3$ | $C_2H_5$ | H | H | H | 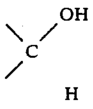 | 1,4 |
| 7B-41 | $CH_2Cl$ | $C_2H_5$ | H | H | H | 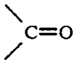 | 1,4 |
| 7B-42 | $CH_2SCH_3$ | $C_2H_5$ | H | H | H | 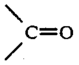 | 1,4 |
| 7B-43 | $CH_2SO_2CH_3$ | $C_2H_5$ | H | H | H | 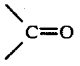 | 1,4 |

-continued
| Compound No. | $R_1$ | $R_2$ | $R_3$ | $R_4$ | $R_5$ | Z | Δ |
|---|---|---|---|---|---|---|---|
| 7B-44 | $CH_2Cl$ | $C_2H_5$ | α-$OCOOC_2H_5$ | F | H | 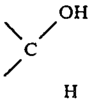 | 1,4 |
| 7B-45 | $CH_2SCH_3$ | $C_2H_5$ | α-$OCOOC_2H_5$ | F | H | 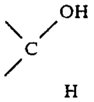 | 1,4 |
| 7B-46 | $CH_2SO_2CH_3$ | $C_2H_5$ | α-$OCOOC_2H_5$ | F | H | 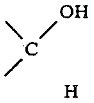 | 1,4 |
| 7B-47 | $CH_2Cl$ | $C_2H_5$ | α-OH | H | F | 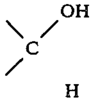 | 1,4 |
| 7B-48 | $CH_2Cl$ | 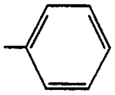 | α-$CH_3$ | F | H | 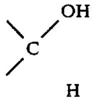 | 1,4 |
| 7B-49 | $CH_2Cl$ | $CH_2CH_2Cl$ | α-$CH_3$ | F | H | 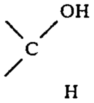 | 1,4 |
| 7B-50 | $CH_3$ | $CH_2Cl$ | α-$CH_3$ | F | H | 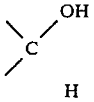 | 1,4 |
| 7B-51 | $C_4H_9$ | $CH_2CCl_3$ | H | H | H | 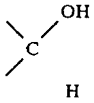 | 4 |
| 7B-52 | $CH_2CON(C_2H_5)_2$ | $C_2H_5$ | H | H | H | 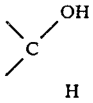 | 4 |
| 7B-53 | 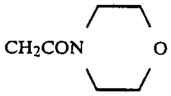 | $CH_3$ | H | H | H | 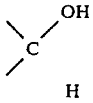 | 4 |
| 7B-54 | $C_6H_5$ | $C_2H_5$ | H | H | H | 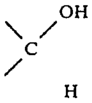 | 4 |
| 7B-55 | $CH_2C_6H_5$ | $CH_3$ | H | H | H | 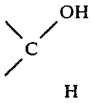 | 4 |
| 7B-56 | 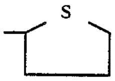 | $C_2H_5$ | H | H | H | 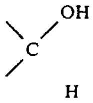 | 4 |
| 7B-57 | $CH_2Cl$ | 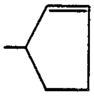 | H | H | H | 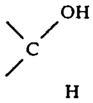 | 4 |

-continued

| Compound No. | $R_1$ | $R_2$ | $R_3$ | $R_4$ | $R_5$ | Z | Δ |
|---|---|---|---|---|---|---|---|
| 7B-58 | $CH_2Cl$ | $CH{=}CH_2$ | H | H | H | 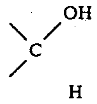 | 4 |
| 7B-59 | $CH_2Cl$ | $CH_2OCH_3$ | H | H | H | 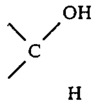 | 4 |
| 7B-60 | $CH_2Cl$ | $CH_2CH_2NHCOCH_3$ | H | H | H | 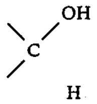 | 4 |
| 7B-61 | $CH_2Cl$ | $CH_2CH_2OCOCH_3$ | H | H | H | 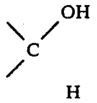 | 4 |
| 7B-62 | 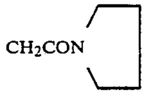 | $C_2H_5$ | H | H | H | 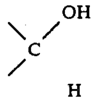 | 4 |
| 7B-63 | $CH_2Cl$ | $CH_2SO_2CH_3$* | H | H | H | 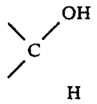 | 4 |
| 7B-64 | $CH_2Cl$ | $CH_2SOCH_3$* | H | H | H | 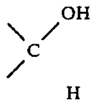 | 4 |

*prepared from Example 6B-24 and 6B-25 respectively by reaction with $ClCH_2I$, or from Example 7B-7 by reaction with m-chloroperbenzoic acid.

EXAMPLE 7C

Following the general procedure of Example 3 and substituting therein the appropriate reactants affords the following compounds:

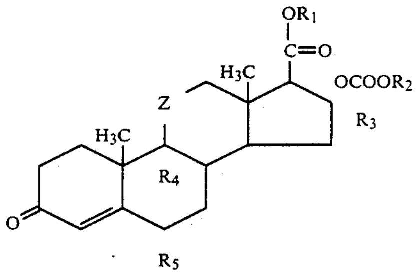

| Compound No. | $R_1$ | $R_2$ | $R_3$ | $R_4$ | $R_5$ | Z | Δ | m.p. |
|---|---|---|---|---|---|---|---|---|
| 7C-1 | $-CH_2Cl$ | 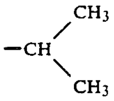 | α-$CH_3$ | F | F | 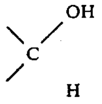 | 1,4 | 222-224° C. (THF/hexane) |
| 7C-2 | $-CH_2Cl$ | $-CH_2CH_2CH_3$ | α-$CH_3$ | F | F | 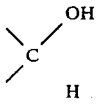 | 1,4 | 180.5-181.5° C. (THF/hexane) |
| 7C-3 | $-CH_2F$ | $-CH_2CH_2CH_3$ | α-$CH_3$ | F | H | 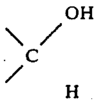 | 1,4 | 165-165.5° C. (THF/hexane) |

-continued

| Compound No. | $R_1$ | $R_2$ | $R_3$ | $R_4$ | $R_5$ | Z | Δ | m.p. |
|---|---|---|---|---|---|---|---|---|
| 7C-4 | $-CH_2CH_2Cl$ | 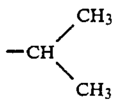 | H | H | H | 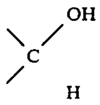 | 1,4 | 188.5-189.5° C. (THF/hexane) |
| 7C-5 | $-CH_3$ | $-CH_2CH_2Cl$ | α-$CH_3$ | F | H | 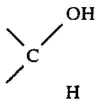 | 1,4 | 223-227° C. (isopropanol) |
| 7C-6 | $-CH_2Cl$ | $-C_2H_5$ | α-$CH_3$ | H | F | 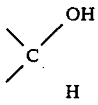 | 1,4 | 153.5-154.5° C. (THF/n-hexane) |
| 7C-7 | $-CH_2Cl$ | $-(CH_2)_2CH_3$ | α-$CH_3$ | H | F | 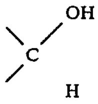 | 1,4 | 98.5-99.5° C. (ethyl acetate/n-hexane) |
| 7C-8 | $-CH_2Cl$ | 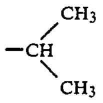 | α-$CH_3$ | H | F | 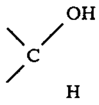 | 1,4 | 124.5-126° C. (ethyl acetate/n-hexane) |
| 7C-9 | $-CH_2Cl$ | $-(CH_2)_2CH_3$ | H | H | H | 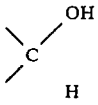 | 1,4 | 180.5-181.5° C. (THF/n-hexane) |
| 7C-10 | $-CH_2Cl$ | $-CH_3$ | H | H | H | 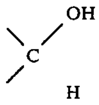 | 1,4 | 235-237° C. (THF/n-hexane) |
| 7C-11 | $-CH_2Cl$ | $-CH_3$ | α-$CH_3$ | H | F | 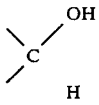 | 1,4 | 244.5-245.5° C. (THF/n-hexane) |
| 7C-12 | $-CH_2Cl$ | $-CH_3$ | β-$CH_3$ | F | H | 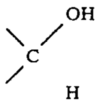 | 1,4 | 236-236.5° C. (THF/n-hexane) |
| 7C-13 | $-CH_2Cl$ | $-CH_2CH_2CH_3$ | β-$CH_3$ | F | H | 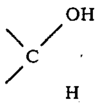 | 1,4 | 183.5-184° C. (THF/n-hexane) |

The foregoing compounds can be named as follows:

7C-1: chloromethyl 6α,9α-difluoro-11β-hydroxy-17α-isopropoxycarbonyloxy-16α-methylandrosta-1,4-dien-3-one-17β-carboxylate 7C-2: chloromethyl 6α,9α-difluoro-11β-hydroxy-16α-methyl-17α-n-propoxycarbonyloxyandrosta-1,4-dien-3-one-17β-carboxylate 7C-3: fluoromethyl 9α-fluoro-11β-hydroxy-16α-methyl-17α-n-propoxycarbonyloxyandrosta-1,4-dien-3-one-17β-carboxylate 7C-4: 2-chloroethyl 11β-hydroxy-17α-isopropoxycarbonyloxyandrosta-1,4-dien-3-one-17β-carboxylate 7C-5: methyl 17α-(2-chloroethoxy)carbonyloxy-9α-fluoro-11β-hydroxy-16α-methylandrosta-1,4-dien-3-one-17β-carboxylate 7C-6: chloromethyl 17α-ethoxycarbonyloxy-6α-fluoro-11β-hydroxy-16α-methylandrosta-1,4-dien-3-one-17β-carboxylate 7C-7: chloromethyl 6α-fluoro-11β-hydroxy-16α-methyl-17α-n-propoxycarbonyloxyandrosta-1,4-dien-3-one-17β-carboxylate 7C-8: chloromethyl 6α-fluoro-11β-hydroxy-17α-isopropoxycarbonyloxy-16α-methylandrosta-1,4-dien-3-one-17β-carboxylate 7C-9: chloromethyl 11β-hydroxy-17α-n-propoxycarbonyloxyandrosta-1,4-dien-3-one-17β-carboxylate 7C-10: chloromethyl 11β-hydroxy-17α-methoxycarbonyloxyandrosta-1,4-dien-3-one-17β-carboxylate 7C-11: chloromethyl 6α-fluoro-11β-hydroxy-17α-methoxycarbonyloxy-16α-methylandrosta-1,4-dien-3-one-17β-carboxylate 7C-12: chloromethyl 9α-fluoro-11β-hydroxy-17α-methoxycarbonyloxy-16β-methylandrosta-1,4-dien-3-one-17β-carboxylate 7C-13: chloromethyl 9α-fluoro-11β-hydroxy-16β-methyl-17α-n-propoxycarbonyloxyandrosta-1,4-dien-3-one-17β-carboxylate

EXAMPLE 8

An equivalent quantity of 11β,17α-dihydroxyandrost-4-en-3-one-17β-carboxylic acid is substituted for the 11β-hydroxy-17α-methoxycarbonyloxyandrost-4-en-3-one-17β-carboxylic acid starting material employed in Example 3, and the procedure of the first paragraph of that example is substantially repeated. There are thus obtained, as the intermediate salt, sodium 11β,17α-dihydroxyandrost-4-en-3-one-17β-carboxylate, and, as the final product, chloromethyl 11β,17α-dihydroxyandrost-4-en-3-one-17β-carboxylate, melting at 184°-186° C. (recrystallization from tetrahydrofuran-ether-hexane).

EXAMPLE 9

An equivalent quantity of 11β,17α-dihydroxyandrost-4-en-3-one-17β-carboxylic acid is substituted for the 17α-ethoxycarbonyloxy-11β-hydroxyandrost-4-en-3-one-17β-carboxylic acid starting material employed in Example 4, and the procedure of the first paragraph of that example is substantially repeated. There are thus obtained, as the intermediate salt, sodium 11β,17α-dihydroxyandrost-4-en-3-one-17β-carboxylate, and, as the final product, methylthiomethyl 11β,17α-dihydroxyandrost-4-en-3-one-17β-carboxylate Substitution of an equivalent quantity of methylthiomethyl 11β,17α-dihydroxyandrost-4-en-3-one-17β-carboxylate for the methylthiomethyl 17α-ethoxycarbonyloxy-11β-hydroxyandrost-4-en-3-one-17β-carboxylate used in the second paragraph of Example 4 and substantial repetition of the procedure there detailed affords methylsulfonylmethyl 11α,17α-dihydroxyandrost-4-en-3-one-17β-carboxylate.

EXAMPLE 10A

The procedure of each paragraph of Example 2 is substantially repeated, substituting an equivalent quantity of each of the following starting materials for the steroids employed therein: chloromethyl 11β,17α-dihydroxyandrost-4-en-3-one-17β-carboxylate; and methylthiomethyl 11β,17α-dihydroxyandrost-4-en-3-one-17β-carboxylate. The following soft anti-inflammatory agents of formula (I) are obtained:

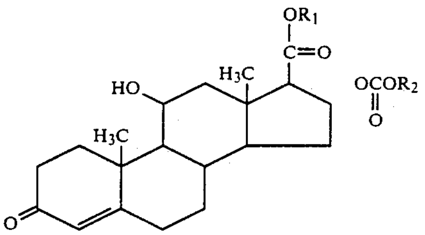

| Compound No. | $R_1$ | $R_2$ | m.p. |
|---|---|---|---|
| 10A-1 | $CH_2Cl$ | $CH_3$ | 171-173° C. |
| 10A-2 | $CH_2Cl$ | $C_2H_5$ | 197-200° C. (THF/hexane) |
| 10A-3 | $CH_2SCH_3$ | $C_2H_5$ | 137.5-138° C. (ether/hexane) |
| 10A-4 | $CH_2Cl$ | $C_4H_9$ | 99.5-102° C. |

-continued

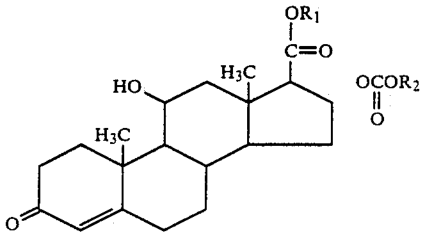

| Compound No. | $R_1$ | $R_2$ | m.p. |
|---|---|---|---|
| | | | (THF/hexane) |
| 10A-5 | $CH_2Cl$ | iso-$C_3H_7$ | 183.5-184.5° C. (THF/hexane) |
| 10A-6* | $CH_2Cl$ | iso-$C_4H_9$ | 140-141° C. (THF/isopropyl ether) |

*utilizing isobutyl chloroformate as the alkyl chloroformate reactant

EXAMPLE 10B

The procedure of each paragraph of Example 2 is substantially repeated, substituting an equivalent quantity of each of the following starting materials for the steroids employed therein: methylthiomethyl 11β,17α-dihydroxyandrost-4-en-3-one-17β-carboxylate; and methylfulfonylmethyl 11β,17α-dihydroxyandrost-4-en-3-one-17β-carboxylate. The following soft anti-inflammatory agents of formula (I) are obtained.

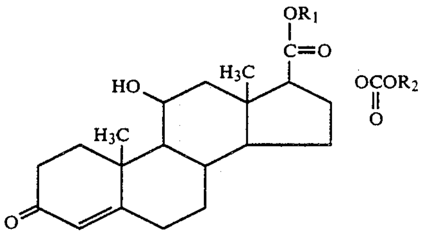

| Compound No. | $R_1$ | $R_2$ |
|---|---|---|
| 10B-1 | $CH_2SCH_3$ | $CH_3$ |
| 10B-2 | $CH_2SCH_3$ | $C_4H_9$ |
| 10B-3 | $CH_2SCH_3$ | i-$C_3H_7$ |
| 10B-4 | $CH_2SO_2CH_3$ | $CH_3$ |
| 10B-5 | $CH_2SO_2CH_3$ | $C_2H_5$ |
| 10B-6 | $CH_2SO_2CH_3$ | $C_4H_9$ |
| 10B-7 | $CH_2SO_2CH_3$ | i-$C_3H_7$ |

Other representative species, e.g. compounds of Examples 7A and 7B, can likewise be prepared according to the procedures of Examples 8 through 10.

EXAMPLE 11

The products of Example 2 and Example 6A-4 are each allowed to react, first with diethylchlorophosphate and then with $CH_3SNa$ in chloroform for approximately 6 hours. The following intermediates are obtained in the first step:

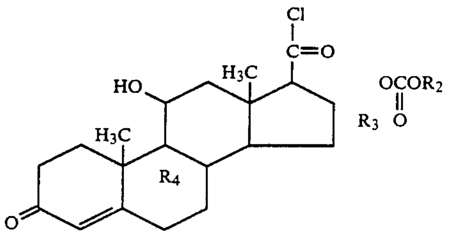

| $R_2$ | $R_3$ | $R_4$ | Δ |
|---|---|---|---|
| $CH_3$ | H | H | 4 |
| $C_2H_5$ | H | H | 4 |
| $C_4H_9$ | H | H | 4 |
| i-$C_3H_7$ | H | H | 4 |
| $C_2H_5$ | α-$CH_3$ | F | 1,4 |

and the following compounds of formula (I) are obtained in the second step:

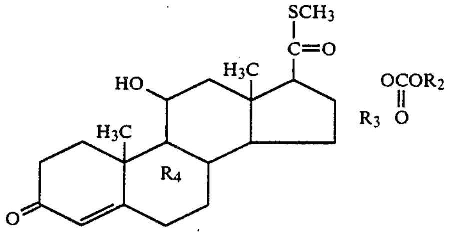

| $R_2$ | $R_3$ | $R_4$ | Δ |
|---|---|---|---|
| $CH_3$ | H | H | 4 |
| $C_2H_5$ | H | H | 4 |
| $C_4H_9$ | H | H | 4 |
| i-$C_3H_7$ | H | H | 4 |
| $C_2H_5$ | α-$CH_3$ | F | 1,4 |

When the remaining products of Example 6A and those of Example 6B are treated according to the above procedure, the corresponding compounds of the formula

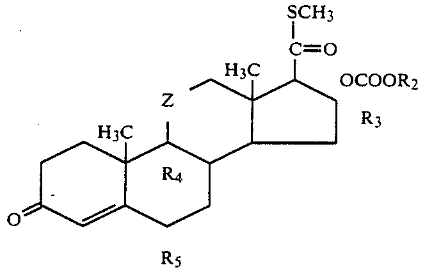

wherein the various structural parameters represented by $R_2$, $R_3$, $R_4$, $R_5$, Z and the dotted line are identical to those of compounds 6A1-6A3, 6A5-6A11, and 6B1-6B25 of Examples 6A and 6B are obtained.

EXAMPLE 12

Chloromethyl 11β,17α-dihydroxyandrost-4-en-3-one-17β-carboxylate (0.01 mol) is dissolved in toluene (100 milliliters) and the solution is cooled to approximately 0° C. Phosgene is then bubbled into the solution, while maintaining the reaction mixture at low temperature, until the reaction is complete (approximately 2 hours). The solvent and excess phosgene are removed by evaporation to leave the crude 17α-chlorocarbonyloxy compound of the formula

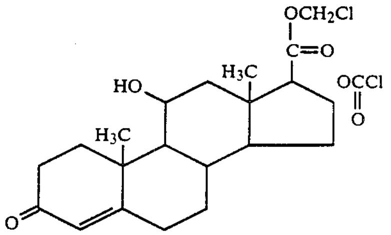

The intermediate (0.01 mol) obtained above is then combined with ethanol (0.02 mol) containing 2,6-dimethylpyridine (0.01 mol) and allowed to react at room temperature for 6 hours. At the end of that time, the desired chloromethyl 17α-ethoxycarbonyloxy-11β-hydroxyandrost-4-en-3-one-17β-carboxylate is isolated from the reaction mixture. The compound melts at 197°-200° C., after crystallization.

Substitution of an equivalent quantity of methylthiomethyl 11β,17α-dihydroxyandrost-4-en-3-one-17β-carboxylate for the chloromethyl 11β,17α-dihydroxyandrost-4-en-3-one-17β-carboxylate used above and substantial repetition of the foregoing procedure affords methylthiomethyl 17α-ethoxycarbonyloxy-11β-hydroxyandrost-4-en-3-one-17β-carboxylate, melting at 133°-136° C., after crystallization. That compound can then, if desired, be converted to the corresponding sulfonyl or sulfinyl compound as described in Example 4.

Other representative species, e.g., the compounds of Example 3, paragraphs 1, 3, 4 and 5, and the compounds of Examples 7A and 7B can be prepared in like manner from reaction of the corresponding 17α-hydroxy 17β-carboxylates with the appropriate alcohols, including, when appropriate, subsequent treatment with m-chloroperoxybenzoic acid as in Example 4.

EXAMPLE 13

The procedure of the first paragraph of Example 12 is repeated, except that an equivalent quantity of 11β,17α-dihydroxyandrost-4-en-3-one-17β-carboxylic acid is used in place of the chloromethyl 11β,17α-dihydroxyandrost-4-en-3-one-17β-carboxylate. The crude intermediate thus obtained has the formula

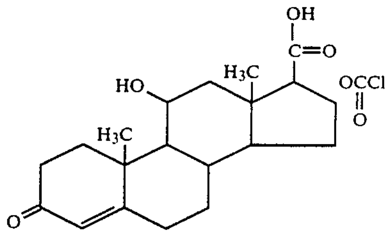

That intermediate is then subjected to the procedure of the second paragraph of Example 12, to afford 17α-ethoxycarbonyloxy-11β-hydroxyandrost-4-en-3-one-17β-carboxylic acid, identical to the product of Example 2, paragraph 2.

The other compounds of Examples 2, 6A and 6B can be prepared using the same general procedure.

EXAMPLE 14

Chloromethyl 11β,17α-dihydroxyandrost-4-en-3-one-17β-carboxylate (0.02 mol) is combined with diethylcarbonate (0.2 mol) containing 20 mg of p-toluenesulfonic acid. The reaction mixture is maintained at room temperature for 4 hours, then heated to about 80° to 85° C.; the remaining ethanol which forms is removed by distillation under reduced pressure. Obtained as the residue is crude chloromethyl 17α-ethoxycarbonyloxy-11β-hydroxyandrost-4-en-3-one-17β-carboxylate, melting at 197°-200° C., after crystallization.

Substitution of an equivalent quantity of methylthiomethyl 11β,17α-dihydroxyandrost-4-en-3-one-17β-carboxylate for the chloromethyl 11β,17α-dihydroxyandrost-4-en-3-one-17β-carboxylate used above and substantial repetition of the foregoing procedure affords methylthiomethyl 17α-ethoxycarbonyloxy-11β-hydroxyandrost-4-en-3-one-17β-carboxylate, melting at 133°-136° C. That compound can then, if desired, be converted to the corresponding sulfonyl or sulfinyl compound as described in Example 4.

Other representative species, e.g., the compounds of Example 3, paragraphs, 1, 3, 4 and 5, and the compounds of Examples 7A and 7B, can be prepared in like manner from reaction of the corresponding 17α-hydroxy-17β-carboxylates with the appropriate carbonates of the type $$R_2O\underset{\underset{O}{\|}}{C}OR_2$$

(including, when appropriate, subsequent treatment with m-chloroperoxybenzoic acid as in Example 4).

EXAMPLE 15

To a solution of 8.7 grams of 11β,17α-dihydroxyandrost-4-en-3-one-17β-carboxylic acid and 9.6 milliliters of triethylamine in 100 milliliters of dry dichloromethane, is added 10 grams of ethyl chloroformate, dropwise at 0° to 5° C. The reaction mixture is gradually allowed to warm to room temperature and the insoluble material is removed by filtration. The filtrate is washed successively with 3% aqueous sodium bicarbonate, 1% hydrochloric acid, and water, then is dried over anhydrous magnesium sulfate. The solvent is concentrated under reduced pressure and the residue is crystallized to give 10.5 grams of ethoxycarbonyl 17α-ethoxycarbonyloxy-11β-hydroxyandrost-4-en-3-one-17β-carboxylate, melting at 158°-159° C.

EXAMPLE 16

Following the general method described in Example 15 and substituting therein the appropriate reactants affords the following additional compounds:

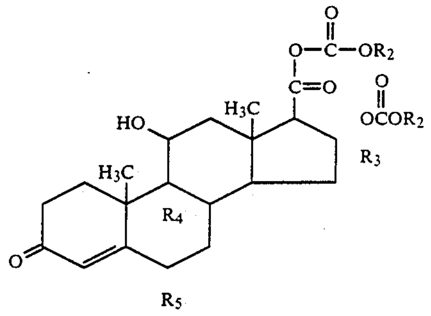

| Compound No. | $R_2$ | $R_3$ | $R_4$ | $R_5$ | Δ | melting point |
|---|---|---|---|---|---|---|
| 16-A | $-CH_2CH_3$ | H | F | H | 4 | 110-111° C. (THF-isopropyl ether) |
| 16-B | iso-$C_3H_7$ | H | H | H | 4 | 200-203° C. |
| 16-C | $-CH_2CH_2CH_3$ | H | H | H | 4 | 142-143° C. (THF) |

EXAMPLE 17

To a solution of 9.8 grams of ethoxycarbonyl 17α-ethoxycarbonyloxy-11β-hydroxyandrost-4-en-3-one-17β-carboxylate in 100 milliliters of tetrahydrofuran and 120 milliliters of ethanol are added 42 millilitere of 5% aqueous sodium becarbonate. The mixture is stirred at room temperature for about 30 hours and adjusted to pH 2 to 3 by adding 1N hydrochloric acid. The insoluble material is isolated by filtration. Recrystallization from a mixture of tetrahydrofuran and n-hexane gives 6 grams of 17α-ethoxycarbonyloxy-11β-hydroxyandrost-4-en-3-one-17β-carboxylic acid having a melting point of 192°-195° C.

The compound obtained in Example 2, first paragraph, and the compounds of Example 6A can be prepared, following the same procedure as above and substituting therein appropriate reactants.

EXAMPLE 18

Following the general method described in Example 17 and substituting therein the appropriate reactants affords the following compounds:

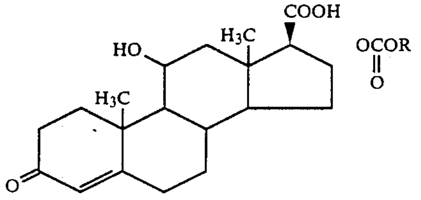

| Compound No. | R | melting point |
|---|---|---|
| 18-A | $-CH{<}^{CH_3}_{CH_3}$ | 144.5-146.5° C. (THF/hexane) |
| 18-B | $-(CH_2)_3CH_3$ | 164-166° C. (THF/hexane) |

EXAMPLE 19

To a solution of 8.7 grams of 11β,17α-dihydroxyandrost-4-en-3-one-17β-carboxylic acid and 10 grams of triethylamine in 100 milliliters of dichloromethane, a solution of 13.2 grams of n-propyl chloroformate in 20 milliliters of dichloromethane is added dropwise over 1-1.5 hours with ice-cooling. The reaction mixture is allowed to warm to room temperature over a 2 hour period, then is washed successively with 3% aqueous sodium bicarbonate, 1N hydrochloric acid, and water and dried over anhydrous sodium sulfate. The solvent is concentrated under reduced pressure. Crystallization from a mixture of ether and n-hexane gives 10.5 grams of propoxycarbonyl 11β-hydroxy-17α-propoxycarbonyloxyandrost-4-en-3-one-17β-carboxylate, which is dissolved in 40 milliliters of pyridine. To that solution, 300 milliliters of water are added dropwise over a 1 to 1.5 hour period. The mixture is stirred for one hour and adjusted to pH 2 to 2.5 by adding concentrated hydrochloric acid with ice-cooling. The mixture is then extracted with chloroform, washed successively with 1N hydrochloric acid and water, and then dried over sodium sulfate. The solvent is concentrated under reduced pressure, and the residue is recrystallized from a mixture of acetone and tetrahydrofuran to give 7.7 grams of 11β-hydroxy-17α-propoxycarbonyloxyandrost-4-en-3-one-17β-carboxylic acid, melting at 156°-157° C.

EXAMPLE 20

Following the general procedure detailed in Example 19, but utilizing the appropriate starting materials and reaction conditions, affords the remaining compounds of Example 6A.

EXAMPLE 21

Chloromethyl 17α-ethoxycarbonyloxy-9α-fluoro-11β-hydroxy-16α-methylandrosta-1,4-dien-3-one-17β-carboxylate (2 grams) is dissolved in anhydrous dichloromethane (200 milliliters) and pyridinium chlorochromate (3.5 grams) is added at room temperature, with stirring. The resultant mixture is stirred for 24 hours, then the solvent is concentrated under reduced pressure at about 10° to 20° C. The residue is subjected to column chromatography on silica gel (Kiesel gel 60), using chloroform as an eluting solvent, followed by recrystallization from a mixture of tetrahydrofuran and isopropyl ether to give chloromethyl 17α-ethoxycarbonyloxy-9α-fluoro-16α-methylandrosta-1,4-dien-3,11-dione-17β-carboxylate, in the yield of 1.7 grams, melting at 138°-140° C.

EXAMPLE 22

By a method similar to that described in Example 21, there is obtained chloromethyl 9α-fluoro-17α-isopropoxycarbonyloxy-16β-methylandrosta-1,4-dien-3,11-dione-17β-carboxylate, melting at 200°-201° C.

EXAMPLE 23

Utilizing the general procedure of Example 3, but substituting the appropriate reactants therein, affords methyl 17α-(2-chloroethoxy)carbonyloxy-9α-fluoro-11β-hydroxy-16α-methylandrosta-1,4-dien-3-one-17β-carboxylate. That product, after recrystallization from isopropanol, melts at 223°-227° C.

EXAMPLE 24

In the same general manner as in Example 3, there is obtained 2-chloroethyl 17α-ethoxycarbonyloxy-9α-fluoro-11β-hydroxy-16α-methylandrosta-1,4-dien-3-one-17β-carboxylate. That product, after recrystallization from tetrahydrofuran-hexane, melts at 243°-245° C.

EXAMPLE 25

Chloromethyl 17α-ethoxycarbonyloxy-11β-hydroxyandrost-4-en-3-one-17β-carboxylate (0.01 mol) and 1,2-dikmethylpyrrolidine (0.01 mol) are dissolved in acetonitrile (80 milliliters), and heated to the reflux temperature. The reaction mixture is maintained at that temperature, with stirring, for approximately 4 hours. About 65 ml of acetonitrile are removed; then, the mixture is cooled to room temperature and excess ethyl ether is added to cause precipitation. The precipitate is separated by filtration, washed, and dried in vacuo, thus affording the desired quaternary ammonium salt of the formula

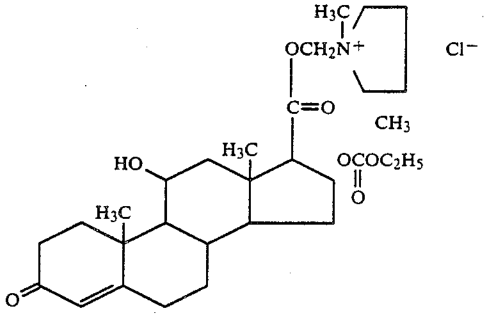

In analogous fashion, use of the appropriate steroidal and amine starting materials in the foregoing general procedure affords the following additional quaternary ammonium salts of the invention

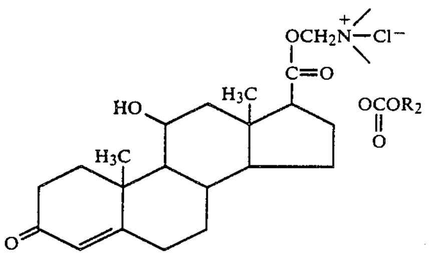

| $R_2$ | 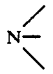 |
|---|---|
| $CH_3$ | 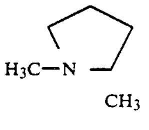 |
| i-$C_3H_7$ | $N(C_2H_5)_3$ |
| $C_4H_9$ | 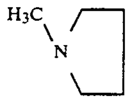 |
| $C_2H_5$ | 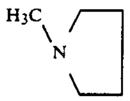 |

-continued

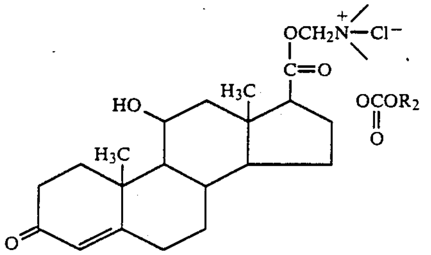

| R2 | 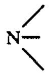 |
|---|---|
| $C_2H_5$ | 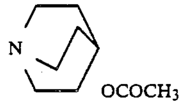 |
| $C_2H_5$ | $N(C_2H_5)_3$ |
| $C_2H_5$ | 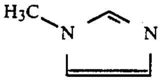 |

EXAMPLE 26

| | | |
|---|---|---|
| Ointment | | |
| Compound of formula (I), e.g. chloromethyl 17α-ethoxycarbonyloxy-11β-hydroxyandrost-4-en-3-one-17β-carboxylate or chloromethyl 11β-hydroxy-17α-isopropoxycarbonyloxyandrost-4-en-3-one-17β-carboxylate | 0.2% | w/w |
| Liquid paraffin | 10.0% | w/w |
| White soft paraffin | 89.8% | w/w |
| Aphthous Ulcer Pellet | | |
| Compound of formula (I), as above | 0.25 | mg |
| Lactose | 69.90 | mg |
| Acacia | 3.00 | mg |
| Magnesium stearate | 0.75 | mg |
| Retention Enema | | |
| Compound of formula (I), as above | 0.001% | w/v |
| Tween 80 | 0.05% | w/v |
| Ethanol | 0.015% | w/v |
| Propylparaben | 0.02% | w/v |
| Methylparaben | 0.08% | w/v |
| Distilled water | q.s. 100 volumes | |
| Eye Drops | | |
| Compound of formula (I), as above | 0.1% | w/v |
| Tween 80 | 2.5% | w/v |
| Ethanol | 0.75% | w/v |
| Benalkonium chloride | 0.02% | w/v |
| Phenyl ethanol | 0.25% | w/v |
| Sodium chloride | 0.60% | w/v |
| Water for injection | q.s. 100 volumes | |

EXAMPLE 27

| | | |
|---|---|---|
| Ointment | | |
| Compound of formula (I), e.q. chloromethyl 17α-ethoxycarbonyloxy-9α-fluoro-11β-hydroxy-16α-methylandrosta-1,4-dien-3-one-17β-carboxylate or chloromethyl 9α-fluoro-11β-hydroxy-17α-methoxycarbonyloxy-16α-methylandrosta-1,4-dien-3-one-17β-carboxylate | 0.025% | w/w |
| Liquid paraffin | 10.175% | w/w |
| White soft paraffin | 89.8% | w/w |
| Aphthous Ulcer Pellet | | |
| Compound of formula (I), e.g. chloromethyl 9α-fluoro-11α-hydroxy-17α-isopropoxycarbonyloxy-16β-methylandrosta-1,4-dien-3-one-17β-carboxylate or chloromethyl 17α-ethoxycarbonyloxy-9α-fluoro-11β-hydroxy-16α-methylandrosta-1,4-dien-3-one-17β-carboxylate | 0.1 | mg |
| Lactose | 69.90 | mg |
| Acacia | 3.00 | mg |
| Magnesium stearate | 0.75 | mg |
| Retention Enema | | |
| Compound of formula (I), e.g. chloromethyl 11β-hydroxy-17α-isopropoxycarbonyloxy-androsta-1,4-dien-3-one-17β-carboxylate or chloromethyl 9α-fluoro-11β-hydroxy-17α-isopropoxycarbonyloxy-16β-methylandrosta-1,4-dien-3-one-17β-carboxylate | 0.001% | w/v |
| Tween 80 | 0.05% | w/v |
| Ethanol | 0.015% | w/v |
| Propylparaben | 0.02% | w/v |
| Methylparaben | 0.08% | w/v |
| Distilled water | q.s. 100 volumes | |
| Eye Drops | | |
| Compound of formula (I), e.g. chloromethyl 9α-fluoro-11β-hydroxy-16α-methyl-17α-propoxy-carbonyloxyandrosta-1,4-dien-3-one-17β-carboxylate or chloromethyl 9α-fluoro-11β-hydroxy-17α-methoxy-carbonyloxy-16α-methyl-androsta-1,4-dien-3-one-17β-carboxylate | 0.025% | w/v |
| Tween 80 | 2.5% | w/v |
| Ethanol | 0.75% | w/v |
| Benzalkonium chloride | 0.02% | w/v |
| Phenyl ethanol | 0.25% | w/v |
| Sodium chloride | 0.60% | w/v |
| Water for injection | q.s. 100 volumes | |

EXAMPLE 28

To a solution of 3 grams of chloromethyl 11β-hydroxy-17α-isopropoxycarbonyloxyandrost-4-en-3-one-17β-carboxylate in 100 ml of acetonitrile, 7.9 grams of AgF (a 10:1 molar ratio of AgF to steriod) are added, and the mixture is stirred at room temperature for 12 days while shading the reaction system for light. Thereafter, the reaction mixture is filtered, and the solid on the filter is fully washed with ethyl acetate. The filtrate and the ethyl acetate solution are combined, and the mixture is washed with water and a saturated aqueous sodium chloride solution, and dried over anhydrous sodium sulfate. The solvents are distilled off, giving 2 grams of crude crystalline product. The product is subjected to preparative thin-layer chromatography (Silica Gel 60F254, Merck), using a mixture of chloroform and methanol (15:1) as an eluting solvent. Then the product is recrystallized from a mixture of tetrahydrofuran and n-hexane to give 180 mg of fluoromethyl 11β-hydroxy-17α-isopropoxycarbonyloxyandrost-4-en-3-one-17β-carboxylate as colorless needles, melting at 207.5°-210° C.

EXAMPLE 29

Following the general procedure of Example 28 and substituting therein the appropriate reactants affords the following compounds:

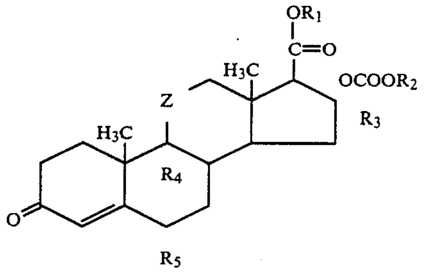

| Compound No. | $R_1$ | $R_2$ | $R_3$ | $R_4$ | $R_5$ | Z | Δ | mp |
|---|---|---|---|---|---|---|---|---|
| 29-1 | $-CH_2F$ | $-C_2H_5$ | α-$CH_3$ | F | H | 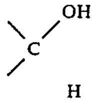 | 1,4 | 239-240.5° C. (THF/hexane) |
| 29-2 | $-CH_2F$ | $-CH_2CH_2CH_3$ | α-$CH_3$ | F | H | 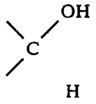 | 1,4 | 165-165.5° C. (THF/hexane) |

The foregoing compounds can be named as follows:

29-1: fluoromethyl 17α-ethoxycarbonyloxy-9α-fluoro-11β-hydroxy-16α-methylandrosta-1,4-dien-3-one-17β-carboxylate 29-2: fluoromethyl 9α-fluoro-11β-hydroxy-16α-methyl-17α-n-propoxycarbonyloxyandrosta-1,4-dien-3-one-17β-carboxylate From the foregoing description, one of ordinary skill in the art can readily ascertain the essential characteristics of the present invention and, without departing from the spirit and scope thereof, can make various changes in and/or modifications of the invention to adapt it to various usages and conditions. As such, these changes and/or modifications are properly, equitably and intended to be within the full range of equivalence of the following claims.

What is claimed is:

1. A compound selected from the group consisting of:

(a) a compound of the formula

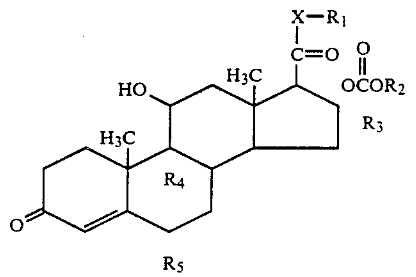

(I)

wherein:

$R_1$ is $C_1$-$C_{10}$ alkyl; $C_2$-$C_{10}$ (monohydroxy or polyhydroxy)alkyl; $C_1$-$C_{10}$ (monohalo or polyhalo)alkyl; or $-CH_2COOR_6$ wherein $R_6$ is unsubstituted or substituted $C_1$-$C_{10}$ alkyl; $C_3$-$C_8$ cycloalkyl, $C_3$-$C_8$ cycloalkenyl or $C_2$-$C_{10}$ alkenyl, the substituents being selected from the group consisting of halo, lower alkoxy, lower alkylthio, lower alkylsulfinyl, lower alkylsulfonyl, $$-NH\overset{O}{\overset{\|}{C}}-(C_1\text{-}C_{10}\text{ alkyl}) \text{ and } -O\overset{O}{\overset{\|}{C}}-(C_1\text{-}C_{10}\text{ alkyl}),$$

or $R_6$ is unsubstituted or substituted phenyl or benzyl, the substituents being selected from the group consisting of lower alkyl, lower alkoxy, halo, carabamoyl, lower alkoxycarbonyl, lower alkanoyloxy, lower haloalkyl, mono(lower alkyl)amino, di(lower alkyl)amino, mono(lower alkyl)carbamoyl, di(lower alkyl)carbamoyl, lower alkylthio, lower alkylsulfinyl and lower alkylsulfonyl; or $R_1$ is $-CH_2CONR_7R_8$ wherein $R_7$ and $R_8$, which can be the same or different, are each hydrogen, lower alkyl, $C_3$-$C_8$ cycloalkyl, phenyl or benzyl, or $R_7$ and $R_8$ are combined such that $-NR_7R_8$ represents the residue of a saturated monocyclic secondary amine; or $R_1$ is unsubstituted or substituted phenyl or benzyl, the substituents being selected from the group of phenyl and benzyl substituents defined hereinabove with respect to $R_6$; or $R_1$ is $$-\underset{R_9}{\underset{|}{C}H}-Y\text{-(lower alkyl)}$$

wherein Y is —S—, —SO—, $-SO_2-$ or —O— and $R_9$ is hydrogen, lower alkyl or phenyl, or $R_9$ and the lower alkyl group adjacent to Y are combined so that $R_1$ is a cyclic system of the type

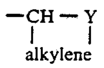

wherein Y is defined as above and the alkylene group contains 3 to 10 carbon atoms, of which at least 3 and no more than 6 are ring atoms; or $R_1$ is

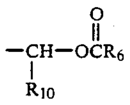

wherein $R_6$ is defined as hereinabove and $R_{10}$ is hydrogen, lower alkyl, phenyl or halophenyl;

$R_2$ is unsubstituted or substituted $C_1$-$C_{10}$ alkyl, $C_3$-$C_8$ cycloalkyl, $C_3$-$C_8$ cycloalkenyl or $C_2$-$C_{10}$ alkenyl, the substituents being selected from the group consisting of halo, lower alkoxy, lower alkylthio, lower alkylsulfinyl, lower alkylsulfonyl,

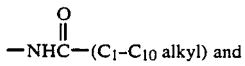 and 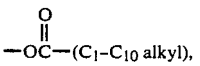, or $R_2$ is unsubstituted or substituted phenyl or benzyl, the substituents being selected from the group consisting of lower alkyl, lower alkoxy, halo, carbamoyl, lower alkoxycarbonyl, lower alkanoyloxy, lower haloalkyl, mono(lower alkyl)amino, di(-lower alkyl)amino, mono(lower alkyl)carbamoyl, di(lower alkyl)carbamoyl, lower alkylthio, lower alkylsulfinyl and lower alkylsulfonyl;

$R_3$ is hydrogen, α-hydroxy, β-hydroxy, α-methyl, β-methyl, $=CH_2$, or α- or

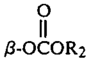

wherein $R_2$ is identical to $R_2$ as defined hereinabove;

$R_4$ is hydrogen, fluoro or chloro;

$R_5$ is hydrogen, fluoro, chloro or methyl;

X is —O— or —S—;

and the dotted line in ring A indicates that the 1,2 linkage is saturated or unsaturated;

(b) a quaternary ammonium salt of a compound of formula (I) wherein at least one of $R_1$ and $R_2$ is a halo-substituted alkyl group;

(c) a compound of the formula (III)

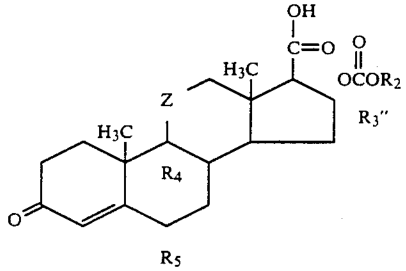

wherein $R_2$, $R_4$, $R_5$, and the dotted line in ring A are as defined in (a) above, Z is carbonyl or β-hydroxymethylene and $R_3''$ is hydrogen, α-methyl, β-methyl, $=CH_2$ or α- or

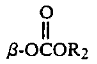

wherein $R_2$ is identical to $R_2$ above;

(d) a compound of the formula (IV)

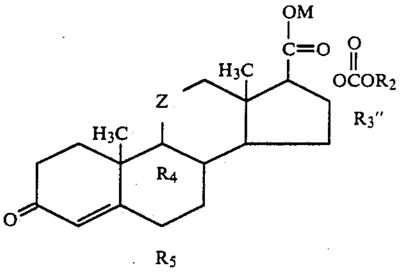

wherein M is alkali metal, thallium, alkaline earth metal/2 or $NH_4$ and $R_2$, $R_3''$, $R_4$, $R_5$, Z and the dotted line in ring A are as defined in (a) and (c) above;

(e) a compound of the formula (VII)

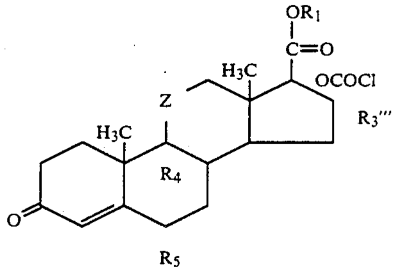

wherein $R_3'''$ is hydrogen, α-methyl, β-methyl, α-OCOCl or β-OCOCl, and $R_1$, $R_4$, $R_5$, Z and the dotted line in ring A are as defined in (a) and (c) above;

(f) a compound of the formula (VIII)

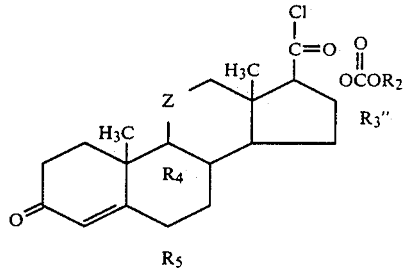

wherein $R_2$, $R_3''$, $R_4$, $R_5$, Z and the dotted line in ring A are as defined in (a) and (c) above; and (g) a compound of the formula (IX)

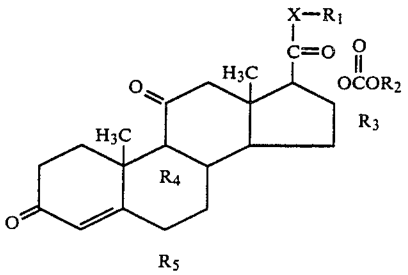

wherein $R_1$, $R_2$, $R_3$, $R_4$, $R_5$, X and the dotted line in ring A are as defined in (a) above.

2. A compound selected from the group consisting of:

(a) a compound of the formula (I)

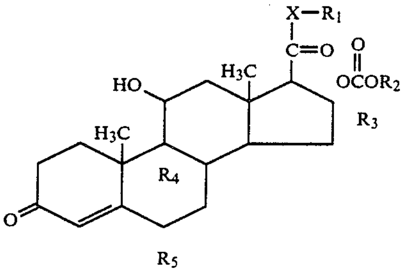

wherein:

$R_1$ is $C_1$-$C_6$ alkyl; $C_1$-$C_6$ (monohalo or polyhalo)alkyl; —$CH_2COOR_6$ wherein $R_6$ is $C_1$-$C_6$ alkyl; —$CH_2$—Y—($C_1$-$C_6$ alkyl) wherein Y is —S—, —SO—, —$SO_2$— or —O—; or

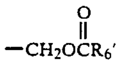

wherein $R_6'$ is $C_1$-$C_6$ or phenyl;

$R_2$ is $C_1$-$C_6$ alkyl, $C_3$-$C_8$ cycloalkyl, phenyl, benzyl or $C_1$-$C_6$ (monohalo or polyhalo)alkyl;

$R_3$ is hydrogen, α-hydroxy, β-methyl, β-methyl or

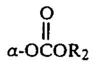

wherein $R_2$ is identical to $R_2$ as defined hereinabove;

$R_4$ is hydrogen or fluoro;

$R_5$ is hydrogen or fluoro;

X is —O—;

and the dotted line in ring A indicates that the 1,2-linkage is saturated or unsaturated;

(b) a quaternary ammonium salt of a compound of formula (I) wherein at least one of $R_1$ and $R_2$ is a halo-substituted alkyl group;

(c) a compound of the formula (III)

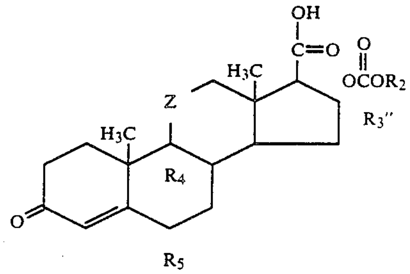

wherein $R_2$, $R_4$, $R_5$ and the dotted line in ring A are as defined in (a) above, Z is carbonyl or β-hydroxymethylene and $R_3''$ is hydrogen, α-methyl, β-methyl or

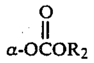

wherein $R_2$ is identical to $R_2$ above;

(d) a compound of the formula (IV)

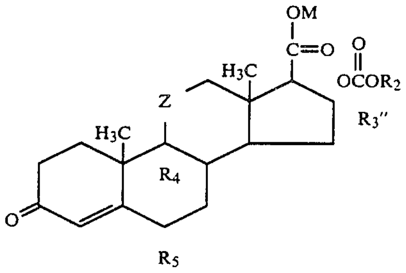

wherein M is alkali metal, thallium, alkaline earth metal/2 or $NH_4$ and $R_2$, $R_3''$, $R_4$, $R_5$, Z and the dotted line in ring A are as defined in (a) and (c) above;

(e) a compound of the formula (VII)

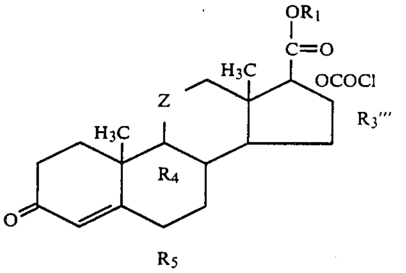

wherein $R_3'''$ is hydrogen, α-methyl, β-methyl or α-OCOCl, and $R_1$, $R_4$, $R_5$, Z and the dotted line in ring A are as defined in (a) and (c) above;

(f) a compound of the formula (VIII)

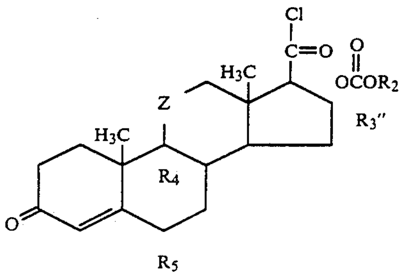

wherein $R_2$, $R_3''$, $R_4$, $R_5$, Z and the dotted line in ring A are as defined in (a) and (c) above; and (g) a compound of the formula (IX)

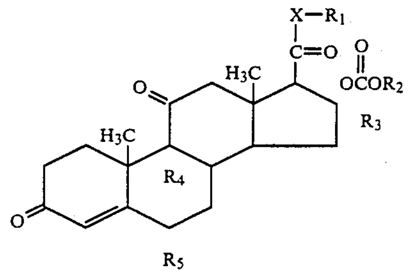

wherein $R_1$, $R_2$, $R_3$, $R_4$, $R_5$, X and the dotted line in ring A are as defined in (a) above.

3. A compound of claim 1 or 2, said compound having the structural formula (I).

4. A compound of claim 1 or 2, said compound being a quaternary ammonium salt of a compound of formula (I) wherein at least one of $R_1$ and $R_2$ is a halo-substituted alkyl group.

5. A compound of claim 1 or 2, said compound having the structural formula (III).

6. A compound of claim 1 or 2, said compound having the structural formula (IV).

7. A compound of claim 1 or 2, said compound having the structural formula (VII).

8. A compound of claim 1 or 2, said compound having the structural formula (VIII).

9. A compound of claim 1 or 2, said compound having the structural formula (IX).

10. A compound of claim 1, said compound having the structural formula (I) wherein $R_3$ is hydrogen, $\alpha$-methyl, $\beta$-methyl, $=CH_2$ or $\alpha$- or $$\beta\text{-O}\overset{\overset{\text{O}}{\|}}{\text{C}}\text{OR}_2.$$

11. A compound of claim 1 or 2, said compound having the structural formula (I) wherein $R_1$ is $C_1$–$C_6$ alkyl.

12. A compound of claim 1 or 2, said compound having the structural formula (I) wherein $R_1$ is $C_1$–$C_6$ (monohalo or polyhalo)alkyl.

13. A compound of claim 12 wherein $C_1$–$C_6$ (monohalo or polyhalo)alkyl is $C_1$–$C_6$ monohaloalkyl.

14. A compound of claim 13 wherein $C_1$–$C_6$ monohaloalkyl is $C_1$–$C_6$ monochloroalkyl.

15. A compound of claim 14 wherein $C_1$–$C_6$ monochloroalkyl is chloromethyl.

16. A compound of claim 11 wherein $R_2$ is $C_1$–$C_6$ alkyl or $C_1$–$C_6$ monohaloalkyl.

17. A compound of claim 12 wherein $R_2$ is $C_1$–$C_6$ alkyl.

18. A compound of claim 13 wherein $R_2$ is $C_1$–$C_6$ alkyl.

19. A compound of claim 14 wherein $R_2$ is $C_1$–$C_6$ alkyl.

20. A compound of claim 15 wherein $R_2$ is $C_1$–$C_6$ alkyl.

21. A compound of claim 11 wherein $R_2$ is $C_3$–$C_8$ cycloalkyl, phenyl, benzyl or $C_1$–$C_6$ (monohalo or polyhalo)alkyl.

22. A compound of claim 12 wherein $R_2$ is $C_3$–$C_8$ cycloalkyl, phenyl, benzyl or $C_1$–$C_6$ (monohalo or polyhalo)alkyl.

23. A compound of claim 13 wherein $R_2$ is $C_3$–$C_8$ cycloalkyl, phenyl, benzyl or $C_1$–$C_6$ (monohalo or polyhalo)alkyl.

24. A compound of claim 14 wherein $R_2$ is $C_3$–$C_8$ cycloalkyl, phenyl, benzyl or $C_1$–$C_6$ (monohalo or polyhalo)alkyl.

25. A compound of claim 15 wherein $R_2$ is $C_3$–$C_8$ cycloalkyl, phenyl, benzyl or $C_1$–$C_6$ (monohalo or polyhalo)alkyl.

26. A compound of claim 1, said compound having the structural formula (I) wherein X is —O—.

27. A compound of claim 12 wherein X is —O—.

28. A compound of claim 13 wherein X is —O—.

29. A compound of claim 14 wherein X is —O—.

30. A compound of claim 17 wherein $R_4$ and $R_5$ are hydrogen.

31. A compound of claim 18 wherein $R_4$ and $R_5$ are hydrogen.

32. A compound of claim 19 wherein $R_4$ and $R_5$ are hydrogen.

33. A compound of claim 20 wherein $R_4$ and $R_5$ are hydrogen.

34. A compound of claim 17 wherein at least one of $R_4$ and $R_5$ is fluoro.

35. A compound of claim 18 wherein at least one of $R_4$ and $R_5$ is fluoro.

36. A compound of claim 19 wherein at least one of $R_4$ and $R_5$ is fluoro.

37. A compound of claim 20 wherein at least one of $R_4$ and $R_5$ is fluoro.

38. A compound of claim 17 wherein $R_4$ is fluoro and $R_5$ is hydrogen.

39. A compound of claim 18 wherein $R_4$ is fluoro and $R_5$ is hydrogen.

40. A compound of claim 19 wherein $R_4$ is fluoro and $R_5$ is hydrogen.

41. A compound of claim 20 wherein $R_4$ is fluoro and $R_5$ is hydrogen.

42. A compound of claim 35 wherein $R_3$ is $\alpha$-methyl or $\beta$-methyl.

43. A compound of claim 37 wherein $R_3$ is $\alpha$-methyl or $\beta$-methyl.

44. A compound of claim 39 wherein $R_3$ is $\alpha$-methyl or $\beta$-methyl.

45. A compound of claim 41 wherein $R_3$ is $\alpha$-methyl or $\beta$-methyl.

46. A compound of claim 1 or 2, said compound having the structural formula (I) wherein $R_1$ is $—CH_2COOR_6$, $—CH_2—Y—(C_1–C_6$ alkyl) or $$-CH_2-O\overset{O}{\overset{\|}{C}}R_6'.$$

47. A compound of claim 1, said compound having the structural formula (I) wherein $R_1$ is $-CH_2CONR_7R_8$.

48. A compound of claim 47 wherein at least one of $R_7$ and $R_8$ is hydrogen or $C_1$–$C_6$ alkyl.

49. A compound of claim 47 wherein $R_7$ and $R_8$ are combined so that $-NR_7R_8$ represents the residue of a saturated monocyclic secondary amine containing 5 to 7 carbon atoms.

50. A compound of claim 49 wherein $-NR_7R_8$ representss morpholino, 1-pyrrolidinyl, 4-benzyl-1-piperazinyl, perhydro-1,2,4-oxathiazin-4-yl, 1- or 4-piperazinyl, 4-methyl-1-piperazinyl, piperidino, hexamethyleneimino, 4-phenylpiperidino, 2-methyl-1-pyrazolidinyl, 1- or 2-pyrazolidinyl, 3-methyl-1-imidazolidinyl, 1- or 3-imidazolidinyl, 4-benzylpiperidino or 4-phenyl-1-piperazinyl.

51. A compound of claim 1, said compound having the structural formula (I) wherein $R_1$ is $$-\underset{R_9}{\underset{|}{C}}H-Y\text{-(lower alkyl)}$$

wherein $R_9$ is hydrogen or methyl, or wherein $R_9$ and the lower alkyl group adjacent to Y are combined so that $R_1$ is $$-\underset{\text{alkylene}}{\underbrace{CH-Y}}$$

wherein Y is —S—, —SO—, $-SO_2-$ or —O— and the alkylene group contains 3 to 10 carbon atoms, of which at least 3 and no more than 6 are ring atoms.

52. A compound of claim 1 or 2, said compound having the structural formula (III) wherein Z is β-hydroxymethylene and $R_2$ is $C_1$–$C_6$ alkyl.

53. A compound of claim 1 or 2, said compound having the structural formula (IV) wherein Z is β-hydroxymethylene and $R_2$ is $C_1$–$C_6$ alkyl.

54. A compound of claim 1 or 2, said compound having the structural formula (VII) wherein Z is β-hydroxymethylene and $R_1$ is $C_1$–$C_6$ alkyl or $C_1$–$C_6$ monohaloalkyl.

55. A compound of claim 1 or 2, said compound having the structural formula (VIII) wherein Z is β-hydroxymethylene and $R_2$ is $C_1$–$C_6$ alkyl.

56. A compound of claim 1 or 2, said compound having the structural formula (IX) wherein $R_1$ is $C_1$–$C_6$ (monohalo or polyhalo) alkyl.

57. A compound of claim 56 wherein $C_1$–$C_6$ (monohalo or polyhalo)alkyl is $C_1$–$C_6$ monohaloalkyl.

58. A compound of claim 57 wherein $R_2$ is $C_1$–$C_6$ alkyl.

59. A compound of claim 1 or 2, said compound having the structural formula (IX) wherein $R_1$ is $C_1$–$C_6$ alkyl or $C_1$–$C_6$ monohaloalkyl, $R_2$ is $C_1$–$C_6$alkyl or $C_1$–$C_6$ monohaloalkyl and X is —O—.

60. A compound of claim 2, said compound having the structural formula (IX) wherein $R_1$ is $C_1$–$C_6$ alkyl, $-CH_2COOR_6$, $-CH_2-Y-(C_1$–$C_6$ alkyl) or $$-CH_2-O\overset{O}{\overset{\|}{C}}R_6'.$$

61. The compound of claim 2 which is chloromethyl 11β-hydroxy-17α-methoxycarbonyloxyandrost-4-en-3-one-17β-carboxylate.

62. The compound of claim 2 which is chloromethyl 17α-ethoxycarbonyloxy-11β-hydroxyandrost-4-en-3-one-17β-carboxylate.

63. The compound of claim 2 which is chloromethyl 17β-butoxycarbonyloxy-11β-hydroxyandrost-4-en-3-one-17β-carboxylate.

64. The compound of claim 2 which is chloromethyl 11β-hydroxy-17α-isopropoxycarbonyloxyandrost-4-en-3-one-17β-carboxylate.

65. The compound of claim 2 which is chloromethyl 17α-ethoxycarbonyloxy-9α-fluoro-11β-hydroxy-16β-methylandrosta-1,4-dien-3-one-17β-carboxylate.

66. The compound of claim 2 which is chloromethyl 9α-fluoro-11β-hydroxy-16α-methyl-17α-propoxycarbonyloxyandrosta-1,4-dien-3-one-17β-carboxylate.

67. The compound of claim 2 which is 1-chloroethyl 11β-hydroxy-17α-isopropoxycarbonyloxyandrost-4-en-3-one-17β-carboxylate.

68. The compound of claim 2 which is 1-chloroethyl 9α-fluoro-11β-hydroxy-17α-isopropoxycarbonyloxy-16β-methylandrosta-1,4-dien-3-one-17β-carboxylate.

69. The compound of claim 2 which is chloromethyl 17α-ethoxycarbonyloxy-11β-hydroxyandrosta-1,4-dien-3-one-17β-carboxylate.

70. The compound of claim 2 which is chloromethyl 11β-hydroxy-17α-isopropoxycarbonyloxyandrosta-1,4-dien-3-one-17β-carboxylate.

71. The compound of claim 2 which is chloromethyl 17α-ethoxycarbonyloxy-9α-fluoro-11β-hydroxyandrosta-1,4-dien-3-one-17β-carboxylate.

72. The compound of claim 2 which is chloromethyl 17α-ethoxycarbonyloxy-9α-fluoro-11β-hydroxy-16α-methylandrosta-1,4-dien-3-one-17β-carboxylate.

73. The compound of claim 2 is chloromethyl 9α-fluoro-11β-hydroxy-17α-isopropoxycarbonyloxy-16α-methylandrosta-1,4-dien-3-one-17β-carboxylate.

74. The compound of claim 2 which is chloromethyl 9α-fluoro-11β-hydroxy-17α-isopropoxycarbonyloxy-16β-methylandrosta-1,4-dien-3-one-17β-carboxylate.

75. The compound of claim 2 which is chloromethyl 9α-fluoro-11β-hydroxy-17α-methoxycarbonyloxy-16β-methylandrosta-1,4-dien-3-one-17β-carboxylate.

76. The compound of claim 2 which is chloromethyl 9α-fluoro-11β-hydroxy-16α-methyl-17α-pentyloxycarbonyloxyandrosta-1,4-dien-3-one-17β-carboxylate.

77. The compound of claim 2 which is fluoromethyl 17α-ethoxycarbonyloxy-9α-fluoro-11β-hydroxy-16α-methylandrosta-1,4-dien-3-one-17β-carboxylate.

78. The compound of claim 2 which is methyl 17α-(2-chloroethoxy)carbonyloxy-9α-fluoro-11β-hydroxy-16α-methylandrosta-1,4-dien-3-one-17β-carboxylate.

79. The compound of claim 2 which is 17β-ethoxycarbonyloxy-9α-fluoro-11β-hydroxy-16α-methylandrosta-1,4-dien-3-one-17β-carboxylic acid.

80. The compound of claim 2 which is 9α-fluoro-11β-hydroxy-17α-isopropoxycarbonyloxy-16β-methylandrosta-1,4-dien-3-one-17β-carboxylic acid.

81. The compound of claim 2 which is 9α-fluoro-11β-hydroxy-16α-methyl-17α-propoxycarbonyloxyandrosta-1,4-dien-3-one-17β-carboxylic acid.

82. The compound of claim 2 which is 9α-fluoro-11β-hydroxy-17α-methoxycarbonyloxy-16α-methylandrosta-1,4-dien-3-one-17β-carboxylic acid.

83. The compound of claim 2 which is 11β-hydroxy-17α-methoxycarbonyloxyandrost-4-en-3-one-17β-carboxylic acid, 17α-ethoxycarbonyloxy-11β-hydroxyandrost-4-en-3-one-17β-carboxylic acid, 17α-butoxycarbonyloxy-11β-hydroxyandrost-4-en-3-one-17β-carboxylic acid, or 11β-hydroxy-17α-isopropoxycarbonyloxyandrost-4-en-3-one-17β-carboxylic acid.

84. The compound of claim 2 which is sodium 11β-hydroxy-17α-methoxycarbonyloxyandrost-4-en-3-one-17β-carboxylate, sodium 17α-ethoxycarbonyloxy-11β-hydroxyandrost-4-en-3-one-17β-carboxylate, sodium 17α-butoxycarbonyloxy-11β-hydroxyandrost-4-en-3-one-17β-carboxylate, or sodium 11β-hydroxy-17α-isopropoxycarbonyloxyandrost-4-en-3-one-17β-carboxylate.

85. The compound of claim 2 which is chloromethyl 17α-chlorocarbonyloxy-11β-hydroxyandrost-4-en-3-one-17β-carboxylate.

86. The compound of claim 2 which is chloromethyl 17α-ethoxycarbonyloxy-9α-fluoro-16α-methylandrosta-1,4-dien-3,11-dione-17β-carboxylate.

87. The compound of claim 2 which is chloromethyl 9α-fluoro-17α-isopropoxycarbonyloxy-16β-methylandrosta-1,4-diene-3,11-dione-17β-carboxylate.

88. A pharmaceutical composition of matter comprising an anti-inflammatory effective amount of a compound of claim 1 or 2 having the structural formula (I), in combination with a non-toxic pharmaceutically acceptable carrier therefor suitable for topical or other local application.

89. A method for alleviating inflammation in or on a warm-blooded animal exhibiting a topical inflammatory response, which comprises topically administering thereto an anti-inflammatory effective amount of a composition of claim 88.

90. A method for alleviating inflammation in or on a warm-blooded animal exhibiting a localized inflammatory response, which comprises locally administering thereto an anit-inflammatory effective amount of composition of claim 88.

91. A compound of claim 13 wherein $C_1$-$C_6$ monohaloalkyl is $C_1$≢-$C_6$ monofluoroalkyl.

92. A compound of claim 91 wherein $C_1$-$C_6$ monofluoroalkyl is fluoromethyl.

93. A compound of claim 91 wherein $R_2$ is $C_1$-$C_6$ alkyl.

94. A compound of claim 92 wherein $R_2$ is $C_1$-$C_6$ alkyl.

95. A compound of claim 91 wherein X is —I—.

96. A compound of claim 95 wherein $R_4$ and $R_5$ are hydrogen.

97. A compound of claim 96 wherein $R_3$ is hydrogen.

98. A compound of claim 95 wherein at least one of $R_4$ and $R_5$ is fluoro.

99. A compound of claim 95 wherein $R_4$ is fluoro and $R_5$ is hydrogen.

100. A compound of claim 99 wherein $R_3$ is α-methyl or β-methyl.

101. A compound of claim 2 which is fluoromethyl 11β-hydroxy-17α-isopropoxycarbonyloxyandrost-4-en-3-one-17β-carboxylate.

102. The compound of claim 2 which is fluoromethyl 17α-ethoxycarbonyloxy-9α-fluoro-11β-hydroxy-16α-methylandrosta-1,4-dien-3-one-17β-carboxylate.

103. The compound of claim 2 which is fluoromethyl 9α-fluoro-11β-hydroxy-16α-methyl-17α-n-propoxycarbonyloxyandrosta-1,4-dien-3-one-17β-carboxylate.

104. A compound of claim 1 or 2, said compound having the structural formula (I) wherein $R_3$, $R_4$ and $R_5$ are hydrogen and the 1,2 linkage is saturated or unsaturated.

105. A compound of claim 1 or 2, said compound having the structural formula (I) wherein $R_3$ is selected from hydrogen or methyl, $R_4$ is fluoro and $R_5$ is hydrogen and the 1,2 linkage is saturated or unsaturated.

106. A compound of claim 1 or 2, said compound having the structural formula (I) wherein $R_3$ is hydrogen or methyl, $R_4$ is hydrogen or fluoro and $R_5$ is fluoro or methyl and the 1,2 linkage is unsaturated.

107. A compound of claim 1 or 2, said compound having the structural formula (I) wherein $R_3$ is

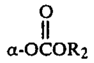

and wherein $R_4$ is fluoro and $R_5$ is hydrogen and the 1,2 linkage is unsaturated.

108. A compound of claim 59 wherein $R_3$ is hdyrogen or methyl, $R_4$ is hydrogen and $R_5$ is hydrogen or chloro and the 1,2 linkage is saturated or unsaturated.

109. The compound of claim 45 wherein $R_3$ is α-methyl and the 1,2 linkage is unsaturated.

110. A compound of the formula

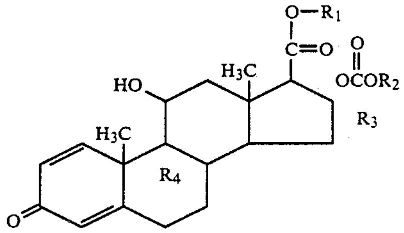

wherein $R_1$ is $C_1$-$C_6$ (monohalo)alkyl, $R_2$ is $C_1$-$C_6$ alkyl, $R_3$ is hydrogen, α-methyl or β-methyl and $R_4$ is hydrogen or fluoro.

111. A compound of claim 110 wherein $R_1$ is chloromethyl.

112. A compound of claim 110 wherein $R_3$ is α-methyl and $R_4$ is fluoro.

113. A compound of the formula

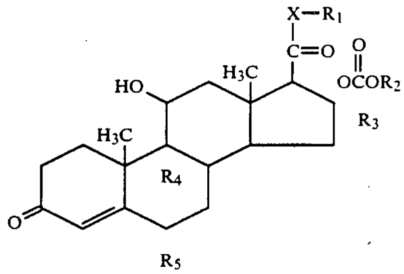

(I)

wherein:

$R_1$ is —$CH_2COOR_6$ wherein $R_6$ is $C_1$-$C_6$ alkyl; —$CH_2$—Y—($C_1$-$C_6$ alkyl) wherein Y is —S—, —SO—, —$SO_2$— or —O—; or $$-CH_2O\overset{O}{\overset{\|}{C}}R_6'$$

wherein $R_6'$ is $C_1$–$C_6$ alkyl or phenyl;

$R_2$ is $C_1$–$C_6$ alkyl, $C_3$–$C_8$ cycloalkyl, phenyl, benzyl or $C_1$–$C_6$ (monohalo or polyhalo)alkyl;

$R_3$ is hydrogen, α-hydroxy, α-methyl, β-methyl or $$\alpha\text{-}O\overset{O}{\overset{\|}{C}}R_2$$

wherein $R_2$ is as defined above;

$R_4$ is hydrogen or fluoro;

$R_5$ is hydrogen or fluoro;

X is —O— or —S—;

and the dotted line in ring A indicates that the 1,2-linkage is saturated or unsaturated.

* * * * *

UNITED STATES PATENT AND TRADEMARK OFFICE

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 1, line 9, "Sept. 18" should read --Sept. 15--.

In Column 2, lines 45-57, delete the structural formula (I), and insert in its stead:

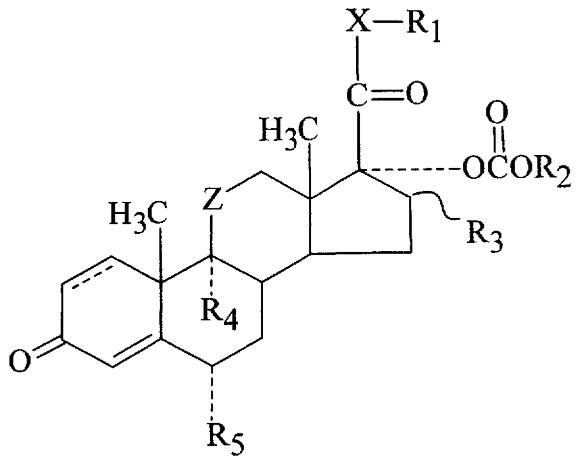

(I)

In Column 5, line 25, "timethylene" should read --trimethylene--.

UNITED STATES PATENT AND TRADEMARK OFFICE
CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 5, lines 28 and 29, after "dialkylcarbamoyl", insert --groupings are of the type--.

In Column 10, lines 1-13, delete the structural formula (II) and insert in its stead:

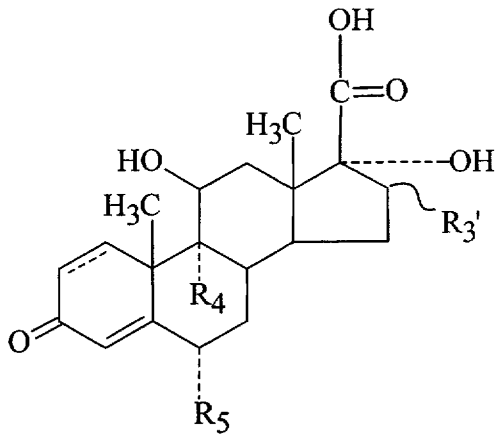

(II)

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 10, lines 20-30, delete the structural formula and insert in its stead:

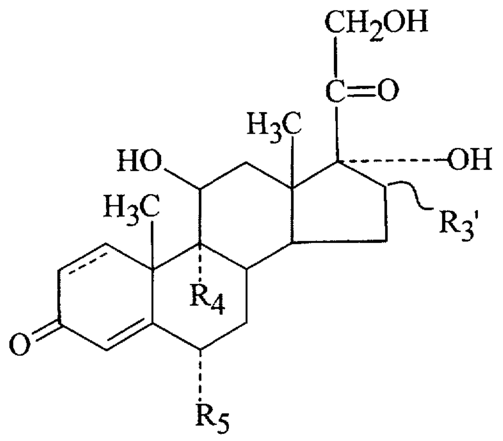

UNITED STATES PATENT AND TRADEMARK OFFICE
CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 10, lines 50-60, delete the structural formula (III) and insert in its stead:

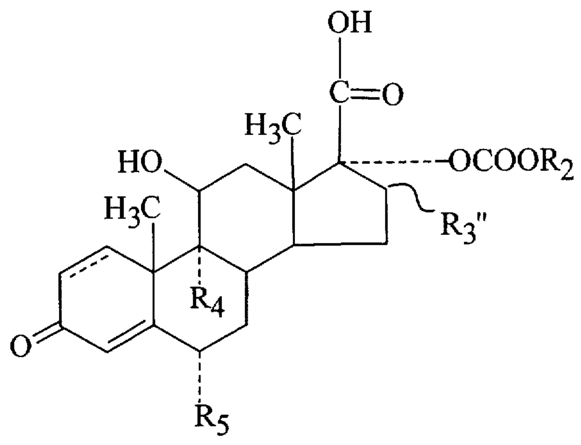

(III)

UNITED STATES PATENT AND TRADEMARK OFFICE
CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 11, lines 15-25, delete the structural formula (IV) and insert in its stead:

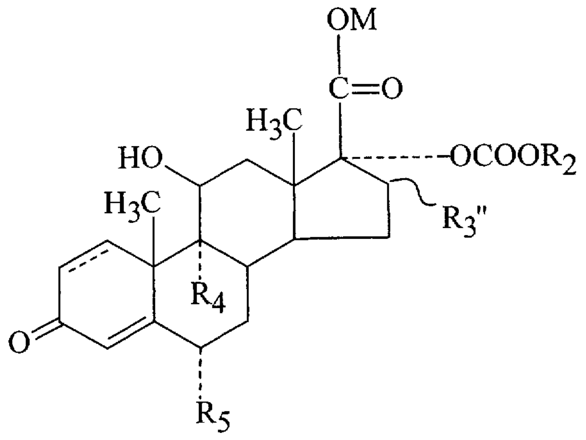

(IV)

In Column 12, line 8, "wtih" should read --with--.

UNITED STATES PATENT AND TRADEMARK OFFICE
CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 13, lines 1-12, delete structural formula (V) and insert in its stead:

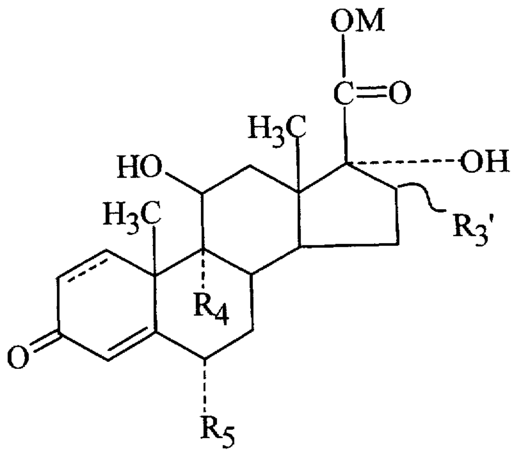

(V)

UNITED STATES PATENT AND TRADEMARK OFFICE
CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 13, lines 18-29, delete the structural formula (VI) and insert in its stead:

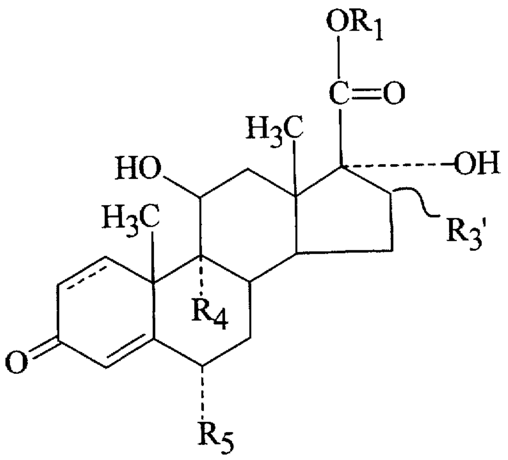

(VI)

In Column 13, line 50, after "formula (I) wherein $R_1$ is", insert --a sulfinyl- or sulfonyl-containing group [e.g., when $R_1$ is--.

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 14, lines 5-17, delete the structural formula (VIII) and insert in its stead:

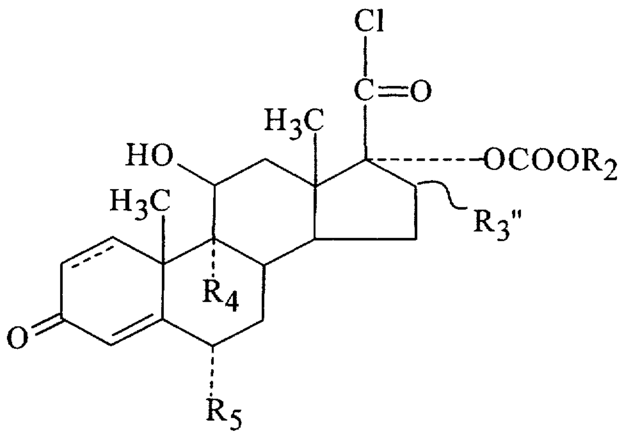

(VIII)

In Column 14, line 42, "phuosgene" should read --phosgene--.

UNITED STATES PATENT AND TRADEMARK OFFICE
CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 14, lines 45-57, delete the structural formula (VII) and insert in its stead:

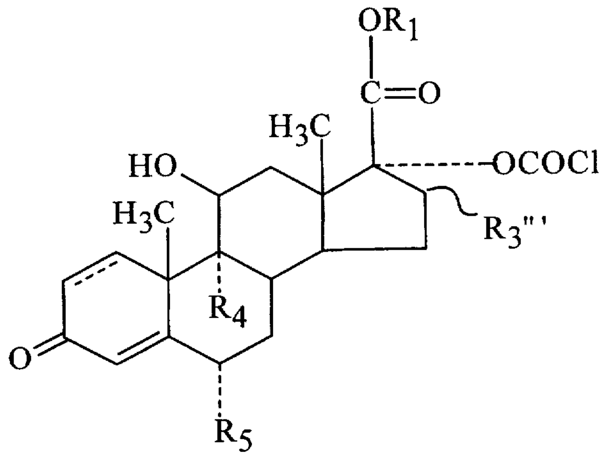

(VII)

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 15, lines 23-34, delete the structural formula (X) and insert in its stead:

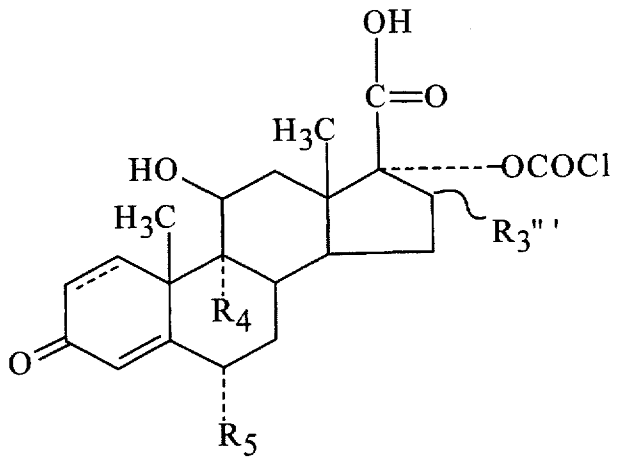

(X)

In Column 16, line 40, "aceytonitrile" should read --acetonitrile--.

UNITED STATES PATENT AND TRADEMARK OFFICE
CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 16, lines 55-68, delete the structural formula (XI) and insert in its stead:

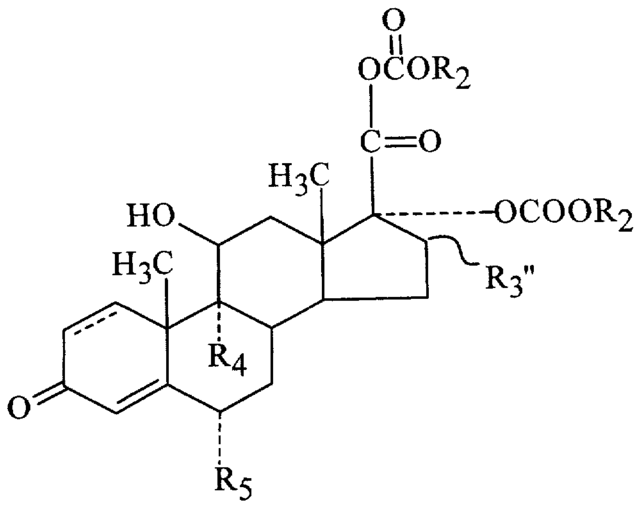

(XI)

In Column 17, line 25, "suchy" should read --such--.

UNITED STATES PATENT AND TRADEMARK OFFICE

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 17, lines 36-46, delete the structural formula (IX) and insert in its stead:

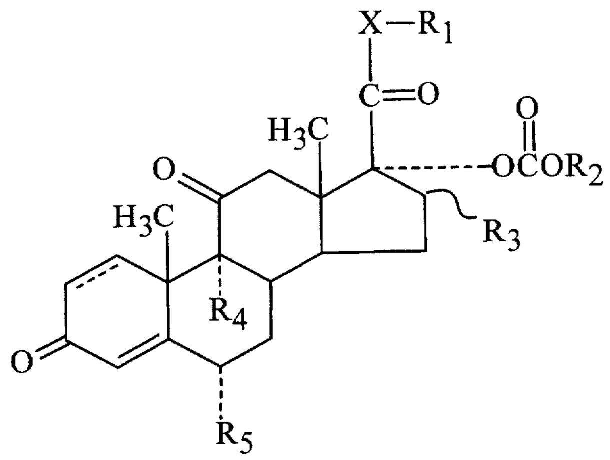

(IX)

In Column 18, line 20, "and" should read --an--.

UNITED STATES PATENT AND TRADEMARK OFFICE

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 18, line 60, "As" should read --An--.

In Column 20, line 3, "MeKenzie" should read --McKenzie--.

In Column 26, line 63, "asigned" should read --assigned--.

In Column 33, line 24, after "tioned", the period (".") should be a colon (--:--).

In Column 33, line 32, "propylactic" should read --prophylactic--.

In Column 34, line 39, "17α/e-" should read --17α-e- --.

UNITED STATES PATENT AND TRADEMARK OFFICE

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 35, lines 47-58, delete the structural formula and insert in its stead:

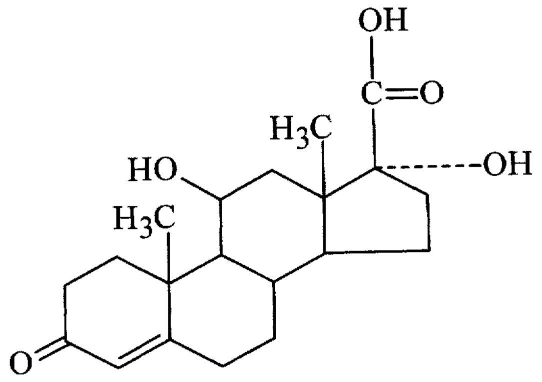

In Column 35, lines 67-68, "filtration" should read --filtrate--.

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 36, lines 12-23, delete the structural formula and insert in its stead:

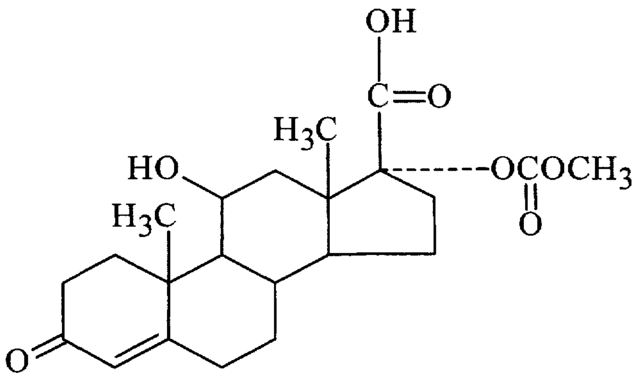

UNITED STATES PATENT AND TRADEMARK OFFICE
CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 37, lines 15-25, delete the structural formula and insert in its stead:

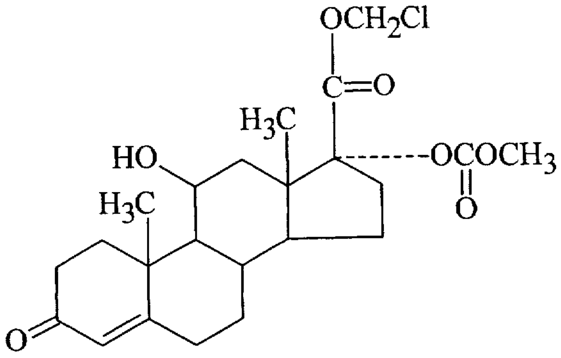

In Column 37, line 53, after "nmr($CDCl_3$)" and before "δ5.60", insert --δ5.80,--.

In Column 38, line 24, "mmol6)" should read --mmol)--.

UNITED STATES PATENT AND TRADEMARK OFFICE

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 38, lines 51-61, delete the structural formula and insert in its stead:

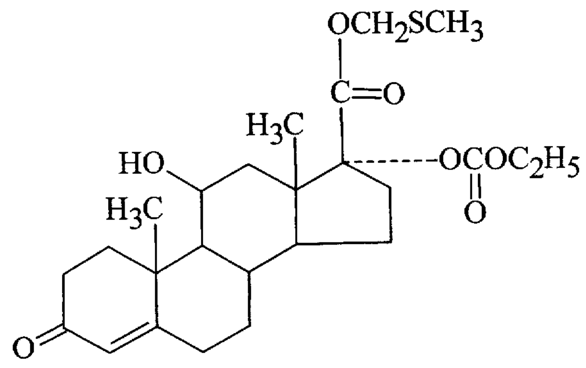

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 39, lines 6-16, delete the structural formula and insert in its stead:

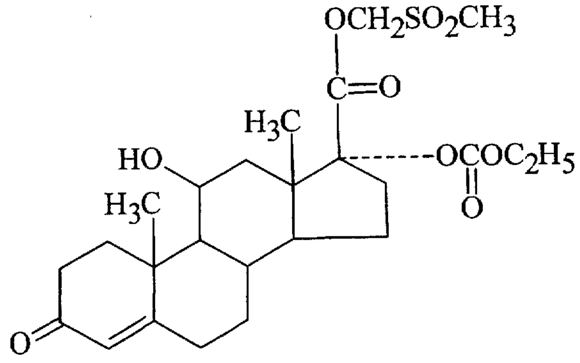

In Column 39, line 22, "17β-ethoxycarbonyloxy" should read --17α-ethoxycarbonyloxy--.

In Column 40, line 18, "11α,17β-dihydroxy" should read --11β,17α-dihydroxy--.

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 40, lines 35-46, delete the structural formula and insert in its stead:

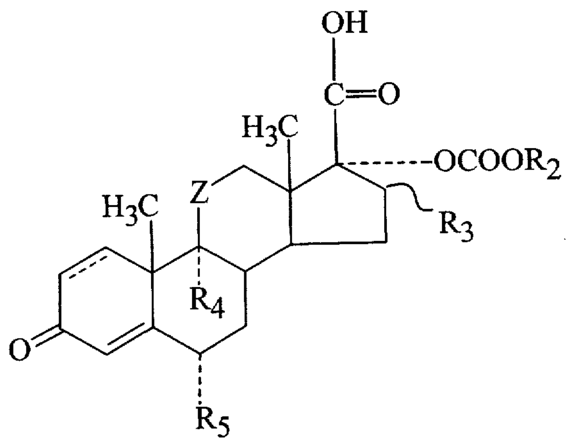

In Column 40, line 48, delete "Compounds".

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Columns 40 and 41, in the table in Example 6A, for each of Compound Nos. 6A-1 through 6A-15, under column "Z", at each occurrence,

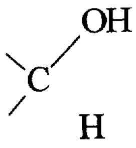 should read 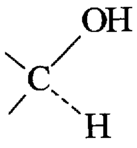

In Column 41, line 60, at the bottom of the table, before "6a-1 to 6A-15 above", insert --Compounds--.

In Column 41, line 62, "17α-benzyloxo" should read --17α-benzyloxy--.

In Column 43, line 13, "aicd" should read --acid--.

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 44, lines 10-21, delete the structural formula and insert in its stead:

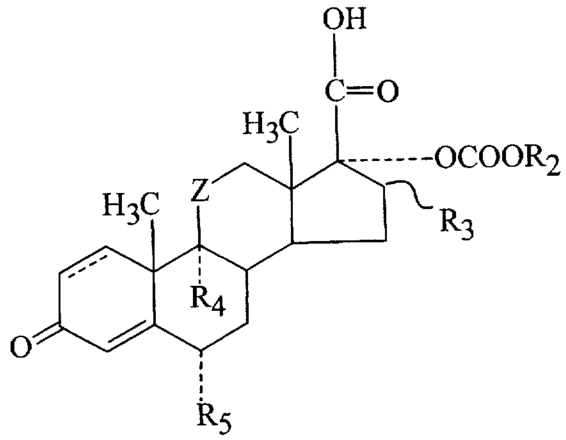

UNITED STATES PATENT AND TRADEMARK OFFICE

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Columns 44, 45-46 and 47-48, in the table in Example 6B, for each of Compound Nos. 6B-3, 6B-4, 6B-5, 6B-7, 6B-8, 6B-9, 6B-11, 6B-12, 6B-13, and 6B-15 through 6B-25, under column "Z", at each occurrence,

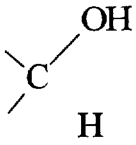 should read 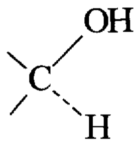

UNITED STATES PATENT AND TRADEMARK OFFICE
CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 48, lines 15-26, delete the structural formula (VI) and insert in its stead:

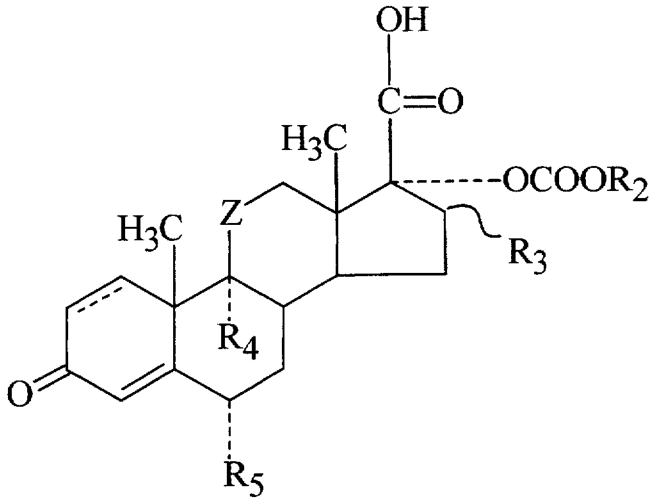

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Columns 48 and 49-50, in the table in Example 6C, for each of Compound Nos. 6C-1 through 6C-11, under column "Z", at each occurrence,

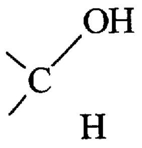 should read 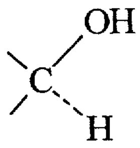

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 50, lines 33-45, delete the structural formula and insert in its stead:

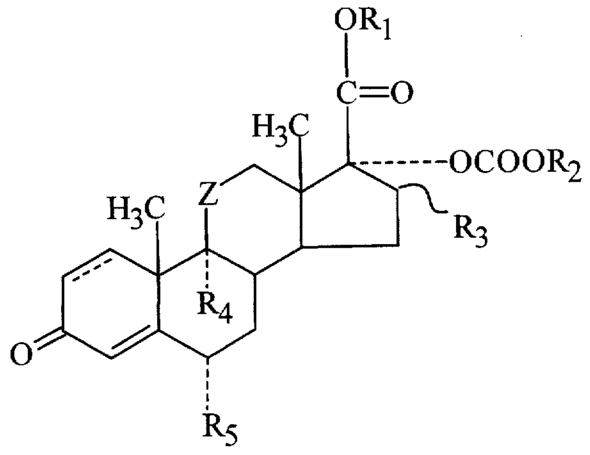

UNITED STATES PATENT AND TRADEMARK OFFICE

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Columns 50 through 56, in the table in Example 7A, for each of Compound Nos. 7A-1 through 7A-18 and 7A-21 through 7A-30, under column "Z", at each occurrence,

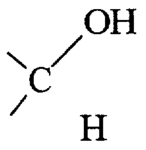 should read 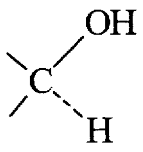

In Column 55, line 20, "17β-ethoxycarbonyloxy" should read --17α-ethoxycarbonyloxy--.

In Column 56, line 14, "methylandrost" should read --methylandrosta--.

UNITED STATES PATENT AND TRADEMARK OFFICE
CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 56, lines 46-56, delete the structural formula and insert in its stead:

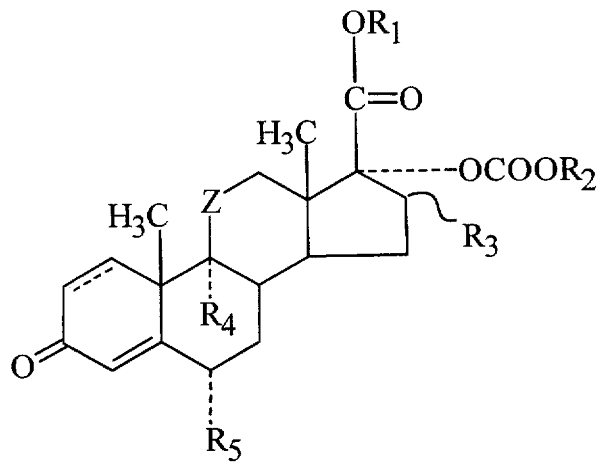

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Columns 56 through 66, in the table in Example 7B, for each of Compound Nos. 7B-1 through 7B-7, 7B-14 through 7B-18, 7B-22 through 7B-29, 7B-33 through 7B-40, and 7B-44 through 7B-64, under column "Z", at each occurrence,

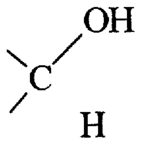 should read 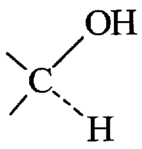

UNITED STATES PATENT AND TRADEMARK OFFICE

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 66, lines 40-50, delete the structural formula and insert in its stead:

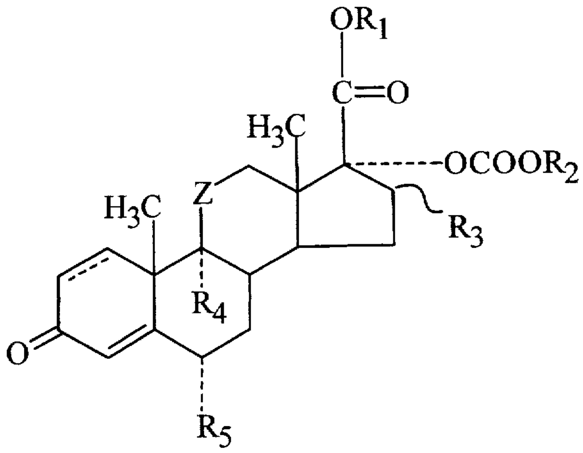

UNITED STATES PATENT AND TRADEMARK OFFICE

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Columns 66 through 68, in the table in Example 7C, for each of Compound Nos. 7C-1 through 7C-13, under column "Z", at each occurrence,

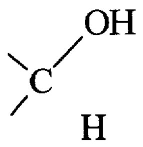 should read 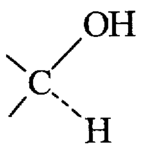

In Column 69, line 39, "11α," should read --11β,--.

UNITED STATES PATENT AND TRADEMARK OFFICE

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 69, lines 52-62, delete the structural formula and insert in its stead:

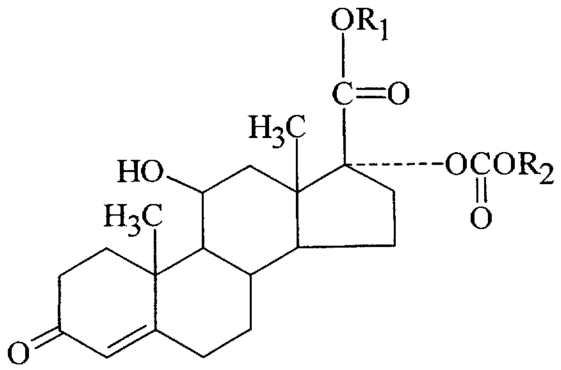

In Column 70, lines 3-13, delete the structural formula.

In Column 70, line 31, "thylfulfonylmethyl" should read --thylsulfonylmethyl--.

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 70, lines 37-46, delete the structural formula and insert in its stead:

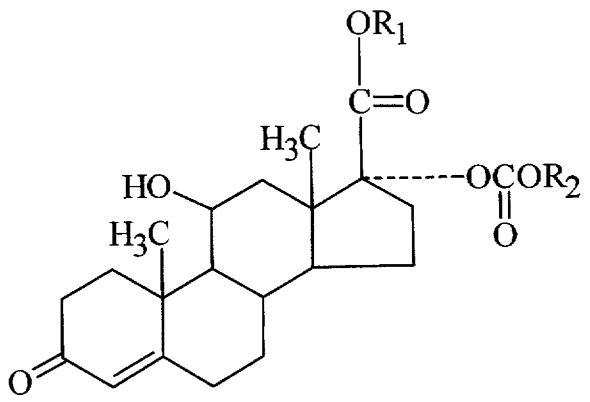

UNITED STATES PATENT AND TRADEMARK OFFICE
CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 71, lines 2-11, delete the structural formula and insert in its stead:

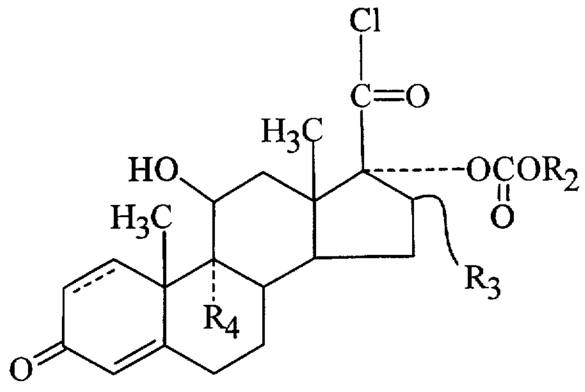

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 71, lines 22-31, delete the structural formula and insert in its stead:

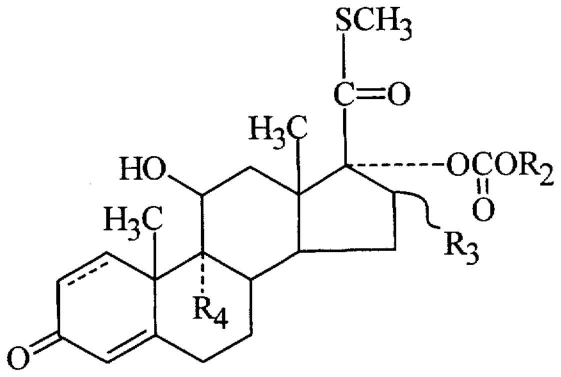

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 71, lines 44-54, delete the structural formula and insert in its stead:

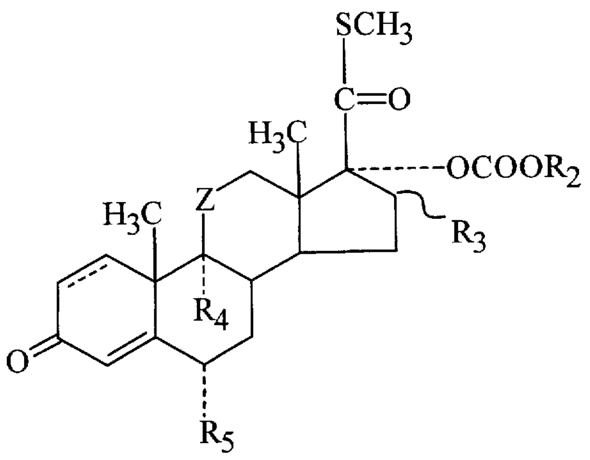

UNITED STATES PATENT AND TRADEMARK OFFICE

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 72, lines 5-13, delete the structural formula and insert in its stead:

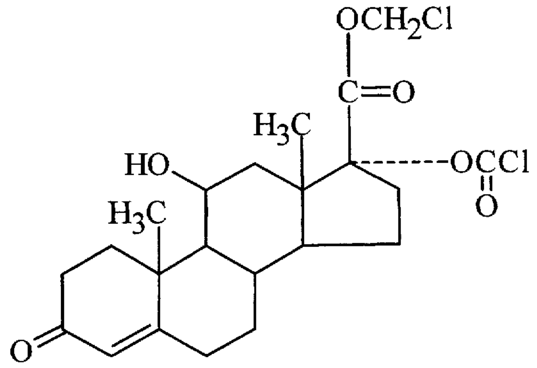

UNITED STATES PATENT AND TRADEMARK OFFICE

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 72, lines 51-60, delete the structural formula and insert in its stead:

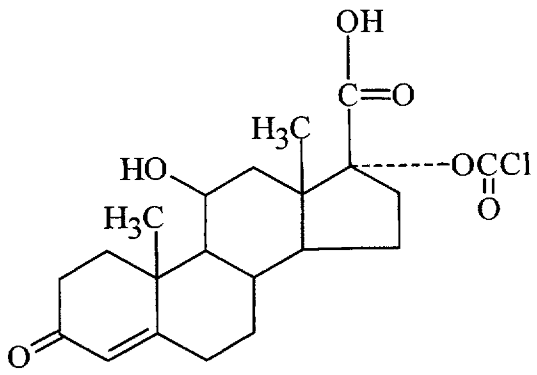

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 74, lines 2-14, delete the structural formula and insert in its stead:

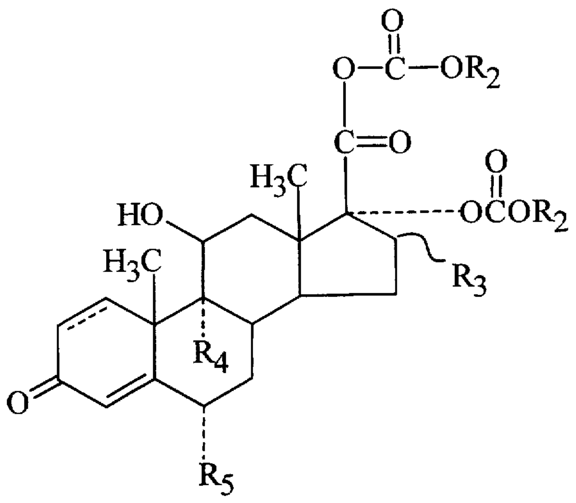

UNITED STATES PATENT AND TRADEMARK OFFICE

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 74, lines 47-55, delete the structural formula and insert in its stead:

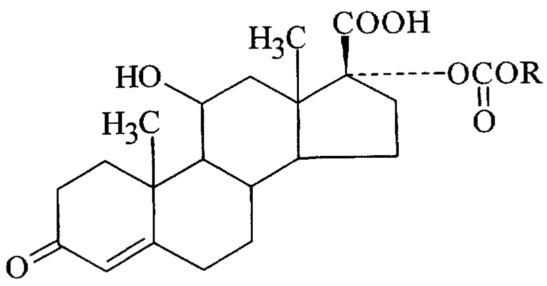

In Column 76, line 6, "dikmethylpyrrolidine" should read --dimethylpyrrolidine--.

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 76, lines 17-30, delete the structural formula and insert in its stead:

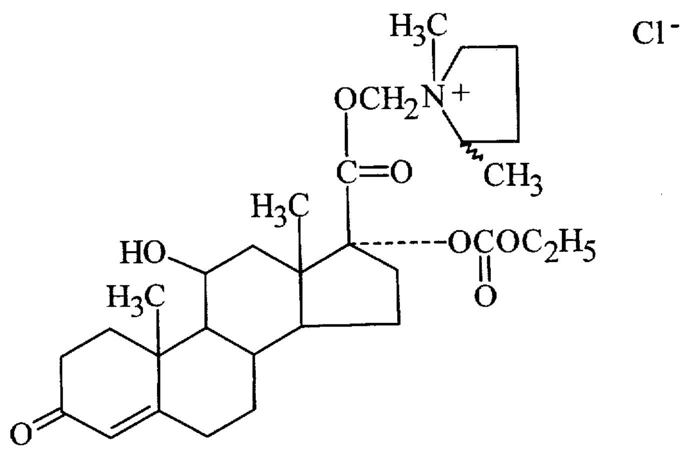

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 76, lines 37-48, delete the structural formula and insert in its stead:

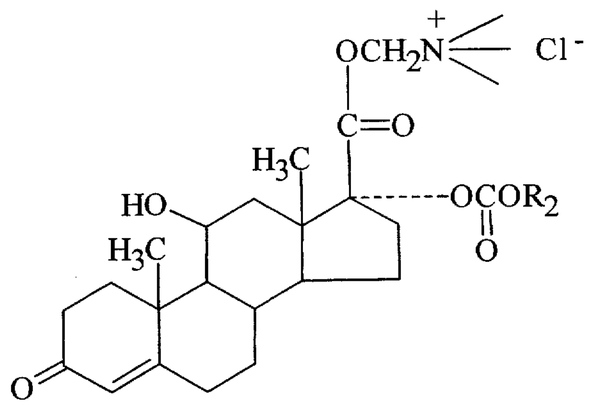

UNITED STATES PATENT AND TRADEMARK OFFICE

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 76, lines 52-55,

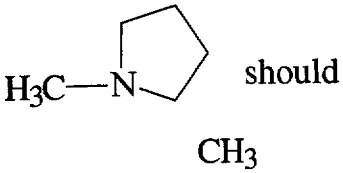

should read

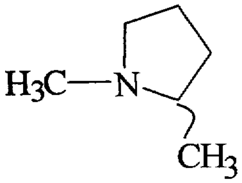

In Column 77, lines 3-12, delete the structural formula.

In Column 77, lines 17-20,

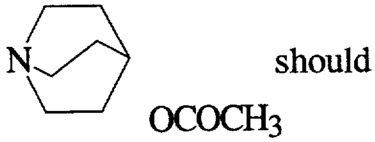

should read

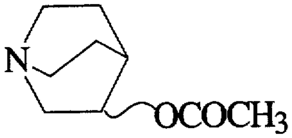

In Column 77, lines 57-58, "Benalkonium" should read --Benzalkonium--.

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 78, line 38, "Eye Drops" should be underlined.

In Column 79, lines 14-25, delete the structural formula and insert in its stead:

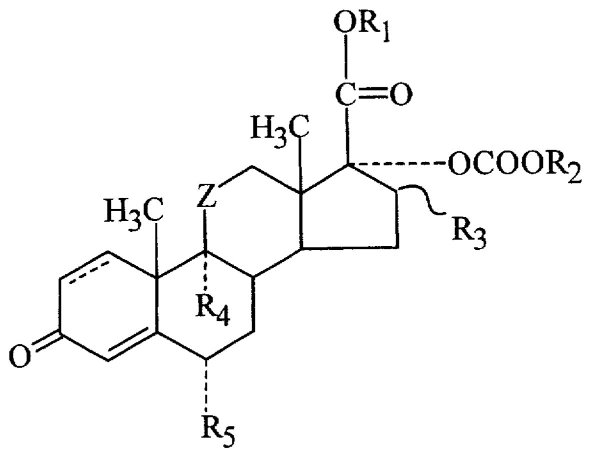

UNITED STATES PATENT AND TRADEMARK OFFICE

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Columns 79-80, lines 24-38, in the table in Example 29, for each of Compound Nos. 29-1 and 29-2, under column "Z", at each occurrence,

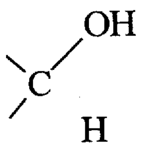 should read 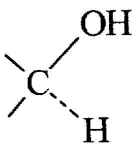

UNITED STATES PATENT AND TRADEMARK OFFICE
CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 80, lines 2-12, part (a) of Claim 1, delete the structural formula (I) and insert in its stead:

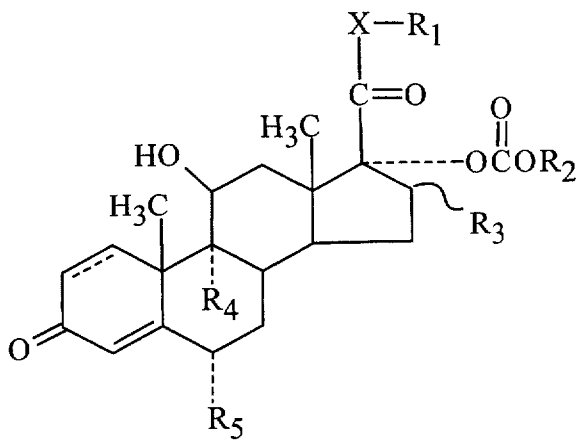

(I)

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 81, lines 55-65, part (c) of Claim 1, delete the structural formula and insert in its stead:

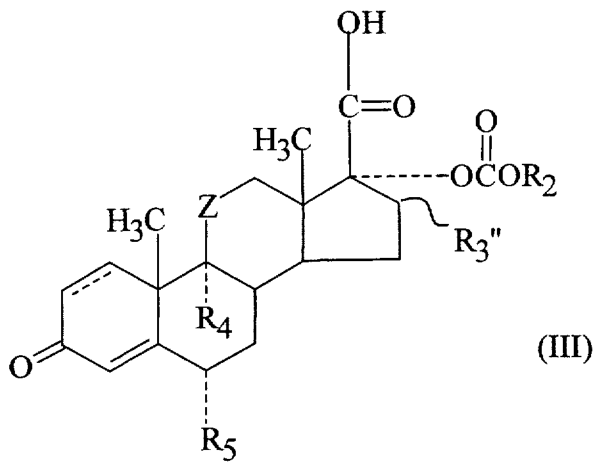

(III)

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 82, lines 15-24, part (d) of Claim 1, delete the structural formula (IV) and insert in its stead:

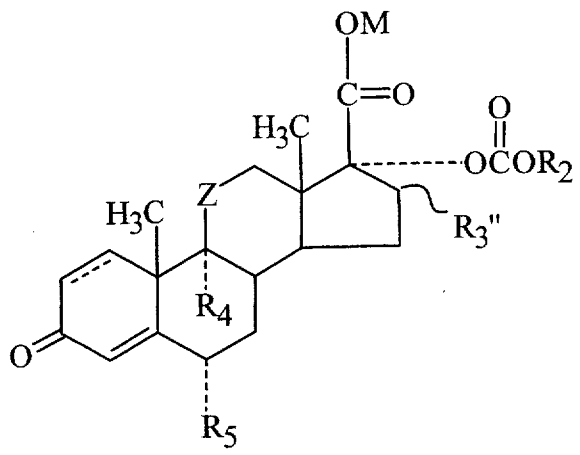

(IV)

UNITED STATES PATENT AND TRADEMARK OFFICE

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 82, lines 34-44, part (e) of Claim 1, delete the structural formula (VII) and insert in its stead:

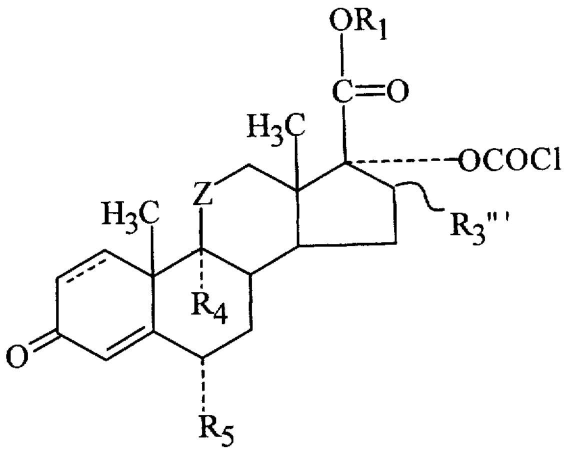

(VII)

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 82, lines 53-64, part (f) of Claim 1, delete the structural formula (VIII) and insert in its stead:

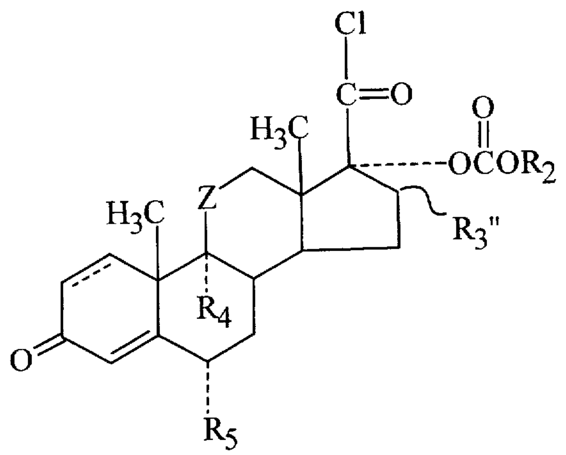

(VIII)

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 83, lines 2-12, part (g) of Claim 1, delete the structural formula (IX) and insert in its stead:

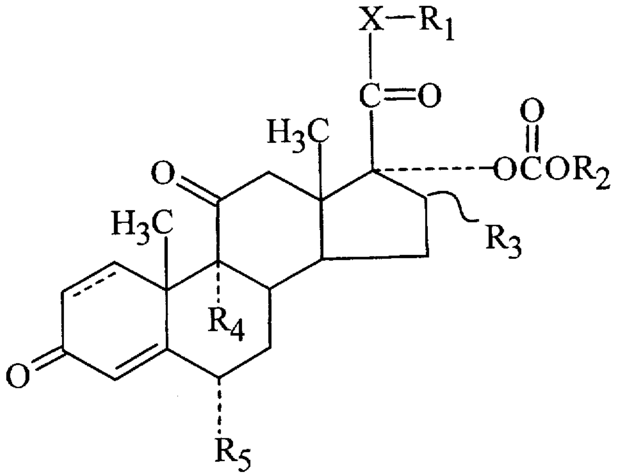

(IX)

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 83, lines 20-31, part (a) of Claim 2, delete the structural formula (I) and insert in its stead:

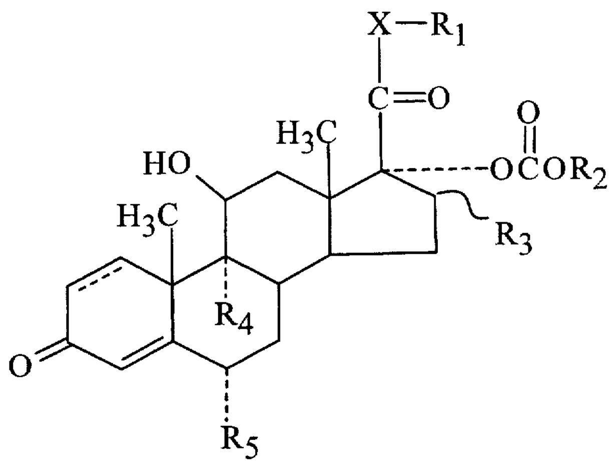

(I)

UNITED STATES PATENT AND TRADEMARK OFFICE
CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 83, line 49, part (a) of Claim 2, in the definition of $R_3$, "β-methyl, β-methyl" should read --α-methyl, β-methyl--.

In Column 84, lines 2-13, part (c) of Claim 2, delete the structural formula (III) and insert in its stead:

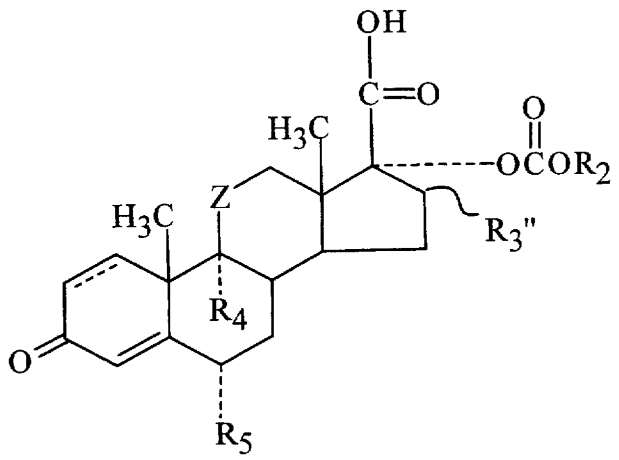

(III)

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 84, lines 31-43, part (d) of Claim 2, delete the structural formula (IV) and insert in its stead:

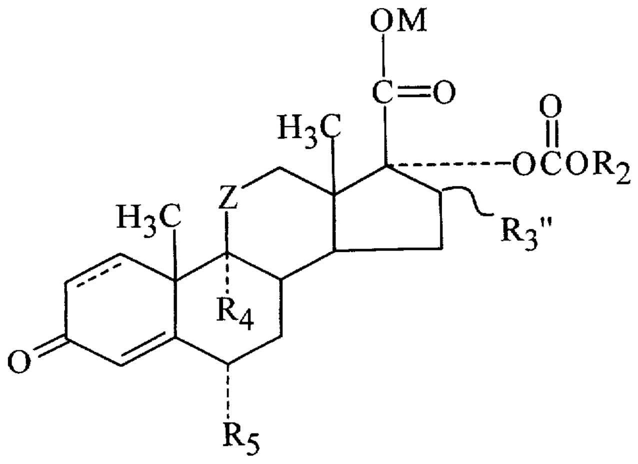

(IV)

UNITED STATES PATENT AND TRADEMARK OFFICE

CERTIFICATE OF CORRECTION

PATENT NO. : 4,996,335

DATED : February 26, 1991

INVENTOR(S) : Nicholas S. BODOR

It is certified that error appears in the above-identified patent and that said Letters Patent is hereby corrected as shown below:

In Column 84, lines 51-62, part (e) of Claim 2, delete the structural formula (VII) and insert in its stead:

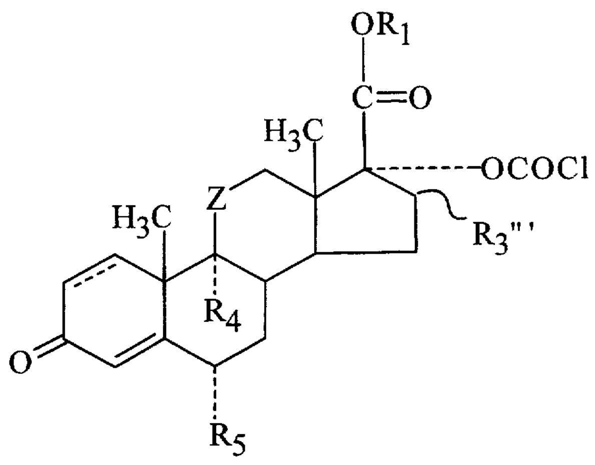

(VII)

UNITED STATES PATENT AND TRADEMARK OFFICE
CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 85, lines 2-12, part (f) of Claim 2, delete the structural formula (VIII) and insert in its stead:

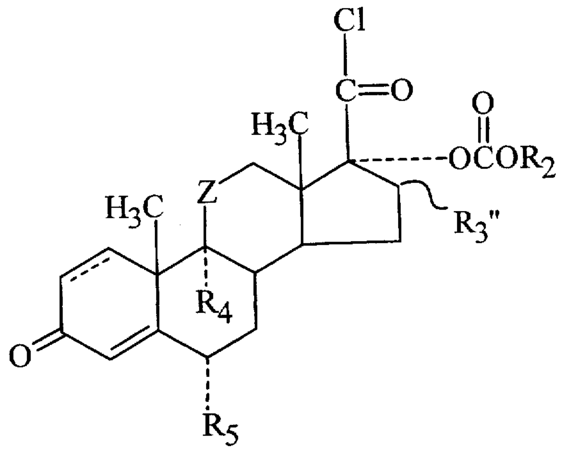

(VIII)

UNITED STATES PATENT AND TRADEMARK OFFICE
CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 85, lines 18-28, part (g) of Claim 2, delete the structural formula (IX) and insert in its stead:

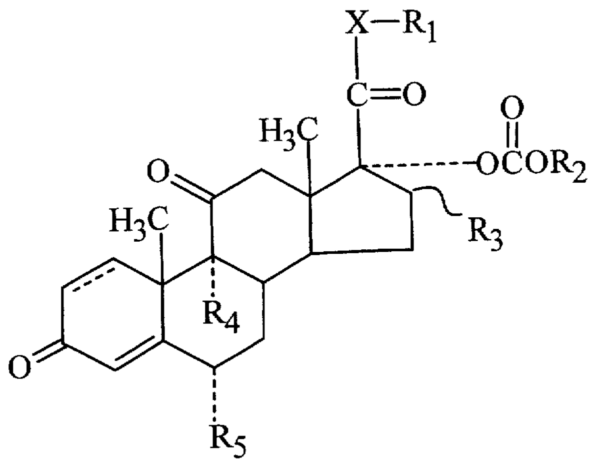

(IX)

In Column 87, line 16, Claim 50, "sentss" should read --sents--.

UNITED STATES PATENT AND TRADEMARK OFFICE

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 88, line 42, Claim 73, after "claim 2" and before "is", insert --which--.

In Column 89, line 24, Claim 86, "dien" should read --diene--.

In Column 89, line 53, Claim 95, delete "-I-" and insert -- -O- --.

UNITED STATES PATENT AND TRADEMARK OFFICE
CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 90, lines 33-42, Claim 110, delete the structural formula and insert in its stead:

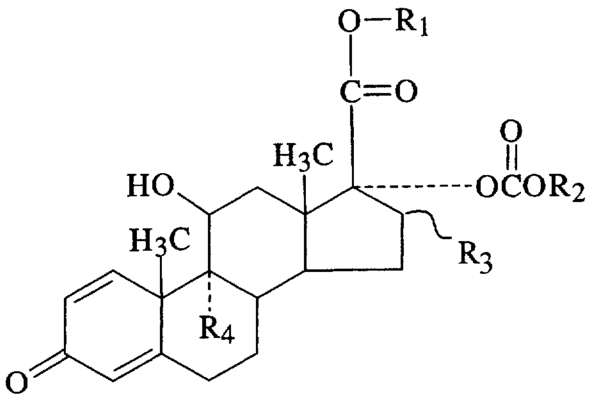

UNITED STATES PATENT AND TRADEMARK OFFICE

CERTIFICATE OF CORRECTION

PATENT NO. : 4,996,335
DATED : February 26, 1991
INVENTOR(S) : Nicholas S. BODOR It is certified that error appears in the above-identified patent and that said Letters Patent is hereby corrected as shown below:

In Column 90, lines 52-63, Claim 113, delete the structural formula (I) and insert in its stead:

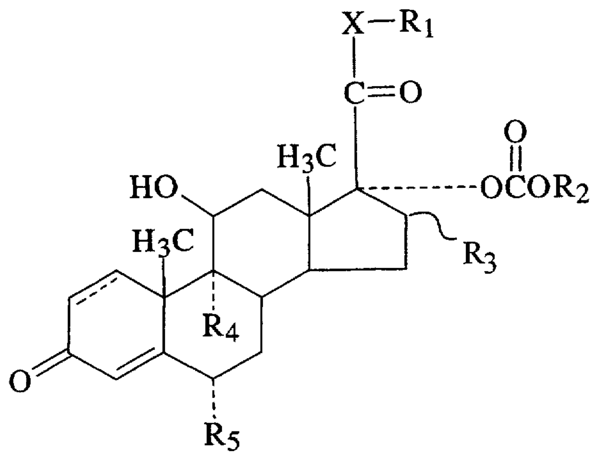

(I)

Signed and Sealed this

Ninth Day of June, 1998

Attest:

BRUCE LEHMAN

Attesting Officer

Commissioner of Patents and Trademarks

UNITED STATES PATENT AND TRADEMARK OFFICE

CERTIFICATE EXTENDING PATENT TERM
UNDER 35 U.S.C. § 156

| | | |
|---|---|---|
| PATENT NO. | : | 4,996,335 |
| ISSUED | : | February 26, 1991 |
| INVENTOR | : | Nicholas S. Bodor |
| PATENT OWNER | : | Nicholas S. Bodor |
| PRODUCT | : | LOTEMAX™ and ALREX™ (loteprednol etabonate) |

This is to certify that an application under 35 U.S.C. § 156 has been filed in the U.S. Patent and Trademark Office, requesting extension of the term of U.S. Patent No. 4,996,335 based upon the regulatory review of the product loteprednol etabonate (LOTEMAX™ and ALREX™) by the Food and Drug Administration. Since it appears that the requirements of the law have been met, this certificate extends the term of the patent for the period of 1,473 days from February 26, 2008, the original expiration date of the patent, subject to the provisions of 35 U.S.C. § 41(b), with all rights pertaining thereto as provided by 35 U.S.C. § 156(b).

I have caused the seal of the U.S. Patent and Trademark Office to be affixed this 12th day of September 2000.

Q. Todd Dickinson
Under Secretary of Commerce for Intellectual Property and Director of the United States Patent and Trademark Office